United States Patent
Ghatnekar et al.

(10) Patent No.: US 10,398,140 B2
(45) Date of Patent: Sep. 3, 2019

(54) ALPHA CONNEXIN C-TERMINAL (ACT) PEPTIDES AND METHODS OF USE THEREOF

(71) Applicant: MUSC Foundation for Research Development, Charleston, SC (US)

(72) Inventors: Gautam Ghatnekar, Charleston, SC (US); Robert Gourdie, Charleston, SC (US); Jane Jourdan, Charleston, SC (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 56 days.

(21) Appl. No.: 15/825,399

(22) Filed: Nov. 29, 2017

(65) Prior Publication Data

US 2018/0077923 A1 Mar. 22, 2018

Related U.S. Application Data

(60) Continuation of application No. 15/195,569, filed on Jun. 28, 2016, now Pat. No. 9,844,214, which is a continuation of application No. 14/932,630, filed on Nov. 4, 2015, now Pat. No. 9,408,381, which is a continuation of application No. 13/935,848, filed on Jul. 5, 2013, now abandoned, which is a continuation-in-part of application No. 13/842,506, filed on Mar. 15, 2013, now Pat. No. 8,916,515, which is a continuation of application No. 13/715,626, filed on Dec. 14, 2012, now Pat. No. 8,809,257, which is a continuation of application No. 12/871,461, filed on Aug. 30, 2010, now Pat. No. 8,357,668, which is a division of application No. 11/721,529, filed as application No. PCT/US2005/046442 on Dec. 20, 2005, now Pat. No. 7,786,074, said application No. 13/935,848 is a continuation of application No. 12/665,596, filed as application No. PCT/US2008/067944 on Jun. 23, 2008, now abandoned.

(60) Provisional application No. 60/671,796, filed on Apr. 15, 2005, provisional application No. 60/638,366, filed on Dec. 21, 2004, provisional application No. 60/945,493, filed on Jun. 21, 2007.

(51) Int. Cl.
| | |
|---|---|
| *C07K 7/06* | (2006.01) |
| *A01N 1/02* | (2006.01) |
| *A61K 38/17* | (2006.01) |
| *C07K 14/705* | (2006.01) |

(52) U.S. Cl.
CPC ............ *A01N 1/0226* (2013.01); *A01N 1/021* (2013.01); *A61K 38/177* (2013.01); *A61K 38/1709* (2013.01); *C07K 14/705* (2013.01)

(58) Field of Classification Search
CPC ............ C07K 7/06; C07K 14/47; A01N 1/02
See application file for complete search history.

(56) References Cited

U.S. PATENT DOCUMENTS

| | | |
|---|---|---|
| 5,234,809 A | 8/1993 | Boom et al. |
| 6,080,724 A | 6/2000 | Chassaing et al. |
| 6,685,971 B2 | 2/2004 | Xu et al. |
| 6,991,813 B2 | 1/2006 | Xu et al. |
| 7,098,190 B1 | 8/2006 | Becker et al. |
| 7,786,074 B2 | 8/2010 | Gourdie et al. |
| 7,888,319 B2 | 2/2011 | Gourdie et al. |
| 8,357,668 B2 | 1/2013 | Gourdie et al. |
| 8,809,257 B2 | 8/2014 | Ghatnekar |
| 8,859,733 B2 | 10/2014 | Ghatnekar |
| 8,916,515 B2 | 12/2014 | Ghatnekar |
| 9,394,351 B2 | 7/2016 | Ghatnekar et al. |
| 9,408,381 B2 | 8/2016 | Ghatnekar et al. |
| 9,844,214 B2 | 12/2017 | Ghatnekar et al. |
| 9,855,313 B2 | 1/2018 | Ghatnekar et al. |
| 2003/0108886 A1 | 6/2003 | Finn et al. |
| 2003/0215424 A1 | 11/2003 | Seul et al. |
| 2004/0162232 A1 | 8/2004 | Mitts et al. |
| 2005/0053918 A1 | 3/2005 | Barnea et al. |
| 2005/0075280 A1 | 4/2005 | Larsen et al. |
| 2007/0072819 A1 | 3/2007 | Becker |
| 2007/0244062 A1 | 10/2007 | Laux |
| 2008/0095819 A1 | 4/2008 | Gourdie et al. |
| 2009/0215665 A1 | 8/2009 | Gourdie et al. |
| 2011/0059173 A1 | 3/2011 | Gourdie et al. |
| 2011/0130345 A1 | 6/2011 | Rohrer et al. |
| 2013/0177628 A1 | 7/2013 | Ghatnekar |
| 2013/0274206 A1 | 10/2013 | Ghatnekar |

(Continued)

FOREIGN PATENT DOCUMENTS

| | | |
|---|---|---|
| JP | 2003-238441 A | 8/2003 |
| WO | WO 00/44409 A1 | 8/2000 |

(Continued)

OTHER PUBLICATIONS

AlFindee et al. 2018; Inhibition of connexin hemichannels by new amphiphilic aminoglycosides without antibiotic activity. ACS Med Chem Lett. 9:697-701.*

(Continued)

*Primary Examiner* — Karen Cochrane Carlson

(74) *Attorney, Agent, or Firm* — Cooley LLP

(57) ABSTRACT

The present disclosure provides compositions and methods for treating or preventing macular degeneration in a subject. The disclosure also provides compositions and methods for preserving organs and tissues for transplantation, and for preventing cellular injury in organs or in subjects.

14 Claims, 10 Drawing Sheets

Specification includes a Sequence Listing.

(56) References Cited

U.S. PATENT DOCUMENTS

| | | |
|---|---|---|
| 2014/0018305 A1 | 1/2014 | Rohrer et al. |
| 2014/0038880 A1 | 2/2014 | Ghatnekar |
| 2015/0140060 A1 | 5/2015 | Ghatnekar et al. |
| 2016/0120171 A1 | 5/2016 | Ghatnekar et al. |
| 2017/0128523 A1 | 5/2017 | Ghatnekar et al. |
| 2017/0135334 A1 | 5/2017 | Ghatnekar et al. |
| 2018/0071363 A1 | 3/2018 | Ghatnekar et al. |

FOREIGN PATENT DOCUMENTS

| | | |
|---|---|---|
| WO | WO 00/69896 A2 | 11/2000 |
| WO | WO 02/42422 A2 | 5/2002 |
| WO | WO 02/094981 A2 | 11/2002 |
| WO | WO 03/014303 A2 | 2/2003 |
| WO | WO 2003/014303 A2 | 2/2003 |
| WO | WO 03/032964 A2 | 4/2003 |
| WO | WO 2006/069181 A2 | 6/2006 |
| WO | WO 2006/134494 A2 | 12/2006 |
| WO | WO 2008/157840 A2 | 12/2008 |

OTHER PUBLICATIONS

Deng et al. 2014; Inhibition of the connexin 43 elevation may be involved in the neuroprotective activity of leptin against brain ischemic injury. Cell Mol Neurobiol. 34: 871-879.*

EurekAlert! 2019; New approach to stroke treatment could minimize brain damage. On the web at eurekalert.org/pub_releases/2019-03/uobc-nat032019.php.*

Hill and Preiss, "Functional Analysis of Conserved Histidines in ADP-Glucose Pyrophosphorylase from *Escherichia coli*." Biochemical and Biophysical Research Communications (1998); 244 (2): 573-577.

International Preliminary Report on Patentability for International Application No. PCT/US2005/046442, dated Jun. 26, 2007, 8 pages.

International Preliminary Report on Patentability for International Application No. PCT/US2008/067944, dated Dec. 22, 2009, 6 pages.

Kyle, et al., "The N Terminus of Connexin37 Contains an α-Helix That Is Required for Channel Function," J. Biol. Chem. 284(30):20418-20427 (2009).

Lagree, et al., "Specific amino-acid residues in the N-terminus and TM3 implicated in channel function and oligomerization compatibility of connexin43," J. Cell Sci. 116:3189-3201 (2003).

Lazar, et al., "Transforming growth factor alpha: mutation of aspartic acid 47 and leucine 48 results in different biological activities." Molecular Cellular Biology (1988); 8(3): 1247-1252.

MedlinePlus, downloaded 2014. "Acute vs. chronic conditions," on the web at nlm.nih.gov/medlineplus/ency/imagepages/18126.htm.

Narita, et al., "A natural variant of bovine dopamine β-monooxygenase with phenylalanine as residue 208: purification and characterization of the variant homo- and heterotetramers of $(F208)4$ and $(F208)2(L208)_2$." FEBS Letters (1996); 396(2-3): 208-212.

Partial European Search Report, EP appl. No. 10185372.9, dated Jan. 21, 2011, 6 pages.

Pich, et al., "Prognostic relevance of cell proliferation in head and neck tumors." Annals of Oncology (2004); 15(9):1319-1329.

Rousselle, C. et al., "New advances in the transport of doxorubicin through the blood-brain barrier by a peptide vector-mediated strategy." Mol. Pharmacol. 57(4):679-686 (2000).

Shao, et al., "Structure and functional studies of N-terminal Cx43 mutants linked to oculodentodigital dysplasia," Mol. Biol. Cell. 23:3312-3321 (2012).

Spach, et al., "Electrophysiological effects of remodeling cardiac gap junctions and cell size: experimental and model studies of normal cardiac growth." Circulation Research (2000); 86: 302-311.

Tsunoda, et al., "A multivalent PDZ-domain protein assembles signalling complexes in a G-protein-coupled cascade," Nature 388:243-249 (1997).

Unger, et al., "Three-Dimensional Structure of a Recombinant Gap Junction Membrane Channel," Science 283:1176-1180 (1999).

Wikipedia, downloaded 2014. "Chronic Wound," On the web at en.wikipedia.org/wiki/Chronic_wound.

Age-Related Eye Diseases, www.nei.nih.gov, attached as pdf, available at http://www.nei.nih.gov/healthyeyes/aging_eye.asp, last visited May 6, 2013.

Alonso and Fuchs. "Stem cells of the skin epithelium", Proc Natl Acad Sci USA.(2003), 100 (Suppl 1): 11830-11835.

American Chemical Society, CAS Quick Reference Guide, CAS2052-11 04, pp. 1-22 (Nov. 2004).

Angst et al. "Dissociated spatial patterning of gap junctions and cell adhesion junctions during postnatal differentiation of ventricular myocardium", Circulation Research (1997), 80: 88-94.

Barker and Gourdie. "Connexin Interacting Proteins. In: Heart Cell Coupling and Impulse Propagation in Health and Disease", Eds., De Mello W.C. and Janse M.J., Kluwer, Boston, pp. 25-50.

Barker and Gourdie. "JNK bond regulation: why do mammalian hearts invest in connexin43?" Circ Res. (2002), 91(7): 556-558.

Barker et al. "Increased association of ZO-1 with connexin43 during remodeling of cardiac gap junctions", Circ Res (2002), 90: 317-324.

Barker et al. "Increased co-localization of connexin43 and ZO-1 in dissociated adult myocytes", Cell Commun Adhes. (2001), 8(4-6): 205-8.

Bryant and Sternberg. "Comparison of protein structural profiles by interactive computer graphics", J. Mol. Graphics (1987), 5(1):4-7.

Bucci et al. "In vivo delivery of the caveolin-1 scaffolding domain inhibits nitric oxide synthesis and reduces inflammation", Nat. Med. (2000), 6: 1362-1367.

Bukauskas et al. "Clustering of connexin 43-enhanced green fluorescent protein gap junction channels and functional coupling in living cells",. Proc Natl Acad Sci USA (2000), 97: 2556-2561.

Chen et al. "Molecular transporters for peptides: delivery of a cardioprotective epsilonPKC agonist peptide into cells and intact ischemic heart using a transport system, R(7)", Chem Biol (2001), 8: 1123-1129.

Chien, K.R. "Stem cells: lost in translation", Nature (2004), 428(6983): 607-608.

Chu et al. "Predictive Sensitivity of Human Cancer Cells iin vivo Using Semipermeable Polysulfone Fibers", Pharmacology (1998) 56(6): 318-326.

Connexin 45 (Genbank: AAH66131.1, Connexin 45 [Xenopus tropical is], attached as pdf, also available at http://www.ncbi.nlm.nih.gov/protein/AAH66131.1 (last visted Aug. 22, 2014).

Dang et al. "The carboxy-tail of connexin-43 localizes to the nucleand inhibits cell growth", Mol Cell Biochem. (2003), 242(1-2): 35-38.

DeFamie et al. "Disruption of gap junctional intercellular communication by lindane is associated with aberrant localization of connexin43 and zonula occludens-1 in 42GPA9 Sertoli cells", Carcinogenesis (2001), 22: 1537-1542.

DeRossi et al. "The third helix of Antennapedia homeodomain translocates through biological membranes", J Biol. Chem. (1994), 269(14, Issue 8):10444-10450.

Dev, K.K. "Making protein interactions druggable: targeting PDZ domains", Nat Rev Drug Discov. (2004), 3(12): 1047-56.

Diegelmann and Evans. "Wound Healing: An Overview of Acute, Fibrotic and Delayed Healing",Frontiers Biosci. (2004), 9: 283-289.

Duffy et al. "Formation of the gap junction nexus: binding partners for connexins", J Physiol—Paris 96 (2002), pp. 243-249.

Duffy et al. "Regulation of connexin43 protein complexes by intracellular acidification", Circ. Res. (2004), 94: 215-222.

Dupont et al. "Altered connexin expression in human congestive heart failure", J. Mol Cell Cardiol (2002), 33: 359-371.

Elmquist et al. "VE-cadherin-derived cell-penetrating peptide, pVEC, with carrier functions", Exp. Cell Res. (2001), 269: 237-244.

Epstein, "Cutaneous Wound Healing", New. Engl. J. Med. (1999), 341(10): 738-746.

European Search Report, 7 pages, EP appl. No. 10185428.9 dated Dec. 27, 2011.

European Search Report, 9 pages, EP appl. No. 10185372.9 dated May 25, 2011.

(56) References Cited

OTHER PUBLICATIONS

European Search Report, 9 pages, EP appl. No. 10185398.4 dated Dec. 23, 2011.
Evans and Martin. "Gap junctions: structure and function", Mol Membr Biol (2002), 19: 121-136.
EyeSight.Org (FAQs; Eyesight.Org (Feb. 1, 2001), attached as pdf, 3 pages, also available at http://www.eyesight.org/Macular_Degeneration/FAQ/faq.html (last visited Apr. 27, 2015).
Fanning et al. "Isolation and functional characterization of the actin binding region in the tight junction protein ZO-1", Faseb J (2002), 16: 1835-1837.
Fawcett and Asher. "The glial scar and central nervosystem repair", Brain Res. Bull. (1999), 49:377-391.
Fischer et al. "Structure-activity relationship of truncated and substituted analogues of the intracellular delivery vector Penetratin", J. Pept. Res. (2000), 55: 163-172.
Fishman et al. "Expression of connexin43 in the developing rat heart", Circulation Research (1991), 68: 782-287.
Fonseca et al. "Upregulation in astrocytic connexin 43 gap junction levels may exacerbate generalized seizures in mesial temporal lobe epilepsy", Brain Research (2002), 1: 105-116.
Frankel and Pabo. "Cellular uptake of the Tat protein from human immunodeficiency Virus", Cell (1988), 55: 1189-1193.
Fromaget et al. "Changes in the expression of connexin 43, a cardiac gap junctional protein, during mouse heart development", J Mol Cell Cardiol. (1990), 22: 1245-1258.
Fromaget et al. "Distribution pattern of connexin 43, a gap junctional protein, during the differentiation of mouse heart myocytes", Differentiation (1992), 51: 9-20.
Fu et al. "CCN3 (NOV) interacts with Connexin43 in C6 glioma cells: possible mechanism of Connexin-mediated growth suppression", J Biol Chem. (2004), 279(35): 36943-36950 (2004).
Fujii et al. "A selective irreversible inhibitor targeting a PDZ protein interaction domain", J Am Chem Soc. (2003), 125(40): 12074-12075.
Gaietta et al. "Multicolor and electron microscopic imaging of connexin trafficking", Science (2002), 296: 503-507.
Gao et al. "A cell-penetrating peptide from a novel pVII-pIX phage-displayed random peptide library", Bioorg. Med. Chem. (2002), 10: 4057-4065.
Ghatnekar et al. "Connexin43 carboxyl-terminal peptides reduce scar progenitor and promote regenerative healing following skin wounding", Regen. Med. (2009), 4(2): 205-223.
Ghatnekar. "Technical Report", 7 pages (Jul. 17, 2012).
Giepmans and Moolenaar. "The gap junction protein connexin43 interacts with the second PDZ domain of the zona occludens-1 protein", Curr. Biol. (1998), 8(16): 931-934.
Giepmans et al. "Gap junction protein connexin-43 interacts directly with microtubules", Curr Biol (2001), 11: 1364-1368.
Giepmans, B.N. "Gap junctions and Connexin-interacting proteins", Cardiovasc Res. (2004), 62(2): 233-245.
Gil-Parrado et al. "Calpastatin exon 1 B-derived peptide, a selective inhibitor of calpain: enhancing cell permeability by conjugation with penetratin", Biol Chem (2003), 384: 395-402.
Gonzalez-Mariscal et al. "Tight junction proteins", Prog Biophys Mol Biol (2003), 81: 1-44.
Goodenough and Paul. "Beyond the gap: functions of unpaired connexon channels", Nat Rev Mol Cell Biol (2003), 4: 285-294.
Gourdie et al. "Gap junction distribution in adult mammalian myocardium revealed by an anti-peptide antibody and laser scanning confocal microscopy", Journal of Cell Science (1991), 99: 41-55.
Gourdie et al. NIH Grant 5R01HL056728 (Oct. 2011), 87 pages.
Gourdie et al. "The unstoppable connexin43 carboxyl-terminus: new roles in gap junction organization and wound Healing", Ann NY Acad Sci. (2006), 1080: 49-62.
Green and Loewenstein. "Autonomofunctional domains of chemically synthesized human immunodeficiency virtat trans-activator protein", Cell (1988), 55: 1179-1188.
Green et al. "Validation of immunohistochemical quantification in confocal scanning laser microscopy: a comparative assessment of gap junction size with confocal and ultrastructural techniques", Journal of Histochemistry and Cytochemistry (1993), 41: 1339-1349.
Gros et al. "Connexins in mammalian heart function", BioEssays (1996), 18: 719-730.
Gros et al. "Formation and growth of gap junctions in mouse myocardium during ontogenesis: a freeze-cleave study", J Cell Sci (1978), 30: 45-61.
Haddrill et al., "Understanding Age-Related Macular Degeneration," AllAboutVision.com, Mar. 2015, attached as PDF, 7 pages, also available at http://www.allaboutvision.com/conditions/amd.htm (last visited Apr. 21, 2015).
Hall and Gourdi. "Spatial organization of cardiac gap junctions can affect access resistance", Microsc Res Tech (1995), 31: 446-451.
Harris, A.L. "Emerging issues of connexin channels: biophysics fills the gap", Q Rev Biophys (2001), 34: 325-472.
Hawat et al. "Connexin 43 mimetic peptide Gap26 confers protection to intact heart against myocardial ischemia injury", Pflugers Arch.—Eur. J. Physiol. (2010), 460(3): 583-592.
Hayashi et al. "Cooperative effects of v-myc and c-Ha-ras oncogenes on gap junctional intercellular communication and tumorigenicity in rat liver epithelial cells", Cancer Lett. (1998), 128: 145-154.
Hayashi et al. "Inhibition of gap junctional intercellular communication in rat liver epithelial cells with transforming RNA", FEBS Lett. (2001), 491: 200-206.
Hayashi et al. "Stimulation of cell proliferation and inhibition of gap junctional intercellular communication by linoleic acid", Cancer Lett. (1997), 112: 103-111.
Hodgins, "Connecting wounds with Connexins", J. Invest. Derm. (2004), 122: ix-x.
Hong and Clayman. "Isolation of a peptide for targeted drug delivery into human head and neck solid tumors", Cancer Res. (2000), 60: 6551-6556.
Hunter et al. "Fusion of GFP to the carboxyl terminof connexin43 increases gap junction size in HeLa cells", Cell Commun Adhes. (2003), 10(4-6): 211-214.
Hunter et al. "Zonula occludens-1 alters connexin43 gap junction size and organization by influencing channel accretion", Mol Biol Cell. (2005), 16: 5686-98. Epub Sep. 29, 2005.
Hutchinson and Hayden. "The prediction of exons through an analysis of spliceable open reading frames", Nucl. Acids Res. (1992), 20(13): 3453-3462.
Hutnik et al. "The Protective Effect of Functional Connexin43 Channels on a Human Epithelial Cell Line Exposed to Oxidative Stress", Invest. Ophthalmol. Visual Sci. (2008), 49(2): 800-806.
International Search Report, 4 pages, PCT appl. No. PCT/US2005/046442 (dated Mar. 26, 2007).
International Search Report and Writen Opinion, PCT/US08/67944, dated Dec. 12, 2008.
Itoh et al. "Involvement of ZO-1 in cad herin-based cell adhesion through its direct binding to alpha catenin and actin filaments", J Cell Biol (1997), 138: 181-192.
Jin and Lau. "Identification of connexin-interacting proteins: application of the yeast two-hybrid screen", Methods (2000), 20: 219-231.
Johnson et al. "Gap junctions assemble in the presence of cytoskeletal inhibitors, but enhanced assembly requires microtubules", Experimental Cell Research (2002), 275: 67-80.
Jordan et al. "Trafficking, assembly, and function of a connexin43-green fluorescent protein chimera in live mammalian cells", Mol Biol Cell (1999), 10: 2033-2050.
Kajstura et al. "Bone marrow cells differentiate in cardiac cell lineages after infarction independently of cell fusion", Circ Res. (2005), 96(1):127-37.
Kanovsky et al. "Peptides from the amino terminal mdm-2-binding domain of p53, designed from conformational analysis, are selectively cytotoxic to transformed cells", Proc Natl Acad Sci USA (2001), 98: 12438-12443.

(56) References Cited

OTHER PUBLICATIONS

Kaprielian et al. "Downregulation of immunodetectable connexin43 and decreased gap junction size in the pathogenesis of chronic hibernation in the human left ventricle", Circulation (1998), 97: 651-660.
Karmel et al., "Dry AMD: Hope is in the Pipline," AAO.org, Apr. 2008, also available at http://www.aao.org/publications/eyenet/200804/retina.cfm?RenderForPrint=1 & (past visited Apr. 20, 2015).
Kausalya et al. "Association of ARVCF with zonula occludens (ZO)-1 and ZO-2: binding to PDZ-domain proteins and cell-cell adhesion regulate plasma membrane and nuclear localization of ARVCF", Mol Biol Cell. (2004), 15(12): 5503-5515. Epub Sep. 29, 2004.
Kausalya et al. "Connexin45 directly binds to ZO-1 and localizes to the tight junction region in epithelial MDCK cells", FEBS Letters (2001), 505: 92-96.
Kumar and Gilula. "The gap junction communication channel", Cell (1996), 84: 381-388.
Kwak et al. "Inhibition of endothelial wound repair by dominant negative connexin inhibitors", Mol Biol Cell. (2001), 12(4): 831-845.
Laing et al. "Connexin45 interacts with zonula occludens-1 and connexin43 in osteoblastic cells", J Biol Chem (2001), 276: 23051-23055.
Laird et al. "Expression and imaging of connexin-GFP chimeras in live mammalian cells", Methods Mol Biol (2001), 154: 135-142.
Lampe and Lau. "Regulation of gap junctions by phosphorylation of connexins", Arch Biochem Biophys (2000), 384: 205-215.
Lauf et al. "Dynamic trafficking and delivery of connexons to the plasma membrane and accretion to gap junctions in living cells", Proc Natl Acad Sci USA (2002), 99: 10446-10451.
Lauf et al. "Expression of fluorescently tagged connexins: a novel approach to rescue function of oligomeric DsRed-tagged proteins", FEBS Lett (2001), 498: 11-15.
Legato, M.J. "Cellular Mechanisms of Normal Growth in the Mammalian Heart I. Qualitative and Quantitative Features of Ventricular Architecture in the Dog from Birth to Five Months of Age", Circulation Research (1979), 44: 250-262.
Li et al. "Neuronal connexin36 association with zonula occludens-1 protein (ZO-1) in mouse brain and interaction with the first PDZ domain of ZO-1", Eur J Neurosci. (2004), 19(8): 2132-2146.
Lin et al. "Inhibition of nuclear translocation of transcription factor NF-KB by a synthetic peptide containing a cell membranepermeable motif and nuclear localization sequence", J. Biol. Chem. (1995), 270: 14255-14258.
Liu et al. "A structural basis for the unequal sensitivity of the major cardiac and liver gap junctions to intracellular acidification: the carboxyl tail length", Biophys J (1993), 64: 1422-1433.
Livingstone & Barton, "Protein sequence alignments: a strategy for the hierarchical analysis of residue conservation," CABIOS, vol. 9(6):745-756 (1993).
Lo, C.W. Role of gap junctions in cardiac conduction and development: insights from the connexin knockout mice. Circulation Research (2000), 87: 346-348.
Lofgren, "Leg ulcers. Symptoms of an underlying disorder," Postgrad Med., vol. 76(4):51-54 (Sep. 15, 1984; abstract only).
Lundberg et al. "Cell membrane translocation of the N-terminal (1-28) part of the prion protein", Biochem. Biophys. Res. Commun. (2002), 299: 85-90.
MacRedmond, "Treatment of persistent dry cough: if possible, treat the cause; if not, treat the cough," Monaldi Arch Chest Dis., vol. 54(3):269-74 (Jun. 1999; abstract only).
Mambettsaeva et al. "Expiression of Three Functional Domains of Connexin 32 as Thioredoxin Fusion Proteins in *Escherichia coli* and Generation of Antibodies",Prot. Express. Purif. (1997), 11: 26-34.
Mansour, "Ocular manifestations of various systemic disorders," Current Opinion in Ophthalmology (1994), vol. 5; VI:1 05-109.
Martin, P. "Wound healing—aiming for perfect skin regeneration", Science (1997), 276(5309): 75-81.

Matsushita et al. "Photo-acceleration of protein release from endosome in the protein transduction system", FEBS Lett. (2004), 572: 221-226.
Merrifield et al. "Endocytic vesicles move at the tips of actin tails in cultured mast cells", Nat Cell Biol (1999), 1: 72-74.
Mitic and Anderson. "Molecular architecture of tight junctions", Annu Rev Physiol (1998), 60: 121-142.
Moorby, C.D. "A connexin 43 mutant lacking the carboxyl cytoplasmic domain inhibits both growth and motility of mouse 3T3 fibroblasts", Mol Carcinog. (2000), 28(1):23-30.
Morris et al. "A peptide carrier for the delivery of bioloically active proteins into mammalian cells", Nature Biotechnol. (2001), 19: 1173-1176.
Moyer et al. "Wound healing: the role of gap junctional communication in rat granulation tissue maturation", Exp. Mol. Pathol. (2002), 72: 10-16.
Murray et al. "Relationship of cytoskeletal filaments to annular gap junction expression in human adrenal cortical tumor cells in culture", Exp Cell Res (1997), 234: 398-404.
Musil and Goodenough. "Biochemical analysis of connexin43 intracellular transport, phosphorylation, and assembly into gap junctional plaques", J Cell Biol (1991), 115: 1357-1374.
Nielsen et al. "Lens connexins alpha3Cx46 and alpha8Cx50 interact with zonula occludens protein-1 (ZO-1)", Mol Biol Cell. (2003), 14(6):2470-2481. Epub Mar. 7, 2003.
Norenberg, M.D. "Astrocyte responses to CNS injury", J. Neuropathol. Exp. Neurol. (1994), 53: 213-220.
Oehlke et al. "Cellular uptake of an a-helical amphipathic model peptide with the potential to deliver polar compounds into the cell interior non-endocytically", Biochim. Biophys. Acta. (1998), 1414: 127-139.
Orlandini and Margaria. "Evaluation of the efficiency of a new hollow fiber plasmapheresis filter", Int J Artif Organs (1983), 6(Suppl 1): 103-106.
Park et al. "Structure-activity analysis of buforin II, a histone H2A-derived antimicrobial peptide: the proline hinge is responsible for the cell-penetrating ability of buforin II", Proc. Natl Acad. Sci. USA (2000), 97: 8245-8250.
Partial European Search Report, 5 pages, EP appl. No. 10185428.9 (dated Sep. 6, 2011).
Partial European Search Report, 6 pages, EP appl. No. 10185372.9 (dated Jan. 21, 2011).
Partial European Search Report, 7 pages, EP appl. No. 10185398.4 (dated Sep. 6, 2011).
Patel et. al., "Ocular Manifestations of Autoimmune Disease," American Family Physician (Sep. 15, 2002), vol. 66(6):991-998.
Pooga et al. "Cell penetration by transportan", FASEB J. (1998), 12: 67-77 (1998).
Poss et al. "Heart regeneration in zebrafish", Science (2002), 298(5601): 2188-2190 (2002).
Prochiantz, A. "Homeodomain-derived peptides. In and out of the cells", Ann NY Acad Sci (1999), 886: 172-179.
Qiu et al. "Targeting connexin43 expression accelerates the rate of wound repair", Curr Biol. (2003), 13(19): 1697-703.
Rousseau, "Hiccups," South Med. J., vol. 88(2):175-81 (Feb. 1995, abstract only).
Rousselle et al. "New advances in the transport of doxorubicin through the blood-brain barrier by a peptide vector-mediated strategy", Mol. Pharmacol. (2000), 57(4): 679-686.
Saint-Geniez et al., "Endogenous VEGF Is Required for Visual Function: Evidence for a Survival Role on Muller Cells and Photoreceptors," PLoS ONE 3(11 ): e3554.doi:1 0.1371 /journal.pone.0003554 (Nov. 3, 2008).
Saitongdee et al. "Increased connexin43 gap junction protein in hamster cardiomyocytes during cold acclimatization and hibernation", Cardiovasc Res (2000), 47: 108-115.
Sawada et al. "Cytoprote.ctive membrane-permeable peptides designed from the Bax-binding domain of Ku70", Nature Cell Biol. (2003), 5: 352-357.
Segretain and Falk. "Regulation of connexin biosynthesis, assembly, gap junction formation, and removal", Bioch. Bioph. Acta (2004), 1662: 3-21.

(56) References Cited

OTHER PUBLICATIONS

Segretain et al. "A proposed role for ZO-1 in targeting connexin 43 gap junctions to the endocytic pathway", Biochimie. (2004), 86: 241-244.
Sepp et al. "Altered patterns of cardiac intercellular junction distribution in hypertrophic cardiomyopathy", Heart (1996), 76: 412-417.
Severs et al. "Remodelling of gap junctions and connexin expression in heart disease", Biochim Biophys Acta. (2004), 1662: 138-148.
Shibata et al. "Ultrastructual changes during development of gap junctions in rabbit left ventricular myocardial cells", Journal of Ultrastructure Research (1980), 71: 258-271.
Silver and Miller. "Regeneration beyond the glial scar", Nat Rev Neurosci. (2004), 5(2): 146-156.
Simpson et al. "Modulation of cardiac myocyte phenotype in vitro by the composition and orientation of the extracellular matrix", Journal of Cellular Physiology (1994), 161: 89-105.
Smith et al. "Altered patterns of gap junction distribution in ischemic heart disease. An immunohistochemical study of human myocardium using laser scanning confocal microscopy", American Journal of Pathology (1991), 139: 801-821.
Songyang et al. "Recognition of unique carboxyl-terminal motifs by distinct PDZ domains", Science (1997), 275: 73-77.
Spach, M.S. "Transition from a continuoto discontinuounderstanding of cardiac conduction", Circ Res. (2003), 92(2): 125-126.
Stergiopoulos et al. "Hetero-Domain Interactions as a Mechanism for the Regulation of Connexin Channels", Circ. Res. (1999), 84:1144-1155.
Stevenson et al. "Identification of ZO-1: a high molecular weight polypeptide associated with the tight junction (zonula occludens) in a variety of epithelia", J Cell Biol (1986), 103: 755-766.
Sullivan and Lo. "Expression of a connexin 43/beta-galactosidase fusion protein inhibits gap junctional communication in NIH3T3 cells", J Cell Biol. (1995), 130(2): 419-429.
Supplementary European Search Report, 9 pages, EP appl. No. 08771766.6 (dated Jul. 4, 2012).
Thomas et al. "Role of cytoskeletal elements in the recruitment of Cx43-GFP and Cx26-YFP into gap junctions", Cell Commun Adhes (2001), 8: 231-236.
Toyofuku et al. "c-Src regulates the interaction between connexin-43 and ZO-1 in cardiac myocytes", J Biol Chem. (2001), 276(3): 1780-1788. Epub Oct. 16, 2000.
Toyofuku et al. "Direct association of the gap junction protein connexin-43 with ZO-1 in cardiac myocytes", J Biol Chem. (1998), 273(21): 12725-12731.
Traub et al. "Characterization of the gap junction protein connexin37 in murine endothelium, respiratory epithelium, and after transfection in human HeLa cells", Eur. J. Cell Biol. (1998), 77: 313-322.
Tsao et al. "A diploid epithelial cell line from normal adult rat liver with phenotypic properties of 'oval' cells", Exp. Cell Res. (1984), 154:38-52.
UniProtKB/Swiss-Prot P17302, downloaded Mar. 11, 2010, 16 pages. http://www.uniprot.org/uniprot/P17302.html.
Vigneron et al. "Guanidinium-cholesterol cationic lipids: Efficient vectors for the transfection of eukaryotic cells", Proc. Natl. Acad. Sci. USA. (1998), 93: 9682-9686.
Wadia et al. "Transducible TAT-HA fusogenic peptide enhances escape of TAT-fusion proteins after lipid raft macropinocytosis", Nat Med. (2004), 10(3): 310-315.
Wender et al. "The design, synthesis, and evaluation of molecules that enable or enhance cellular uptake: Peptoid molecular transporters", Proc. Natl. Acad. Sci. USA (2000), 97(24): 13003-13008.
Wilgus et al. "Reduction of scar formation in full-thickness wounds with topical celecoxib treatment", Wound Rep Reg (2003), 11: 25-34.
Willecke et al. "Mouse Connexin37: Cloning and Functional Expression of a Gap Junction Gene Highly Expressed in Lung", J. Cell Biol. (1991), 114(5): 1049-1057.
Written Opinion of the International Searching Authority, 7 pages, PCT appl. No. PCT/US2005/046442 (dated Mar. 26, 2007).
Yoo, D.S. "The dielectric properties of cancerous tissues in a nude mouse xenograft model.", Bioelectromagnetics (2004), 25(7): 492-497.
Zarbin. "Current Concepts in the Pathogenesis of Age-Related Macular Degeneration",Arch. Ophthalmol. (2004), 122(4):598-614.
Zhang et al., "The Gap Junction-independent Tumor-suppressing Effect of Connexin 43", J. Biol. Chem. (2003), 278(45): 44852-44856.
Zhu et al. "Quantitative Analysis of ZO-1 Co-Localization with Cx43 Gap Junction Plaques in Cultures of Rat Neonatal Cardiomyocytes", Microsc Microanal. (2005), 11(3): 244-248.
Zhu et al., "Stabilization of Gap and Tight Junctions with ACT1 Reduces Post Transplantation Ischemia Reperfusion Injury" American Society of Transplant Surgeons, Winter Meeting, Jan. 15-18, 2015. Poster with Abstract.

\* cited by examiner

FIG. 5A
FIG. 5B
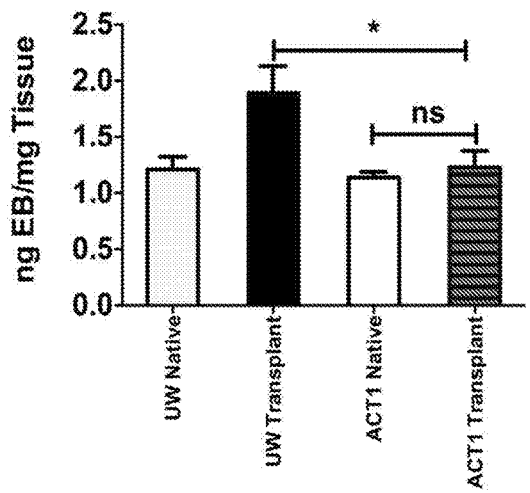
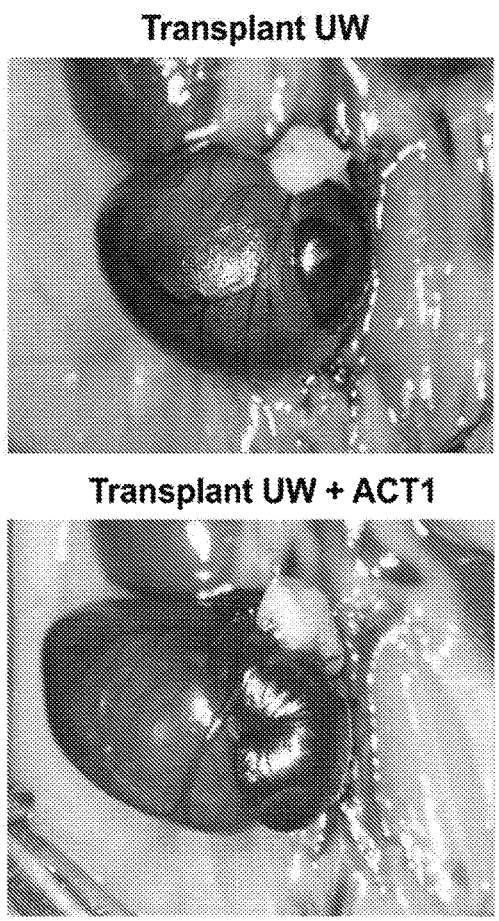
Transplant UW
Transplant UW + ACT1

ALPHA CONNEXIN C-TERMINAL (ACT) PEPTIDES AND METHODS OF USE THEREOF

CROSS-REFERENCE TO RELATED APPLICATIONS

This application is a continuation of U.S. application Ser. No. 15/195,569, filed Jun. 28, 2016, now U.S. Pat. No. 9,844,214, which is a continuation of U.S. application Ser. No. 14/932,630, filed Nov. 4, 2015, now U.S. Pat. No. 9,408,381, issued Aug. 9, 2016, which is a continuation of U.S. application Ser. No. 13/935,848, filed Jul. 5, 2013, which is a continuation-in-part of U.S. application Ser. No. 13/842,506, filed Mar. 15, 2013, now U.S. Pat. No. 8,916,515, issued Dec. 23, 2014, which is a continuation of U.S. application Ser. No. 13/715,626, filed Dec. 14, 2012, now U.S. Pat. No. 8,809,257, issued Aug. 19, 2014, which is a continuation of U.S. application Ser. No. 12/871,461, filed Aug. 30, 2010, now U.S. Pat. No. 8,357,668, issued Jan. 22, 2013, which is a divisional of U.S. application Ser. No. 11/721,529, filed Jun. 12, 2007, now U.S. Pat. No. 7,786,074, issued Aug. 31, 2010, which is the U.S. National Phase of International Application No. PCT/US2005/046442, filed Dec. 20, 2005, which claims benefit of U.S. Provisional Application No. 60/638,366, filed Dec. 21, 2004 and U.S. Provisional Application No. 60/671,796, filed Apr. 15, 2005 and said U.S. application Ser. No. 13/935,848, filed Jul. 5, 2013, is a continuation of U.S. application Ser. No. 12/665,596, filed Jul. 21, 2010, which is the U.S. National Phase of International Application No. PCT/US2008/067944, filed Jun. 23, 2008, which claims the benefit of U.S. Provisional Application No. 60/945,493, filed Jun. 21, 2007; each of which are hereby incorporated herein by reference in their entireties.

STATEMENT REGARDING FEDERALLY SPONSORED RESEARCH

This invention was made with government support under Grant EY13520 awarded by the National Institutes of Health. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: FIRS_002_05US.SeqList, date recorded Nov. 13, 2017, file size 32 kilobytes).

BACKGROUND

Macular degeneration is a medical condition predominantly found in elderly adults in which the center of the inner lining of the eye, known as the macula area of the retina, suffers thinning, atrophy, and in some cases bleeding. This can result in loss of central vision, which entails inability to see fine details, to read, or to recognize faces. According to the American Academy of Ophthalmology, it is the leading cause of central vision loss (blindness) and in the United States for those over the age of fifty years. Although some macular dystrophies that affect younger individuals are sometimes referred to as macular degeneration, the term generally refers to age-related macular degeneration (AMD).

Advanced AMD, which is responsible for profound vision loss, has two forms: dry and wet. Central geographic atrophy, the dry form of advanced AMD, results from atrophy to the retinal pigment epithelial layer below the retina, which causes vision loss through loss of photoreceptors (rods and cones) in the central part of the eye. While no treatment is currently available for this condition, vitamin supplements with high doses of antioxidants, Lutein and Zeaxanthin, have been demonstrated by the National Eye Institute and others to slow the progression of dry macular degeneration and in some patients, improve visual acuity.

Neovascular or exudative AMD, the wet form of advanced AMD, causes vision loss due to abnormal blood vessel growth in the choriocapillaries, through Bruch's membrane, ultimately leading to blood and protein leakage below the macula. Bleeding, leaking, and scarring from these blood vessels eventually cause irreversible damage to the photoreceptors and rapid vision loss if left untreated.

Until recently, no effective treatments were known for wet macular degeneration. However, anti-VEGF (anti-Vascular Endothelial Growth Factor) agents, when injected directly into the vitreous humor of the eye using a small, painless needle, can cause contraction of the abnormal blood vessels and improvement of vision. The injections frequently have to be repeated on a monthly or bi-monthly basis. Examples of these agents include Lucentis, Avastin and Macugen. Only Lucentis and Macugen are FDA approved as of April 2007, and only Lucentis and Avastin appear to be able to improve vision, but the improvements are slight and do not restore full vision. Thus, needed in the art are compositions and methods treat or prevent macular degeneration.

Organ transplant has become an established technique for treatment of various diseases and disorders. However, the decrease in viability of the organ after removal from the donor is a significant limiting factor to the success of organ transplants. Generally, organs are preserved after removal from the donor by hypothermic storage and continuous perfusion. Hypothermic storage generally means rapid cooling of the organ to a temperature between 0° and 4° C., and decreases the rate at which intracellular enzymes degrade. However, injury to the organ occurs through damage to epithelial and endothelial cells, during cold storage and upon reperfusion with a warm reperfusion solution upon transplant into the recipient. Such ischemia reperfusion injury to organs commonly leads to delayed or diminished organ function, and predisposes the organ to rejection. Therefore, there is a need in the art for improved methods of preservation of organs, to extend the viability of the organ and to improve organ function following transplant.

BRIEF SUMMARY

In accordance with the purpose of this invention, as embodied and broadly described herein, this invention relates to methods of treating or preventing macular degeneration, and methods and compositions for preserving organs or tissues for organ or tissue transplantation.

In one aspect, the present disclosure provides methods and compositions for preserving organs or tissues for organ transplantation or tissue transplantation, comprising incubating the organ or tissue with a solution comprising an isolated polypeptide comprising the carboxy-terminal amino acid sequence of an alpha connexin, or a conservative variant thereof. In some embodiments, the organ is perfused with the compositions provided herein following removal from the donor.

In one embodiment, the organ is a kidney. In another embodiment, the organ is a heart. In another embodiment, the organ is a liver. In another embodiment, the organ is a lung. In another embodiment, the organ is an intestine. In yet another embodiment, the organ is pancreas. In still another embodiment, the organ is a thymus.

In one embodiment, the polypeptide inhibits cellular injury in the organs. In one embodiment, the polypeptide inhibits endothelial cellular injury. In another embodiment, the polypeptide inhibits epithelial cellular injury. In one aspect, the cellular injury is caused by cold preservation induced damage. In another aspect, the cellular injury is caused by hypoxia.

In one aspect, the cellular injury is ischemia reperfusion injury (IRI). In another aspect, the cellular injury is ischemic reperfusion induced graft injury.

In one embodiment, the polypeptide promotes cell-cell communication. In another embodiment, the polypeptide stabilizes gap junctions in cells. In yet another embodiment, the polypeptide stabilizes tight junctions in cells. In one embodiment, the polypeptide mitigates hemichannel activity in cells. In one embodiment, the polypeptide inhibits apoptosis in cells. In another embodiment, the polypeptide inhibits mitochondrial oxidant production. In another embodiment, the polypeptide promotes the integrity of endothelial cells. In another embodiment, the polypeptide promotes barrier function of endothelial cells. In some embodiments, the cells are the cells of an organ for transplantation from a donor to a recipient.

In one embodiment, the polypeptide inhibits post transplantation IRI by inhibiting post transplantation inflammation. In one embodiment, the polypeptide preserves organs by inhibiting pro-inflammatory cytokine release from cells in the organs. In one aspect, the pro-inflammatory cytokine is IL-8.

In one embodiment, the polypeptide comprises the amino acid sequence selected from the group consisting of SEQ ID NO: 1, SEQ ID NO: 2, SEQ ID NO: 3, SEQ ID NO: 4, and SEQ ID NO: 5. In another embodiment, the polypeptide comprises the amino acid sequence of SEQ ID NO: 2. In another embodiment, the polypeptide comprises an amino acid sequence with at least 65% sequence identity to the c-terminal most 9 amino acids of SEQ ID NO: 1.

In one embodiment, the polypeptide comprises from about 4 to about 30 contiguous amino acids of the carboxy-terminus of the alpha connexin. In one embodiment, the alpha connexin is selected from a group consisting of connexin 30.2, connexin 31.9, connexin 33, connexin 35, connexin 36, connexin 37, connexin 38, connexin 39, connexin 39.9, connexin 40, connexin 40.1, connexin 43, connexin 43.4, connexin 44, connexin 44.2, connexin 44.1, connexin 45, connexin 46, connexin 46.6, connexin 47, connexin 49, connexin 50, connexin 56, and connexin 59. In another embodiment, the alpha connexin is connexin 37, connexin 40, connexin 43, or connexin 45.

In one embodiment, the polypeptide comprises from about 5 to about 19 contiguous amino acids of the carboxy-terminus of the alpha connexin. In another embodiment, the polypeptide comprises a deletion of one amino acid from the carboxy-terminal amino acid sequence.

In one embodiment, the present disclosure provides methods and compositions for inhibiting cellular injury in a subject, comprising administering to the subject an isolated polypeptide comprising the carboxy-terminal amino acid sequence of an alpha connexin, or a conservative variant thereof. In one embodiment, the cellular injury is an endothelial cellular injury. In another embodiment, the cellular injury is an epithelial cellular injury. In one embodiment, the cellular injury is a post transplantation IRI. In one aspect, the polypeptide inhibits post transplantation IRI by inhibiting endothelial permeability. In another aspect, the polypeptide inhibits post transplantation IRI by inhibiting heart graft injury.

In one aspect, the present disclosure provides compositions comprising an organ preservation solution and a polypeptide comprising the carboxy-terminus of an alpha connexin, or a conservative variant thereof. In some embodiments, the polypeptide comprises from about 4 to about 30 contiguous amino acids of the carboxy-terminus of the alpha connexin. In further embodiments, the polypeptide comprises a sequence selected from the group consisting of SEQ ID NOs: 1, 2, 3, 4, and 5. In another aspect, the present disclosure provides compositions comprising one or more organs for transplant and a polypeptide comprising the carboxy-terminus of an alpha connexin, or a conservative variant thereof, as provided herein. In some embodiments, the composition comprises one or more organs for transplant and an organ preservation solution comprising an alpha connexin polypeptide provided herein.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 5A-5B show heart graft Evan's Blue uptake post transplantation. Hearts were stored in UW±ACT1 peptide for 6 h prior to transplantation. Following implantation, Evan's Blue dye was injected immediately post reperfusion and organs harvested 30 mins later. Evan's Blue dye uptake was quantified (5A) and showed that ACT1 treatments significantly reduced endothelial permeability (n=6 *p<0.02). (5B) Representative macroscopic images taken 30 mins post reperfusion. Note the increased uptake of Evan's Blue dye in UW stored hearts as compared to UW+ACT1 peptide.

DETAILED DESCRIPTION

Figure 1:
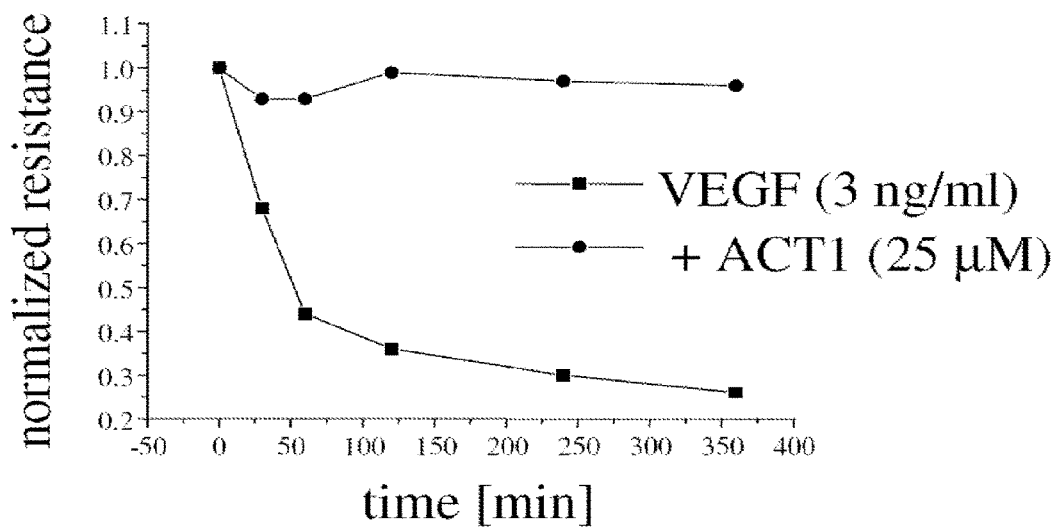
FIG. 1 shows the alpha connexin carboxy-terminal (ACT) polypeptide ACT1 prevents VEGF-induced deterioration of TER in ARPE-19 cells. Trans-epithelial resistance (TER) measurements, using ARPE19 cell (immortalized human RPE cells) monolayers revealed that VEGF leads to rapid deterioration, which was blocked by pretreating the cells with the ACT peptide.

Provided herein are compositions and methods for treating or preventing pathologies involving epithelial permeablization and/or neovascularization, comprising administering to the subject a polypeptide comprising a carboxy-terminal amino acid sequence of an alpha Connexin (also referred to herein as an alpha Connexin carboxy-Terminal (ACT) polypeptide), or a conservative variant thereof.

For example, provided are compositions and methods for treating or preventing macular degeneration in a subject, comprising administering to the subject a polypeptide comprising a carboxy-terminal amino acid sequence of an alpha Connexin (also referred to herein as an alpha Connexin carboxy-Terminal (ACT) polypeptide), or a conservative variant thereof.

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the peptide are discussed, each and every combination and permutation of peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

A. Compositions

Disclosed for use in the disclosed method is an isolated polypeptide comprising a carboxy-terminal amino acid sequence of an alpha Connexin (also referred to herein as an alpha Connexin carboxy-Terminal (ACT) polypeptide), or a conservative variant thereof. The ACT polypeptides of the provided method are disclosed in International Patent Publication WO/2006/069181, which is incorporated by reference herein in its entirety for the teaching of these peptides.

It is to be understood that the disclosed compositions and methods are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

A variety of sequences are provided herein and these and others can be found in Genbank at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

In some aspects, the herein polypeptide of the disclosed methods can be any polypeptide comprising the carboxy-terminal most amino acids of an alpha Connexin.

In some aspects, the polypeptide does not comprise the full-length alpha Connexin protein. Thus, in some aspects, the provided polypeptide does not comprise the cytoplasmic N-terminal domain of the alpha Connexin. In some aspects, the provided polypeptide does not comprise the two extracellular domains of the alpha Connexin. In some aspects, the provided polypeptide does not comprise the four transmembrane domains of the alpha Connexin. In some aspects, the provided polypeptide does not comprise the cytoplasmic loop domain of the alpha Connexin. In some aspects, the provided polypeptide does not comprise that part of the sequence of the cytoplasmic carboxyl terminal domain of the alpha Connexin proximal to the fourth transmembrane domain. There is a conserved proline or glycine residue in alpha Connexins consistently positioned some 17 to 30 amino acids from the carboxyl terminal-most amino acid (Table 2). For example, for human Cx43 a proline residue at amino acid 363 is positioned 19 amino acids back from the carboxyl terminal most isoleucine. In another example, for chick Cx43 a praline residue at amino acid 362 is positioned 18 amino acids back from the carboxyl terminal-most isoleucine. In another example, for human Cx45 a glycine residue at amino acid 377 is positioned 19 amino acids back from the carboxyl terminal most isoleucine. In another example for rat Cx33, a praline residue at amino acid 258 is positioned 28 amino acids back from the carboxyl terminal most methionine. Thus, in some aspects, the provided polypeptide does not comprise amino acids proximal to said conserved proline or glycine residue of the alpha Connexin. Thus, the provided polypeptide can comprise the c-terminal-most 4 to 30 amino acids of the alpha Connexin, including the c-terminal most 4, 5, 6, 7, 8, 9, 10, 11, 12, 13, 14, 15, 16, 17, 18, 19, 20, 21, 22, 23, 24, 25, 26, 27, 28, 29, 30 amino acids of the alpha Connexin.

In some aspects, the provided polypeptide further comprises a deletion of one or more amino acids of the c-terminal-most 4 to 30 amino acids of the alpha Connexin, including a deletion of 1, 2, 3, 4, 5, 6, 7, 8, 9, or 10 amino acids of the c-terminal-most 4 to 30 amino acids of the alpha Connexin. For example, in some aspects, the provided polypeptide does not comprise the c-terminal-most 1, 2, or 3 amino acids of the alpha Connexin. For example, the provided polypeptide can consist essentially of the amino acid sequence SEQ ID NO:92, or a carboxy terminal fragment thereof of at least 4, 5, 6, 7, 8, 9, 10 amino acids in length.

The carboxy-terminal most amino acids of an alpha Connexin in the provided peptides can be flanked by non-alpha Connexin or non-ACT peptide Connexin amino acids. Examples of the flanking non-alpha Connexin and non-ACT Connexin amino acids are provided herein. An example of non-ACT Connexin amino acids are the carboxy-terminal 21 to 120 amino acids of human Cx43 (SEQ ID NO: 71). Another example would be the carboxy-terminal 21 to 120 amino acids of chick Cx43 (SEQ ID NO: 72). Another example would be the carboxy-terminal 20 to 120 amino acids of human Cx45 (SEQ ID NO: 73). Another example would be the carboxy-terminal 21 to 120 amino acids of chick Cx45 (SEQ ID NO: 74). Another example would be the carboxy-terminal 21 to 120 amino of human Cx37 (SEQ ID NO: 75). Another example would be the carboxy-terminal 21 to 120 amino acids of rat Cx33 (SEQ ID NO: 76). By "carboxy-terminal 21 to 120 amino acids" is meant the up to 120 c-terminal amino acids of the Connexin but not including the c-terminal-most 20 amino acids.

An example of a non-alpha Connexin is the 239 amino acid sequence of enhanced green fluorescent protein (SEQ ID NO: 77). In some aspects, given that ACT1 is shown to be functional when fused to the carboxy terminus of the 239 amino acid sequence of GFP, ACT peptides are expected to retain function when flanked with non-Connexin polypeptides of up to at least 239 amino acids. Indeed, as long as the ACT sequence is maintained as the free carboxy terminus of a given polypeptide, and the ACT peptide is able to access its targets. Thus, polypeptides exceeding 239 amino acids in addition to the ACT peptide can function in treating or preventing pathologies involving epithelial permeablization and/or neovascularization.

Connexins are the sub-unit protein of the hemichannel and the gap junction channel, which are responsible for intercellular communication (Goodenough and Paul, 2003). Thus, various cells are able to communicate with each other and with the extracellular environment through hemichannels and gap junctions formed by the protein connexin. Six connexin proteins make up one hemichannel, and 2 hemichannels make up 1 gap junction channel. Gap junctions are a cluster of channels that are located in the plasma membrane between adjoining cells and they mediate intercellular communication. Hemichannels are a separate entity from gap junction channels. Hemichannels permit the exchange of molecules between the intracellular compartments and the extracellular environment.

Based on patterns of conservation of nucleotide sequence, the genes encoding Connexin proteins are divided into two families termed the alpha and beta Connexin genes. The carboxy-terminal-most amino acid sequences of alpha Connexins are characterized by multiple distinctive and conserved features (see Table 2). This conservation of organization is consistent with the ability of ACT peptides to form distinctive 3D structures, interact with multiple partnering proteins, mediate interactions with lipids and membranes, interact with nucleic acids including DNA, transit and/or block membrane channels and provide consensus motifs for proteolytic cleavage, protein cross-linking, ADP-ribosylation, glycosylation and phosphorylation. Thus, the provided polypeptide interacts with a domain of a protein that normally mediates the binding of said protein to the carboxy-terminus of an alpha Connexin. For example, nephroblastoma overexpressed protein (NOV) interacts with a Cx43 c-terminal domain (Fu et al., J Biol Chem. 2004 279(35):36943-50). It is considered that this and other proteins interact with the carboxy-terminus of alpha Connexins and further interact with other proteins forming a macromolecular complex. Thus, the provided polypeptide can inhibit the operation of a molecular machine, such as, for example, one involved in regulating the aggregation of Cx43 gap junction channels.

As used herein, "inhibit," "inhibiting," and "inhibition" mean to decrease an activity, response, condition, disease, or other biological parameter. This can include, but is not limited to, the complete loss of activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The ACT sequence of the provided polypeptide can be from any alpha Connexin. Thus, the alpha Connexin component of the provided polypeptide can be from a human, murine, bovine, monotrene, marsupial, primate, rodent, cetacean, mammalian, avian, reptilian, amphibian, piscine, chordate, protochordate or other alpha Connexin.

Thus, the provided polypeptide can comprise an ACT of a Connexin selected from the group consisting of mouse Connexin 47, human Connexin 47, Human Connexin 46.6, Cow Connexin 46.6, Mouse Connexin 30.2, Rat Connexin 30.2, Human Connexin 31.9, Dog Connexin 31.9, Sheep Connexin 44, Cow Connexin 44, Rat Connexin 33, Mouse Connexin 33, Human Connexin 36, mouse Connexin 36, rat Connexin 36, dog Connexin 36, chick Connexin 36, zebrafish Connexin 36, morone Connexin 35, morone Connexin 35, *Cynops* Connexin 35, *Tetraodon* Connexin 36, human Connexin 37, chimp Connexin 37, dog Connexin 37, *Cricetulus* Connexin 37, Mouse Connexin 37, *Mesocricetus* Connexin 37, Rat Connexin 37, mouse Connexin 39, rat Connexin 39, human Connexin 40.1, *Xenopus* Connexin 38, Zebrafish Connexin 39.9, Human Connexin 40, Chimp Connexin 40, dog Connexin 40, cow Connexin 40, mouse Connexin 40, rat Connexin 40, *Cricetulus* Connexin 40, Chick Connexin 40, human Cormexin 43, *Cercopithecus* Connexin 43, *Oryctolagus* Cormexin 43, *Spermophilus* Connexin 43, *Cricetulus* Connexin 43, *Phodopus* Connexin 43, Rat Connexin 43, *Sus* Connexin 43, *Mesocricetus* Connexin 43, Mouse Connexin 43, *Cavia* Connexin 43, Cow Connexin 43, *Erinaceus* Connexin 43, Chick Connexin 43, *Xenopus* Connexin 43, *Oryctolagus* Connexin 43, *Cyprinus* Connexin 43, Zebrafish Connexin 43, *Danio aequipinnatus* Connexin 43, Zebrafish Connexin 43.4, Zebrafish Connexin 44.2, Zebrafish Connexin 44.1, human Connexin 45, chimp Connexin 45, dog Connexin 45, mouse Connexin 45, cow Connexin 45, rat Connexin 45, chick Connexin 45, *Tetraodon* Connexin 45, chick Connexin 45, human Connexin 46, chimp Connexin 46, mouse Connexin 46, dog Connexin 46, rat Connexin 46, *Mesocricetus* Connexin 46, *Cricetulus* Connexin 46, Chick Connexin 56, Zebrafish Connexin 39.9, cow Connexin 49, human Connexin 50, chimp Connexin 50, rat Connexin 50, mouse Connexin 50, dog Connexin 50, sheep Connexin 49, *Mesocricetus* Connexin 50, *Cricetulus* Connexin 50, Chick Connexin 50, human Connexin 59, or other alpha Connexin. Amino acid sequences for alpha connexins are known in the art and include those identified in Table 1 by accession number.

TABLE 1

Alpha Connexins

| Protein | Accession No. |
| --- | --- |
| mouse Connexin 47 | NP_536702 |
| human Connexin 47 | AAH89439 |
| Human Connexin46.6 | AAB94511 |

TABLE 1-continued

Alpha Connexins

| Protein | Accession No. |
| --- | --- |
| Cow Connexin 46.6 | XP_582393 |
| Mouse Connexin 30.2 | NP_848711 |
| Rat Connexin 30.2 | XP_343966 |
| Human Connexin 31.9 | AAM18801 |
| Dog Connexin 31.9 | XP_548134 |
| Sheep Connexin 44 | AAD56220 |
| Cow Connexin 44 | I46053 |
| Rat Connexin 33 | P28233 |
| Mouse Connexin 33 | AAR28037 |
| Human Connexin 36 | Q9UKL4 |
| mouse Connexin 36 | NP_034420 |
| rat Connexin 36 | NP_062154 |
| dog Connexin 36 | XP_544602 |
| chick Connexin 36 | NP_989913 |
| zebrafish Connexin 36 | NP_919401 |
| *morone* Connexin 35 | AAC31884 |
| *morone* Connexin 35 | AAC31885 |
| *Cynops* Connexin 35 | BAC22077 |
| *Tetraodon* Connexin 36 | CAG06428 |
| human Connexin 37 | I55593 |
| chimp Connexin 37 | XP_524658 |
| dog Connexin 37 | XP_539602 |
| *Cricetulus* Connexin 37 | AAR98615 |
| Mouse Connexin 37 | AAH56613 |
| *Mesocricetus* Connexin37 | AAS83433 |
| Rat Connexin37 | AAH86576 |
| mouse Connexin 39 | NP_694726 |
| rat Connexin 39 | AAN17801 |
| human Connexin 40.1 | NP_699199 |
| *Xenopus* Connexin38 | AAH73347 |
| Zebrafish Connexin 39.9 | NP_997991 |
| Human Connexin 40 | NP_859054 |
| Chimp Connexin 40 | XP_513754 |
| dog Connexin 40 | XP_540273 |
| cow Connexin 40 | XP_587676 |
| mouse Connexin 40 | AAH53054 |
| rat Connexin 40 | AAH70935 |
| *Cricetulus* Connexin 40 | AAP37454 |
| Chick Connexin 40 | NP_990835 |
| human Connexin 43 | P17302 |
| *Cercopithecus* Connexin 43 | AAR33082 |
| *Oryctolagus* Connexin 43 | AAR33084 |
| *Spermophilus* Connexin 43 | AAR33086 |
| *Cricetulus* Connexin 43 | AAO61858 |
| *Phodopus* Connexin 43 | AAR33085 |
| Rat Connexin 43 | AAH81842 |
| *Sus* Connexin 43 | AAR33087 |
| *Mesocricetus* Connexin 43 | AAO61857 |
| Mouse Connexin 43 | AAH55375 |
| *Cavia* Connexin 43 | AAU06305 |
| Cow Connexin 43 | NP_776493 |
| *Erinaceus* Connexin 43 | AAR33083 |
| Chick Connexin 43 | AAA53027 |
| *Xenopus* Connexin 43 | NP_988856 |
| *Oryctolagus* Connexin 43 | AAS89649 |
| *Cyprinus* Connexin 43 | AAG17938 |
| Zebrafish Connexin 43 | CAH69066 |
| *Danio aequipinnatus* Connexin 43 | AAC19098 |
| Zebrafish Connexin 43.4 | NP_571144 |
| Zebrafish Connexin 44.2 | AAH45279 |
| Zebrafish Connexin 44.1 | NP_571884 |
| human Connexin45 | I38430 |
| chimp Connexin45 | XP_511557 |
| dog Connexin 45 | XP_548059 |
| mouse Connexin 45 | AAH71230 |
| cow Connexin 45 | XP_588395 |
| rat Connexin 45 | AAN17802 |
| chick Connexin45 | NP_990834 |
| *Tetraodon* Connexin 45 | CAF93782 |
| chick Connexin 45.6 | I50219 |
| human Connexin 46 | NP_068773 |
| chimp Connexin 46 | XP_522616 |
| mouse Connexin 46 | NP_058671 |
| dog Connexin 46 | XP_543178 |
| rat Connexin 46 | NP_077352 |
| *Mesocricetus* Connexin 46 | AAS83437 |

TABLE 1-continued

Alpha Connexins

| Protein | Accession No. |
|---|---|
| *Cricetulus* Connexin 46 | AAS77618 |
| Chick Connexin 56 | A45338 |
| Zebrafish Connexin 39.9 | NP_997991 |
| cow Connexin 49 | XP_602360 |
| human Connexin 50 | P48165 |
| chimp Connexin 50 | XP_524857 |
| rat Connexin 50 | NP_703195 |
| mouse Connexin 50 | AAG59880 |
| dog Connexin 50 | XP_540274 |
| sheep Connexin 49 | AAF01367 |
| *Mesocricetus* Connexin 50 | AAS83438 |
| *Cricetulus* Connexin 50 | AAR98618 |
| Chick Connexin 50 | BAA05381 |
| human Connexin 59 | AAG09406 |

Thus, the provided polypeptide can comprise the amino acid sequence SEQ ID NO: 1, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:43, SEQ ID NO:90, SEQ ID NO:91, or SEQ ID NO:92 or conservative variants or fragments thereof.

The 20-30 carboxy-terminal-most amino acid sequence of alpha Connexins are characterized by a distinctive and conserved organization. This distinctive and conserved organization would include a type II PDZ binding motif (Φ-x-Φ); wherein x=any amino acid and Φ=a Hydrophobic amino acid; e.g., Table 2, BOLD) and proximal to this motif, Praline (P) and/or Glycine (G) hinge residues; a high frequency phospho-Serine (S) and/or phospho-Threonine (T) residues; and a high frequency of positively charged Arginine (R), Lysine (K) and negatively charged Aspartic acid (D) or Glutamic acid (E) amino acids. For many alpha Connexins, the P and G residues occur in clustered motifs (e.g., Table 2, italicized) proximal to the carboxy-terminal type II PDZ binding motif. The S and T phosphor-amino acids of most alpha Connexins also are typically organized in clustered, repeat-like motifs (e.g., Table 2, underlined). This organization is particularly the case for Cx43, where 90% of 20 carboxyl terminal-most amino acids are comprised of the latter seven amino acids. In a further example of the high conservation of the sequence, ACT peptide organization of Cx43 is highly conserved from humans to fish (e.g., compare Cx43 ACT sequences for humans and zebrafish in Table 2). In another example, the ACT peptide organization of Cx45 is highly conserved from humans to birds (e.g., compare Cx45 ACT sequences for humans and chick in Table 2).). In another example, the ACT peptide organization of Cx36 is highly conserved from primates to fish (e.g., compare Cx36 ACT sequences for chimp and zebrafish in Table 2).

TABLE 2

Alpha Connexin Carboxy-Terminal (ACT) Amino Acid Sequences

| Gene | Sequence | SEQ ID NO |
|---|---|---|
| Human alpha Cx43 | P <u>SSRA SSRA SSR</u> *PRP* D DLEI | (SEQ ID NO: 1) |
| Chick alpha Cx43 | P <u>S RA SSRA SSR</u> *PRP* D DLEI | (SEQ ID NO: 29) |
| Zebrafish alpha Cx43 | P CSRA <u>SSRM SSRA</u> R P D DLDV | (SEQ ID NO: 89) |
| Human alpha Cx45 | G <u>SNKS TA SSKS</u> *GDG* KN SVWI | (SEQ ID NO: 30) |
| Chick alpha Cx45 | G <u>SNKSS</u> A <u>SSKS</u> *GDG* KN SVWI | (SEQ ID NO: 31) |
| Human alpha Cx46 | G RA <u>SKAS RASS</u> *GRARP* E DLAI | SEQ ID NO: 32) |
| Human alpha Cx46.6 | G <u>SASS</u> RD *G* K TVWI | (SEQ ID NO: 33) |
| Chimp alpha Cx36 | P RVSV *PNFG* R TQ <u>SSD</u> SAYV | (SEQ ID NO: 34) |
| Chick alpha Cx36 | P RMSM *PNFG* R TQ <u>SSD</u> <u>S</u> AYV | (SEQ ID NO: 35) |
| Zebrafish alpha Cx36 | P RMSM *PNFG* R TQ <u>SSD</u> <u>S</u> AYV | (SEQ ID NO: 90) |
| Human alpha Cx47 | P RAGSEK G <u>SASS</u> R DG KT TVWI | (SEQ ID NO: 36) |
| Human alpha Cx40 | G HRL *PHG* YHSDKRRL <u>SKASS</u> KARSD DLSV | (SEQ ID NO: 37) |
| Human alpha Cx50 | P ELTTDDAR P LSRL <u>SKASS</u> RARSD DLTV | (SEQ ID NO: 38) |
| Human alpha Cx59 | P NHVV <u>SLTN</u> NLI *GRRVP* T DLQI | (SEQ ID NO: 39) |
| Rat alpha Cx33 | P S CV <u>SSS</u> A VLTTIC <u>SS</u> DQVV *PVG* L <u>SS</u> FYM | (SEQ ID NO: 40) |
| Sheep alpha Cx44 | G R <u>SSKA SKSS</u> *GG* RARAA DLAI | (SEQ ID NO: 41) |
| Human beta Cx26 | LC YLLIR YCSGK SKKPV | (SEQ ID NO: 42) |

Thus, in some aspects, the provided polypeptide comprises one, two, three or all of the amino acid motifs selected from the group consisting of 1) a type II PDZ binding motif, 2) Proline (P) and/or Glycine (G) hinge residues; 3) clusters of phospho-Serine (S) and/or phospho-Threonine (T) residues; and 4) a high frequency of positively charged Arginine (R) and Lysine (K) and negatively charged Aspartic acid (D) and/or Glutamic acid (E) amino acids). In some aspects, the provided polypeptide comprises a type II PDZ binding motif at the carboxy-terminus, Praline (P) and/or Glycine (G) hinge residues proximal to the PDZ binding motif, and positively charged residues (K, R, D, E) proximal to the hinge residues.

PDZ domains were originally identified as conserved sequence elements within the postsynaptic density protein PSD95/SAP90, the *Drosophila* tumor suppressor dlg-A, and the tight junction protein ZO-1. Although originally referred to as GLGF or DHR motifs, they are now known by an acronym representing these first three PDZ-containing proteins (PSD95/DLG/ZO-1). These 80-90 amino acid sequences have now been identified in well over 75 proteins and are characteristically expressed in multiple copies within a single protein. Thus, in some aspects, the provided polypeptide can inhibit the binding of an alpha Connexin to a protein comprising a PDZ domain. The PDZ domain is a specific type of protein-interaction module that has a structurally well-defined interaction 'pocket' that can be filled by a PDZ-binding motif, referred to herein as a "PDZ motif". PDZ motifs are consensus sequences that are normally, but not always, located at the extreme intracellular carboxyl terminus. Four types of PDZ motifs have been classified: type I (S/T-x-Φ), type II (Φ-x-Φ), type III (Ψ-x-Φ) and type IV (D-x-V), where x is any amino acid, Φ is a hydrophobic residue (V, I, L, A, G, W, C, M, F) and Ψ is a basic, hydrophilic residue (H, R, K). (Songyang, Z., et al. 1997. Science 275, 73-77). Thus, in some aspects, the provided polypeptide comprises a type II PDZ binding motif.

It is noted that the 18 carboxy-terminal-most amino acid sequence of alpha Cx37 represents an exceptional variation on the ACT peptide theme. The Cx37 ACT-like sequence is GQKPPSRPSSSASKKQ*YV (SEQ ID NO: 43). Thus the carboxy terminal 4 amino acids of Cx37 conform only in part to a type II PDZ binding domain. Instead of a classical type II PDZ binding domain, Cx37 has a neutral Q* at position 2 where a hydrophobic amino acid would be expected. As such Cx37 comprises what might be termed a type II PDZ binding domain-like sequence. Nonetheless, Cx37 strictly maintains all other aspects of ACT peptide organization including clustered serine residues, frequent R and K residues and a P-rich sequence proximal to the PDZ binding domain-like sequence. Given this overall level of conservation of ACT-like organization in common with the other >70 alpha Connexins listed above, it is understood that the Cx37 ACT-like carboxy terminus functions in the provided capacity.

For comparison, the beta Connexin Cx26 is shown in Table 2. Cx26 has no carboxyl terminal type II PDZ binding motif; less than 30% of the carboxyl terminal most amino acids comprise S, T, R, D or E residues; it has no evidence of motifs proximal to a type II PDZ binding motif or PDZ binding like motif containing clusters of P and G hinge residues; and no evidence of clustered, repeat-like motifs of serine and threonine phosphor-amino acids. Cx26 does have three Lysine (K) residues, clustered one after the other near the carboxy terminus of the sequence. However, no alpha Connexin surveyed in the >70 alpha Connexins listed above was found to display this feature of three repeated K residues domain at carboxy terminus (Cx26 is a beta connexin, thus by definition does not have an ACT domain).

As provided herein, the unique functional characteristics of this relatively short stretch of amino acids encompass the disclosed roles in treating or preventing pathologies involving epithelial permeablization and/or neovascularization. Thus, in some aspects, the provided polypeptide comprises a type II PDZ binding motif (Φ-x-Φ); wherein x=any amino acid and Φ=a Hydrophobic amino acid). In some aspects, greater than 50%, 60%, 70%, 80%, 90% of the amino acids of the provided ACT polypeptide is comprised one or more of Proline (P), Glycine (G), phospho-Serine (S), phospho-Threonine (T), Arginine (R), Lysine (K), Aspartic acid (D), or Glutamic acid (E) amino acid residues.

The amino acids Proline (P), Glycine (G), Arginine (R), Lysine (K), Aspartic acid (D), and Glutamic acid (E) are necessary determinants of protein structure and function. Proline and Glycine residues provide for tight turns in the 3D structure of proteins, enabling the generation of folded conformations of the polypeptide required for function. Charged amino acid sequences are often located at the surface of folded proteins and are necessary for chemical interactions mediated by the polypeptide including protein-protein interactions, protein-lipid interactions, enzyme-substrate interactions and protein-nucleic acid interactions. Thus, in some aspects Proline (P) and Glycine (G) Lysine (K), Aspartic acid (D), and Glutamic acid (E) rich regions proximal to the type II PDZ binding motif provide for properties necessary to the provided actions of ACT peptides. In some aspects, the provided polypeptide comprises Proline (P) and Glycine (G) Lysine (K), Aspartic acid (D), and/or Glutamic acid (E) rich regions proximal to the type II PDZ binding motif.

Phosphorylation is the most common post-translational modification of proteins and is crucial for modulating or modifying protein structure and function. Aspects of protein structure and function modified by phosphorylation include protein conformation, protein-protein interactions, protein-lipid interactions, protein-nucleic acid interactions, channel gating, protein trafficking and protein turnover. Thus, in some aspects the phospho-Serine (S) and/or phospho-Threonine (T) rich sequences are necessary for modifying the function of ACT peptides, increasing or decreasing efficacy of the polypeptides in their provided actions. In some aspects, the provided polypeptide comprise Serine (S) and/or phospho-Threonine (T) rich sequences or motifs.

In another example, respecting definition of an ACT peptide, it is highly auspicious, in light of the high degree of tissue/organ regeneration potential in lower animals such as fish, that a methionine occurs near the amino terminus of the ACT sequence of zebrafish Cx43 (Table 2). In addition to encoding methionine, the methionine base pair triplet is an alternate translation start site. If translation initiated from this methionine, the sequence SSRARPDDLDV (SEQ ID NO:90), would be produced. This translation product maintains all the conserved and distinctive features of a canonical ACT peptide. Specifically this peptide comprises a carboxy terminal type II PDZ binding domain and has a domain enriched in P, R and D residues proximal to the PDZ binding domain. In addition, the sequence comprises a clustered S motif, with potential to modulate ACT peptide function at its amino terminal. This raises the interesting prospect that animals with high tissue/organ regeneration potential such as fish may translate ACT peptides sequences directly.

Thus, in some aspects, the provided polypeptide comprises the c-terminal sequence of human Cx43. Thus, the provided polypeptide can comprise the amino acid sequence SEQ ID NO:1 or SEQ ID NO:2. The polypeptide can comprise 9 amino acids of the carboxy terminus of human Cx40. Thus, the polypeptide can comprise the amino acid sequence SEQ ID NO:5. In other aspects, the provided polypeptide does not comprises the c-terminal sequence of human Cx43. Thus, is some aspects, the provided polypeptide does not consist of the amino acid sequence SEQ ID NO: 1 or SEQ ID NO:2.

When specific proteins are referred to herein, variants, derivatives, and fragments are contemplated. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known and include, for example, M13 primer mutagenesis and PCR mutagenesis. Amino acid substitutions are typically of single residues, but can occur at a number of different locations at once; insertions usually will be on the order of about from 1 to 10 amino acid residues. Deletions or insertions preferably are made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure unless such a change in secondary structure of the mRNA is desired. Substitutional variants are those in which at least one residue has been removed and a different residue inserted in its place. Such substitutions generally are made in accordance with the following Table 3 and are referred to as conservative substitutions.

TABLE 3

Amino Acid Substitutions

| Original Residue | Exemplary Substitutions |
| --- | --- |
| Ala | Ser |
| Arg | Lys |
| Asn | Gln |
| Asp | Glu |
| Cys | Ser |
| Gln | Asn |
| Glu | Asp |
| Gly | Pro |
| His | Gln |
| Ile | Leu; Val |
| Leu | Ile; Val |
| Lys | Arg; Gln |
| Met | Leu; Ile |
| Phe | Met; Leu; Tyr |
| Pro | Gly |
| Ser | Thr |
| Thr | Ser |
| Trp | Tyr |
| Tyr | Trp; Phe |
| Val | Ile; Leu |

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations shown in Table 3. Conservatively substituted variations of each explicitly disclosed sequence are included within the polypeptides provided herein.

Typically, conservative substitutions have little to no impact on the biological activity of a resulting polypeptide. In a particular example, a conservative substitution is an amino acid substitution in a peptide that does not substantially affect the biological function of the peptide. A peptide can include one or more amino acid substitutions, for example 2-10 conservative substitutions, 2-5 conservative substitutions, 4-9 conservative substitutions, such as 2, 5 or 10 conservative substitutions.

A polypeptide can be produced to contain one or more conservative substitutions by manipulating the nucleotide sequence that encodes that polypeptide using, for example, standard procedures such as site-directed mutagenesis or PCR. Alternatively, a polypeptide can be produced to contain one or more conservative substitutions by using standard peptide synthesis methods. An alanine scan can be used to identify which amino acid residues in a protein can tolerate an amino acid substitution. In one example, the biological activity of the protein is not decreased by more than 25%, for example not more than 20%, for example not more than 10%, when an alanine, or other conservative amino acid (such as those listed below), is substituted for one or more native amino acids.

Further information about conservative substitutions can be found in, among other locations, in Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988) and in standard textbooks of genetics and molecular biology.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that there are numerous amino acid and peptide analogs which can be incorporated into the disclosed compositions. For example, there are numerous D amino acids or amino acids which have a different functional substituent than the amino acids shown in Table 3. The opposite stereoisomers of naturally occurring peptides are disclosed, as well as the stereoisomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., *Methods in Molec. Biol.* 77:43-73 (1991), Zoller, *Current Opinion in Biotechnology,* 3:348-354 (1992); Ibba, *Biotechnology & Genetic Engineering Reviews* 13:197-216 (1995), Cahill et al., *TIBS,* 14(10):400-403 (1989); Benner, *TIB Tech,* 12:158-163 (1994); Ibba and Hennecke, *Bio/technology,* 12:678-682 (1994), all of which are herein incorporated by reference at least for material related to amino acid analogs).

Molecules can be produced that resemble polypeptides, but which are not connected via a natural peptide linkage. For example, linkages for amino acids or amino acid analogs can include $CH_2NH$—, —$CH_2S$—, —$CH_2$—$CH_2$—, —CH=CH— (cis and trans), —$COCH_2$—, —CH(OH)$CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., *Int J Pept Prot Res* 14:177-185 (1979) (—CH$_2$NH—, CH$_2$CH$_2$—); Spatola et al. *Life Sci* 38:1243-1249 (1986) (—CHH$_2$—S); Hann *J. Chem. Soc Perkin Trans.* I 307-314 (1982) (—CH—CH—, cis and trans); Almquist et al. *J. Med. Chem.* 23:1392-1398 (1980) (—COCH$_2$—); Jennings-White et al. *Tetrahedron Lett* 23:2533 (1982) (—COCH$_2$—); Szelke et al. European Appln, EP 45665 CA (1982): 97:39405 (1982) (—CH(OH) CH$_2$—); Holladay et al. *Tetrahedron. Lett* 24:4401-4404 (1983) (—C(OH)CH$_2$—); and Hruby *Life Sci* 31:189-199 (1982) (—CH$_2$—S—); each of which is incorporated herein by reference. It is understood that peptide analogs can have more than one atom between the bond atoms, such as b-alanine, g-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, greater ability to cross biological barriers (e.g., gut, blood vessels, blood-brain-barrier), and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch *Ann. Rev. Biochem.* 61:387 (1992), incorporated herein by reference).

Thus, the provided polypeptide can comprise a conservative variant of the c-terminus of an alpha Connexin (ACT). As shown in Table 4, an example of a single conservative substitution within the sequence SEQ ID NO:2 is given in the sequence SEQ ID NO:3. An example of three conservative substitutions within the sequence SEQ ID NO:2 is given in the sequence SEQ ID NO:4. Thus, the provided polypeptide can comprise the amino acid SEQ ID NO:3 or SEQ ID NO:4.

TABLE 4

ACT Polypeptide Variants

| Sequence | SEQ ID NO |
|---|---|
| RPRPDDLEI | SEQ ID NO: 2 |
| RPRPDDLEV | SEQ ID NO: 3 |
| RPRPDDVPV | SEQ ID NO: 4 |
| SSRASSRASSRPRPDDLEV | SEQ ID NO: 44 |
| RPKPDDLEI | SEQ ID NO: 45 |
| SSRASSRASSRPKPDDLEI | SEQ ID NO: 46 |
| RPKPDDLDI | SEQ ID NO: 47 |
| SSRASSRASSRPRPDDLDI | SEQ ID NO: 48 |
| SSRASTRASSRPRPDDLEI | SEQ ID NO: 49 |
| RPRPEDLEI | SEQ ID NO: 50 |

TABLE 4-continued

ACT Polypeptide Variants

| Sequence | SEQ ID NO |
|---|---|
| SSRASSRASSRPRPEDLEI | SEQ ID NO: 51 |
| GDGKNSVWV | SEQ ID NO: 52 |
| SKAGSNKSTASSKSGDGKNSVWV | SEQ ID NO: 53 |
| GQKPPSRPSSSASKKLYV | SEQ ID NO: 54 |

It is understood that one way to define any variants, modifications, or derivatives of the disclosed genes and proteins herein is through defining the variants, modification, and derivatives in terms of sequence identity (also referred to herein as homology) to specific known sequences. Specifically disclosed are variants of the nucleic acids and polypeptides herein disclosed which have at least 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent sequence identity to the stated or known sequence. Those of skill in the art readily understand how to determine the sequence identity of two proteins or nucleic acids. For example, the sequence identity can be calculated after aligning the two sequences so that the sequence identity is at its highest level.

Another way of calculating sequence identity can be performed by published algorithms. Optimal alignment of sequences for comparison may be conducted by the local sequence identity algorithm of Smith and Waterman Adv. Appl. Math. 2: 482 (1981), by the sequence identity alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. These references are incorporated herein by reference in their entirety for the methods of calculating sequence identity.

The same types of sequence identity can be obtained for nucleic acids by, for example, the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

Thus, the provided polypeptide can comprise an amino acid sequence with at least 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent sequence identity to the c-terminus of an alpha Connexin (ACT). Thus, in some aspects, the provided polypeptide comprises an amino acid sequence with at least 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent sequence identity to SEQ ID NO:1, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:90, SEQ ID NO:91, or SEQ ID NO:92. As an example, provided is a polypeptide (SEQ ID NO:4) having 66% sequence identity to the same stretch of 9 amino acids occurring on the carboxy-terminus of human Cx43 (SEQ ID NO:2).

The herein provided polypeptides can be added directly to a tissue in a subject. However, efficiency of cytoplasmic localization of the provided polypeptide is enhanced by cellular internalization transporter chemically linked in cis or trans with the polypeptide. Efficiency of cell internalization transporters are enhanced further by light or co-transduction of cells with Tat-HA peptide.

Thus, the provided polypeptide can comprise a cellular internalization transporter or sequence. The cellular internalization sequence can be any internalization sequence known or newly discovered in the art, or conservative variants thereof. Non-limiting examples of cellular internalization transporters and sequences include Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol) (see Table 5).

Thus, the provided polypeptide can further comprise the amino acid sequence SEQ ID NO:7, SEQ ID NO:14 (Bocci, M. et al. 2000. *Nat. Med.* 6, 1362-1367), SEQ ID NO:15 (Derossi, D., et al. 1994. *Biol. Chem.* 269, 10444-10450), SEQ ID NO: 16 (Fischer, P. M. et al 2000. *J. Pept. Res.* 55, 163-172), SEQ ID NO:17 (Frankel, A. D. & Pabo, C. O. 1988. *Cell* 55, 1189-1193; Green, M. & Loewenstein, P. M. 1988. *Cell* 55, 1179-1188), SEQ ID NO: 18 (Park, C. B., et al. 2000. *Proc. Natl Acad. Sci. USA* 97, 8245-8250), SEQ ID NO: 19 (Pooga, M., et al. 1998. *FASEB J.* 12, 67-77), SEQ ID NO:20 (Oehlke, J. et al. 1998. *Biochim. Biophys. Acta.* 1414, 127-139), SEQ ID NO:21 (Lin, Y. Z., et al. 1995. *J. Biol. Chem.* 270, 14255-14258), SEQ ID NO:22 (Sawada, M., et al. 2003. *Nature Cell Biol.* 5, 352-357), SEQ ID NO:23 (Lundberg, P. et al. 2002. *Biochem. Biophys. Res. Commun.* 299, 85-90), SEQ ID NO:24 (Elmquist, A., et al. 2001. *Exp. Cell Res.* 269, 237-244), SEQ ID NO:25 (Morris, M. C., et al. 2001. *Nature Biotechnol.* 19, 1173-1176), SEQ ID NO:26 (Rousselle, C. et al. 2000. *Mol. Pharmacol.* 57,

TABLE 5

Cell Internalization Transporters

| Name | Sequence | SEQ ID NO |
|---|---|---|
| Antp | RQPKIWFPNRRKPWKK | (SEQ ID NO:7) |
| HIV-Tat | GRKKRRQRPPQ | (SEQ ID NO:14) |
| Penetratin | RQIKIWFQNRRMKWKK | (SEQ ID NO:15) |
| Antp-3A | RQIAIWFQNRRMKWAA | (SEQ ID NO:16) |
| Tat | RKKRRQRRR | (SEQ ID NO:17) |
| Buforin II | TRSSRAGLQFPVGRVHRLLRK | (SEQ ID NO:18) |
| Transportan | GWTLNSAGYLLGKINKALAALAKKIL | (SEQ ID NO:19) |
| model amphipathic peptide (MAP) | KLALKLALKALKAALKLA | (SEQ ID NO:20) |
| K-FGF | AAVALLPAVLLALLAP | (SEQ ID NO:21) |
| Ku70 | VPMLK-PMLKE | (SEQ ID NO:22) |
| Prion | MANLGYWLLALFVTMWTDVGLCKKRPKP | (SEQ ID NO:23) |
| pVEC | LLIILRRRIRKQAHAHSK | (SEQ ID NO:24) |
| Pep-1 | KETWWETWWTEWSQPKKKRKV | (SEQ ID NO:25) |
| SynB1 | RGGRLSYSRRRFSTSTGR | (SEQ ID NO:26) |
| Pep-7 | SDLWEMMMVSLACQY | (SEQ ID NO:27) |
| HN-1 | TSPLNIHNGQKL | (SEQ ID NO:28) |
| BGSC (Bis-Guanidinium-Spermidine-Cholesterol) | | |
| BGTC (Bis-Guanidinium-Tren-Cholesterol) | | |

679-686), SEQ ID NO:27 (Gao, C. et al. 2002. *Bioorg. Med. Chem.* 10, 4057-4065), or SEQ ID NO:28 (Hong, F. D. & Clayman, G. L. 2000. *Cancer Res.* 60, 6551-6556). The provided polypeptide can further comprise BGSC (Bis-Guanidinium-Spermidine-Cholesterol) or BGTC (Bis-Guanidinium-Tren-Cholesterol) (Vigneron, J. P. et al. 1998. *Proc. Natl. Acad. Sci. USA.* 93, 9682-9686). The preceding references are hereby incorporated herein by reference in their entirety for the teachings of cellular internalization vectors and sequences. Any other internalization sequences now known or later identified can be combined with a peptide of the invention.

The provided polypeptide can comprise any ACT sequence (e.g, any of the ACT peptides disclosed herein) in combination with any of the herein provided cell internalization sequences. Examples of said combinations are given in Table 6. Thus, the provided polypeptide can comprise an Antennapedia sequence comprising amino acid sequence SEQ ID NO:7. Thus, the provided polypeptide can comprise the amino acid sequence SEQ ID NO:8, SEQ ID NO:9, SEQ ID NO: 10, SEQ ID NO: 11, or SEQ ID NO: 12.

TABLE 6

ACT Polypeptides with Cell Internalization Sequences (CIS)

| CIS/ACT | Sequence | SEQ ID NO |
|---|---|---|
| Antp/ACT 2 | RQPKIWFPNRRKPWKK PSSRASSRASSRPRPDDLEI | SEQ ID NO: 8 |
| Antp/ACT 1 | RQPKIWFPNRRKPWKK RPRPDDLEI | SEQ ID NO: 9 |
| Antp/ACT 3 | RQPKIWFPNRRKPWKK RPRPDDLEV | SEQ ID NO: 10 |
| Antp/ACT 4 | RQPKIWFPNRRKPWKK RPRPDDVPV | SEQ ID NO: 11 |
| Antp/ACT 5 | RQPKIWFPNRRKPWKK KARSDDLSV | SEQ ID NO: 12 |
| HIV-Tat/ACT 1 | GRKKRRQRPPQ RPRPDDLEI | SEQ ID NO: 56 |
| Penetratin/ACT 1 | RQIKIWFQNRRMKWKK RPRPDDLEI | SEQ ID NO 57 |
| Antp-3A/ACT 1 | RQIAIWFQNRRMKWAA RPRPDDLEI | SEQ ID NO: 58 |
| Tat/ACT 1 | RKKRRQRRR RPRPDDLEI | SEQ ID NO: 59 |
| Buforin II/ACT 1 | TRSSRAGLQFPVGRVHRLLRK RPRPDDLEI | SEQ ID NO: 60 |
| Transportan/ACT 1 | GWTLNSAGYLLGKINKALAALAKKIL RPRPDDLEI | SEQ ID NO: 61 |
| MAP/ACT I | KLALKLALKALKAALKLA RPRPDDLEI | SEQ ID NO: 62 |
| K-FGF/ACT 1 | AAVALLPAVLLALLAP RPRPDDLEI | SEQ ID NO: 63 |
| Ku70/ACT 1 | VPMLKPMLKE RPRPDDLEI | SEQ ID NO: 64 |
| Prion/ACT 1 | MANLGYWLLALFVTMWTDVGLCKKRPKP RPRPDDLEI | SEQ ID NO: 65 |

TABLE 6-continued

ACT Polypeptides with Cell Internalization Sequences (CIS)

| CIS/ACT | Sequence | SEQ ID NO |
|---|---|---|
| pVEC/ACT 1 | LLIILRRRIRKQAHAHSK RPRPDDLEI | SEQ ID NO: 66 |
| Pep-1/ACT 1 | KETWWETWWTEWSQPKKKRKV RPRPDDLEI | SEQ ID NO: 67 |
| SynB1/ACT 1 | RGGRLSYSRRRFSTSTGR RPRPDDLEI | SEQ ID NO: 68 |
| Pep-7/ACT 1 | SDLWEMMMVSLACQY RPRPDDLEI | SEQ ID NO: 69 |
| HN-1/ACT I | TSPLNIHNGQKL RPRPDDLEI | SEQ ID NO: 70 |

Also provided are isolated nucleic acids encoding the polypeptides provided herein. The disclosed nucleic acids are made up of for example, nucleotides, nucleotide analogs, or nucleotide substitutes. Non-limiting examples of these and other molecules are discussed herein. It is understood that for example, when a vector is expressed in a cell, the expressed mRNA will typically be made up of A, C, G, and U.

By "isolated nucleic acid" or "purified nucleic acid" is meant DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (e.g., a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, e.g., other types of RNA molecules or polypeptide molecules.

Thus, provided is an isolated nucleic acid encoding a polypeptide comprising the amino acid sequence SEQ ID NO: 1, SEQ ID NO:2, SEQ ID NO:3, SEQ ID NO:4, SEQ ID NO:5, SEQ ID NO:7, SEQ ID NO:8, SEQ ID NO:9, SEQ ID NO:10, SEQ ID NO:11, or SEQ ID NO:12.

Thus, the provided nucleic acid can comprise the nucleic acid sequence SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, or SEQ ID NO:89.

The herein provided nucleic acid can be operably linked to an expression control sequence. Also provided is a vector comprising one or more of the herein provided nucleic acids, wherein the nucleic acid is operably linked to an expression control sequence. There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transaction, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as SEQ ID NO:6, into the cell without degradation and include a promoter yielding expression of the gene in the cells into which it is delivered. In some embodiments the promoters are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also disclosed are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. Also disclosed is a viral vector which has been engineered so as to suppress the immune response of the host organism, elicited by the viral antigens. Vectors of this type can carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest 92:1580-1586 (1993); Kirshenbaum, J. Clin. Invest. 92:381-387 (1993); Roessler, J. Clin. Invest 92:1085-1092 (1993); Moullier, Nature Genetics 4:154-159 (1993); La Salle, Science 259:988-990 (1993);

Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed, and these virons are generated in a cell line such as the human 293 cell line. In some aspects, both the E1 and E3 genes are removed from the adenovirus genome.

Another type of viral vector is based on an adeno-associated virus (AAV). This defective parvovirus can infect many cell types and is nonpathogenic to humans. AAV type vectors can transport about 4 to 5 kb and wild type AAV is known to stably insert into chromosome 19. As an example, this vector can be the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Molecular genetic experiments with large human herpes viruses have provided a means whereby large heterologous DNA fragments can be cloned, propagated and established in cells permissive for infection with herpes viruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA >150 kb to specific cells. EBV recombinants can maintain large pieces of DNA in the infected B-cells as episomal DNA. Individual clones carried human genomic inserts up to 330 kb appeared genetically stable. The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA >220 kb and to infect cells that can stably maintain DNA as episomes.

Other useful systems include, for example, replicating and host-restricted non-replicating vaccinia virus vectors.

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed polypeptides, nucleic acids or vectors, for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. Am. J. Resp. Cell. Mol. Biol. 1:95-100 (1989); Felgner et al. Proc. Natl. Acad. Sci USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can become integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

The compositions can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Promoters controlling transcription from vectors in mammalian host cells may be obtained from various sources, for example, the genomes of viruses such as: polyoma, Simian Virus 40 (SV40), adenovirus, retroviruses, hepatitis-B virus, cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio, 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A promoter of this type is the CMV promoter (650 bases). Other such promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. The transcription unit can also contain a polyadenylation region. One benefit of this region is that it increases the likelihood that the transcribed unit will be processed and transported like mRNA. The identification and use of polyadenylation signals in expression constructs is well established. Homologous polyadenylation signals can be used in the transgene constructs. In certain transcription units, the polyadenylation region is derived from the SV40 early polyadenylation signal and consists of about 400 bases. Transcribed units contain other standard sequences alone or in combination with the above sequences improve expression from, or stability of, the construct.

The viral vectors can include nucleic acid sequence encoding a marker product. This marker product is used to determine if the gene has been delivered to the cell and once delivered is being expressed. Example marker genes are the *E. Coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: Chinese hamster ovary (CHO) DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1:327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

Also provided is a cell comprising one or more of the herein provided vectors. As used herein, "cell", "cell line", and "cell culture" may be used interchangeably and all such designations include progeny. The disclosed cell can be any cell used to clone or propagate the vectors provided herein. Thus, the cell can be from any primary cell culture or established cell line. The method may be applied to any cell, including prokaryotic or eukaryotic, such as bacterial, plant, animal, and the like. The cell type can be selected by one skilled in the art based on the choice of vector and desired use.

Disclosed are animals produced by the process of transfecting a cell within the animal with any of the nucleic acid molecules or vectors disclosed herein. Disclosed are animals produced by the process of transfecting a cell within the animal any of the nucleic acid molecules or vectors disclosed herein, wherein the animal is a mammal. Also disclosed are animals produced by the process of transfecting a cell within the animal any of the nucleic acid molecules or vectors disclosed herein, wherein the mammal is mouse, rat, rabbit, cow, sheep, pig, or primate.

Provided is a composition comprising one or more of the herein provided polypeptides, nucleic acids, or vectors in a pharmaceutically acceptable carrier. Thus, provided is a composition comprising a combination of two or more of any of the herein provided ACT polypeptides in a pharmaceutically acceptable carrier. For example, provided is a composition comprising SEQ ID NO: 1 and SEQ ID NO:5 in a pharmaceutically acceptable carrier.

By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The herein provide composition can further comprise any known or newly discovered substance that can be administered to a tissue of a subject. For example, the provided composition can further comprise one or more of classes of antibiotics (e.g. Aminoglycosides, Cephalosporins, Chloramphenicol, Clindamycin, Erythromycins, Fluoroquinolones, Macrolides, Azolides, Metronidazole, Penicillin's, Tetracycline's, Trimethoprim-sulfamethoxazole, Vancomycin), steroids (e.g. Andranes (e.g. Testosterone), Cholestanes (e.g. Cholesterol), Cholic acids (e.g. Cholic acid), Corticosteroids (e.g. Dexamethasone), Estraenes (e.g. Estradiol), Pregnanes (e.g. Progesterone), narcotic and non-narcotic analgesics (e.g. Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, Pentazocine), chemotherapy (e.g. anti-cancer drugs such as but not limited to Altretamine, Asparaginase, Bleomycin, Busulfan, Carboplatin, Carmustine, Chlorambucil, Cisplatin, Cladribine, Cyclophosphamide, Cytarabine, Dacarbazine, Diethyl stilbesterol, Ethinyl estradiol, Etoposide, Floxuridine, Fludarabine, Fluorouracil, Flutamide, Goserelin, Hydroxyurea, Idarubicin, Ifosfamide, Leuprolide, Levamisole, Lomustine, Mechlorethamine, Medroxyprogesterone, Megestrol, Melphalan, Mercaptopurine, Methotrexate, Mitomycin, Mitotane, Mitoxantrone, Paclitaxel, pentastatin, Pipobroman, Plicamycin, Prednisone, Procarbazine, Streptozocin, Tamoxifen, Teniposide, Vinblastine, Vincristine), anti-inflammatory agents (e.g. Alclofenac; Alclometasone Dipropionate; Algestone Acetonide; alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Decanoate; Deflazacort; Delatestryl; Depo-Testosterone; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Lotepredenol Etabonate; Meclofenamate Sodium; Meclofenamic Acid; Meclorisone Dibutyrate; Mefenamic Acid; Mesalamine; Meseclazone; Mesterolone; Methandrostenolone; Methenolone; Methenolone Acetate; Methylprednisolone Suleptanate; Momiflumate; Nabumetone; Nandrolone; Naproxen; Naproxen Sodium; Naproxol; Nimazone; Olsalazine Sodium; Orgotein; Orpanoxin; Oxandrolane; Oxaprozin; Oxyphenbutazone; Oxymetholone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Stanozolol; Sudoxicam; Sulindac; Suprofen; Talmetacin; Talniflumate; Talosalate; Tebufelone; Tenidap; Tenidap Sodium; Tenoxicam; Tesicam; Tesimide; Testosterone; Testosterone Blends; Tetrydamine; Tiopinac; Tixocortol Pivalate; Tolmetin; Tolmetin Sodium; Triclonide; Triflumidate; Zidometacin; Zomepirac Sodium), or anti-histaminic agents (e.g. Ethanolamines (like diphenhydrmine carbinoxamine), Ethylenediamine (like tripelennamine pyrilamine), Alkylamine (like chlorpheniramine, dexchlorpheniramine, brompheniramine, triprolidine), other anti-histamines like astemizole, loratadine, fexofenadine, Bropheniramine, Clemastine, Acetaminophen, Pseudoephedrine, Triprolidine).

The herein provide composition can further comprise anti-VEGF (anti-Vascular Endothelial Growth Factor) agents. Examples of these agents include Lucentis, Avastin and Macugen.

The compositions may be administered topically, orally, or parenterally. For example, the compositions can be administered extracorporeally, intracranially, intravaginally, intraanally, subcutaneously, intradermally, intracardiac, intragastric, intravenously, intramuscularly, by intraperitoneal injection, transdermally, intranasally, or by inhalant. As used herein, "intracranial administration" means the direct delivery of substances to the brain including, for example, intrathecal, intracisternal, intraventricular or trans-sphenoidal delivery via catheter or needle.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

The materials may be in solution or suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129:57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. Those receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution can be from about 5 to about 8, from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels (e.g., poloxamer gel), drops, suppositories, sprays, liquids and powders. Conventional pharmaceutical carriers, aqueous, powder or oily bases, thickeners and the like may be necessary or desirable. The disclosed compositions can be administered, for example, in a microfiber, polymer (e.g., collagen), nanosphere, aerosol, lotion, cream, fabric, plastic, tissue engineered scaffold, matrix material, tablet, implanted container, powder, oil, resin, wound dressing, bead, microbead, slow release bead, capsule, injectables, intravenous drips, pump device, silicone implants, or any bio-engineered materials.

In some aspects the provided pharmaceutically acceptable carrier is a poloxamer. Poloxamers, referred to by the trade name Pluronics®, are nonionic surfactants that form clear thermoreversible gels in water. Poloxamers are polyethylene oxide-polypropylene oxide-polyethylene oxide (PEO-PPO-PEO) tri-block copolymers. The two polyethylene oxide chains are hydrophilic but the polypropylene chain is hydrophobic. These hydrophobic and hydrophilic characteristics take charge when placed in aqueous solutions. The PEO-PPO-PEO chains take the form of small strands where the hydrophobic centers would come together to form micelles. The micelle, sequentially, tend to have gelling characteristics because they come together in groups to form solids (gels) where water is just slightly present near the hydrophilic ends. When it is chilled, it becomes liquid, but it hardens when warmed. This characteristic makes it useful in pharmaceutical compounding because it can be drawn into a syringe for accurate dose measurement when it is cold. When it warms to body temperature (when applied to skin) it thickens to a perfect consistency (especially when combined with soy lecithin/isopropyl palmitate) to facilitate proper inunction and adhesion. Pluronic® F127 (F127) is widely used because it is obtained easily and thus it is used in such pharmaceutical applications. F127 has a EO:PO:EO ratio of 100:65:100, which by weight has a PEO:PPO ratio of 2:1. Pluronic gel is an aqueous solution and typically contains 20-30% F-127. Thus, the provided compositions can be administered in F127.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual doctor in the event of any counterindications. Dosage can vary, and can be administered in one or more dose administrations daily, for one or several days. Guidance can be found in the literature for appropriate dosages for given classes of pharmaceutical products. The range of dosage largely depends on the application of the compositions herein, severity of condition, and its route of administration.

For example, in applications as a laboratory tool for research, the ACT peptide compositions can be used in doses as low as 0.01% w/v. The dosage can be as low as 0.02% w/v and possibly as high as 2% w/v in topical treatments. Thus, upper limits of the provided polypeptides may be up to 2-5% w/v or v/v if given as an initial bolus delivered for example directly into a tumor mass. Recommended upper limits of dosage for parenteral routes of administration for example intramuscular, intracerebral, intracardicardiac and intraspinal could be up to 1% w/v or v/v. This upper dosage limit may vary by formulation, depending for example on how the polypeptide(s) is combined with other agents promoting its action or acting in concert with the polypeptide(s).

For continuous delivery of the provided polypeptides, for example, in combination with an intravenous drip, upper limits of 0.01 g/Kg body weight over time courses determined by the doctor based on improvement in the condition can be used. In another example, upper limits of concentration of the provided nucleic acids delivered topically would be 5-10 jag/cm$^2$ of tissue depending for example on how the nucleic acid is combined with other agents promoting its action or acting in concert with the nucleic acids. This would be repeated at a frequency determined by the Doctor based on improvement. In another example, upper limits of concentration of the provided nucleic acids delivered internally for example, intramuscular, intracerebral, intracardicardiac and intraspinal would be 50-100 jag/ml of solution. Again, the frequency would be determined by the Doctor based on improvement.

Viral vectors remain highly experimental tools that nonetheless show considerable potential in clinical applications. As such, caution is warranted in calculation of expected dosage regimes for viral vectors and will depend considerably on the type of vector used. For example, retroviral vectors infect dividing cells such as cancer cells efficiently, intercalating into the host cell genome and continuing expression of encoded proteins indefinitely. Typical dosages of retroviruses in an animal model setting are in the range of $10^7$ to $10^9$ infectious units per ml. By contrast, adenoviruses most efficiently target post-mitotic cells, but cells are quickly eliminated by the host immune system or virus is eventually lost if infected cells resume proliferation and subsequently dilute the viral episomal DNA. Indeed, this transient time course of infection may be useful for short-term delivery of the composition described herein in certain clinical situations. In animal models, concentrations of $10^8$-$10^{11}$ infectious units per ml of adenovirus are typical for uses in research. Dose ranges of vectors based on data derived from animal models would be envisaged to be used eventually in clinical setting(s), pending the development of pharmaceutically acceptable formulation(s).

Two topical applications of ACT compositions at 0.02% w/v; one applied acutely and the second applied 24 hours later can be used in treating or preventing pathologies involving epithelial permeablization and/or neovascularization. However, in a clinical setting an increased frequency of up to 3 applications per day topically at a concentration of up to 5% is recommended until significant improvement is achieved as determined by a Doctor. For internal administration, for example, intravenously, intramuscularly, intracerebral, intracardicardiac and intraspinally and increased frequency of up to 3 dosages of 1% w/v or v/v per day is recommended until significant improvement is determined by the Doctor.

Also provided are materials comprising the herein provided compositions (e.g., polypeptides, nucleic acids, or vectors). For example, provided are materials coated with an ACT polypeptide.

For example, the material can be soaked in the provided polypeptide at a concentration ranging from 10-200 µM. The material can then be dried and sealed in a sterile container. The material can also be immersed in liquid 10-30% pluronic gel at 4° C. containing polypeptide at 10-200 µM concentration. The material can then be brought to approximate room temperature so that the gel polymerizes, leaving a coat of polypeptide-impregnated gel surrounding the material, which can be sealed in a sterile container. The polypeptide can also be incorporated into a cross-linkable hydrogel system, such as the poly(lactic-co-glycolic acid) (PLGA) or polyurethane, which can then be fashioned into materials for treating a desired pathology. Thus, provided are composite hydrogel-peptide materials.

B. Methods of Using the Compositions

Provided herein are compositions and methods for treating or preventing pathologies involving epithelial permeablization and/or neovascularization (e.g., angiogenesis or vasculogenesis), comprising administering to the subject a polypeptide comprising a carboxy-terminal amino acid sequence of an alpha Connexin, also referred to herein as an alpha Connexin carboxy-Terminal (ACT) polypeptide, or a conservative variant thereof.

In some aspects, the epithelial permeablization and/or neovascularization of the disclosed methods is mediated by vascular endothelial growth factor (VEGF), which promotes vascular permeability and angiogenesis/vasculogenesis.

For example, provided is a method of treating or preventing respiratory distress syndrome (RDS) in a subject, comprising: identifying a subject having or at risk of having said RDS, and administering to the lung of the subject a polypeptide disclosed herein.

Also provided is a method of treating or preventing ischemia in a subject, comprising: identifying a subject having or at risk of having said RDS, and administering to the lung of the subject a polypeptide disclosed herein.

Also provided is a method of treating or preventing hemorrhagic stroke in a subject, comprising: identifying a subject having or at risk of having said RDS, and administering to the lung of the subject a polypeptide disclosed herein.

Also provided is a method a treating or preventing reperfusion injury, such as that observed in myocardial infarction and stroke, in a subject, comprising: identifying a subject having or at risk of having said RDS, and administering to the lung of the subject a polypeptide disclosed herein.

Also provided is a method of treating or preventing a dermal vascular blemish or malformation in a subject, comprising: identifying a subject having or at risk of having said blemish, and administering to the skin of the subject a polypeptide disclosed herein.

1. Macular Degeneration

Also provided herein is a method of treating or preventing macular degeneration in a subject, comprising administering to the subject a therapeutically effective amount of an isolated polypeptide comprising the carboxy-terminal amino acid sequence of an alpha Connexin, or a conservative variant thereof.

Also provided herein is a method of treating or preventing macular degeneration in a subject comprising: identifying a subject having or at risk of having said macular degeneration, and administering to the eye of the subject a polypeptide disclosed herein.

By "macular degeneration" is meant the degeneration of the center of the inner lining of the eye, known as the macula. In some aspects, the macular degeneration is age-related macular degeneration (AMD). In some aspects, the macular degeneration is neovascular or exudative AMD, the wet form of advanced AMD.

Also provided is a method of reducing or preventing neovascularization of choriocapillaries through Bruch's membrane.

In some aspects, the subject has been diagnosed with macular degeneration. In some aspects, the subject has been identified as being at risk of developing macular degeneration. Thus, the subject can be anyone over 50, 60, 65, 70, 75 years of age. In some aspects, the subject is known to smoke tobacco. In some aspects, the subject is known to have a relative with macular degeneration. In some aspects, the subject has been identified as having a single nucleotide polymorphism (SNP) associated with macular degeneration. For example, the SNP can be complement system protein factor H (CFH) Tyr402His. As another example, the SNP can be rs11200638 in HTRA1. In some aspects, the subject has been identified as having high blood pressure. In some aspects, the subject has been identified as having high cholesterol. In some aspects, the subject is obese. In some aspects, the subject has been identified as having drusen in the macula. In some aspects, the subject has been identified as having abnormal neovascularization of choriocapillaries through Bruch's membrane.

Macular degeneration is a medical condition predominantly found in elderly adults in which the center of the inner lining of the eye, known as the macula area of the retina, suffers thinning, atrophy, and in some cases, bleeding. This can result in loss of central vision, which entails inability to see fine details, to read, or to recognize faces. According to the American Academy of Ophthalmology, it is the leading cause of central vision loss (blindness) in the United States today for those over the age of fifty years. Although some macular dystrophies that affect younger individuals are sometimes referred to as macular degeneration, the term generally refers to age-related macular degeneration (AMD or ARMD).

Age-related macular degeneration begins with characteristic yellow deposits in the macula called drusen between the retinal pigment epithelium and the underlying choroid. Thus, also provided is a method of reducing or preventing drusen in the macula of a subject. Drusen are tiny yellow or white accumulations of extracellular material that build up in Bruch's membrane of the eye. The presence of a few small ("hard") drusen is normal with advancing age, and most people over 40 have some hard drusen. However, the presence of larger and more numerous drusen in the macula is a common early sign of age-related macular degeneration (AMD). Drusen associated with aging and macular degeneration are distinct from optic disc drusen, which are present in the optic nerve head. Both age-related drusen and optic disc drusen can be observed by ophthalmoscopy.

Most people with these early changes (referred to as age-related maculopathy) have good vision. People with drusen can go on to develop advanced AMD. The risk is considerably higher when the drusen are large and numerous and associated with disturbance in the pigmented cell layer under the macula. Recent research indicates that large and soft drusen are related to elevated cholesterol deposits and can respond to cholesterol lowering agents or the Rheo Procedure.

Advanced AMD, which is responsible for profound vision loss, has two forms: dry and wet. Central geographic atrophy, the dry form of advanced AMD, results from atrophy to the retinal pigment epithelial layer below the retina, which causes vision loss through loss of photoreceptors (rods and cones) in the central part of the eye. Vitamin supplements with high doses of antioxidants, lutein and zeaxanthin, have been demonstrated by the National Eye Institute and others to slow the progression of dry macular degeneration and in some patients, improve visual acuity.

Neovascular or exudative AMD, the wet form of advanced AMD, causes vision loss due to abnormal blood vessel growth in the choriocapillaries, through Bruch's membrane, ultimately leading to blood and protein leakage below the macula. Bleeding, leaking, and scarring from these blood vessels eventually cause irreversible damage to the photoreceptors and rapid vision loss if left untreated.

Anti-angiogenics or anti-VEGF (anti-Vascular Endothelial Growth Factor) agents, when injected directly into the vitreous humor of the eye using a small needle, can cause regression of the abnormal blood vessels and improvement of vision. The injections frequently have to be repeated on a monthly or bi-monthly basis. Examples of these agents include Lucentis, Avastin and Macugen. Only Lucentis and Macugen are FDA approved as of April 2007.

The Amsler Grid Test is one of the simplest and most effective methods for patients to monitor the health of the macula. The Amsler Grid is essentially a pattern of intersecting lines (identical to graph paper) with a black dot in the middle. The central black dot is used for fixation (a place for the eye to stare at). With normal vision, all lines surrounding the black dot will look straight and evenly spaced with no missing or odd looking areas when fixating on the grid's central black dot. When there is disease affecting the macula, as in macular degeneration, the lines can look bent, distorted and/or missing.

Macular degeneration by itself will not lead to total blindness. For that matter, only a very small number of people with visual impairment are totally blind. In almost all cases, some peripheral vision remains. Other complicating conditions may possibly lead to such an acute condition (severe stroke or trauma, untreated glaucoma, etc.), but few macular degeneration patients experience total visual loss. The area of the macula comprises about 5% of the retina and is responsible for about 35% of the visual field. The remaining 65% (the peripheral field) remains unaffected by the disease.

Similar symptoms with a very different etiology and different treatment can be caused by Epiretinal membrane or macular pucker or leaking blood vessels in the eye.

Fluorescein angiography allows for the identification and localization of abnormal vascular processes. Optical coherence tomography is now used by most ophthalmologists in the diagnosis and the follow-up evaluation of the response to treatment by using either Avastin or Lucentis which are injected into the vitreous of the eye at various intervals.

Juvenile macular degeneration is not a term in standard usage at this time. The preferred term for conditions that affect the macula in younger individuals related to genetics is macular dystrophy. Examples of these include: Best's disease, Doyne's honeycomb retinal dystrophy, Sorsby's disease, and Stargardt's disease.

In some aspects, subjects are identified by medical diagnosis. For example, subjects with diabetic retinopathy and macular degeneration can be identified by visualization of excess blood vessels in the eyes. Acute lung injury can be diagnosed by lung edema in the absence of congestive heart failure. Ischemic stroke can be diagnosed by neurologic presentation and imaging (MRI and CT). Other known or newly discovered medical determinations can be used to identify subjects for use in the disclosed methods.

In addition, subjects can be identified by genetic predisposition. For example, genes that predispose patients to age related macular degeneration have been identified (Klein R J, et al, 2005; Yang Z, et al. 2006; Dewan A, et al. 2006). Likewise, genetic mutations that predispose patients to vascular malformations in the brain have been identified (Plummer N W, et al., 2005). Other known or newly discovered genetic determinations can be used to identify subjects for use in the disclosed methods.

2. Diabetic Retinopathy

Also provided is a method of treating or preventing diabetic retinopathy in a subject comprising: identifying a subject having or at risk of having said diabetic retinopathy, and administering to the retina of the subject a polypeptide disclosed herein.

Diabetic retinopathy is damage to the retina caused by complications of diabetes mellitus, which could eventually lead to blindness. It is an ocular manifestation of systemic disease which affects up to 80% of all diabetics who have had diabetes for 10 years or more. Despite these intimidating statistics, research indicates that at least 90% of these new cases could be reduced if there was proper and vigilant treatment and monitoring of the eyes.

Diabetic retinopathy often has no early warning signs. Even macular edema, which can cause vision loss more rapidly, may not have any warning signs for sonic time. In general, however, a person with macular edema is likely to have blurred vision, making it hard to read or drive, for example. In some cases, the vision will get better or worse during the day.

As new blood vessels form at the back of the eye as a part of proliferative diabetic retinopathy (PDR), they can bleed (haemorrhage) and blur vision. The first time this happens, it may not be very severe. In most cases, it will leave just a few specks of blood, or spots, floating in a person's visual field, though the spots often go away after a few hours.

These spots are often followed within a few days or weeks by a much greater leakage of blood, which blurs vision. In extreme cases, a person will only be able to tell light from dark in that eye. It may take the blood anywhere from a few days to months or even years to clear from the inside of the eye, and in some cases the blood will not clear. These types of large hemorrhages tend to happen more than once, often during sleep.

Diabetic retinopathy is the result of microvascular retinal changes. Hyperglycemia-induced pericyte death and thickening of the basement membrane lead to incompetence of the vascular walls. These damages change the formation of the blood-retinal barrier and also make the retinal blood vessels become more permeable.

Small blood vessels—such as those in the eye—are especially vulnerable to poor blood sugar control. An overaccumulation of glucose and/or fructose damages the tiny blood vessels in the retina. During the initial stage, called nonproliferative diabetic retinopathy (NPDR), most people do not notice any change in their vision.

Some people develop a condition called macular edema. It occurs when the damaged blood vessels leak fluid and lipids into the macula, the part of the retina that lets us see detail. The fluid makes the macula swell, which blurs vision.

As the disease progresses, severe nonproliferative diabetic retinopathy can enter an advanced, or proliferative, stage. The lack of oxygen in the retina causes fragile, new, blood vessels to grow along the retina and into the clear, gel-like vitreous humour that fills the inside of the eye. Without timely treatment, these new blood vessels can bleed, cloud vision, and destroy the retina. Fibrovascular proliferation can also cause tractional retinal detachment. New blood vessels can also grow into the angle of the anterior chamber of the eye and cause neovascular glaucoma. Nonproliferative diabetic retinopathy shows up as cotton wool spots (microinfarction of the retina), lipid exudate, intraretinal microvascular abnormalities (IRMA), or microvascular abnormalities or as superficial retinal hemorrhages. Even so, the advanced proliferative diabetic retinopathy (PDR) can remain asymptomatic for a very long time, and so should be monitored closely with regular checkups.

All people with diabetes mellitus are at risk—those with Type I diabetes (juvenile onset) and those with Type II diabetes (adult onset). The longer a person has diabetes, the higher the risk of developing some ocular problem. Between 40 to 45 percent of Americans diagnosed with diabetes have some stage of diabetic retinopathy. After 20 years of diabetes, nearly all patients with type 1 diabetes and >60% of patients with type 2 diabetes have some degree of retinopathy.

Diabetic retinopathy is detected during an eye examination that includes Visual acuity test, Pupil dilation, Ophthalmoscopy, Ocular Coherence Tomography or OCT, Tonometry, Digital Retinal Screening Programs, and Slit Lamp Biomicroscopy Retinal Screening Programs.

Visual acuity test uses an eye chart to measure how well a person sees at various distances (i.e., visual acuity). During Pupil dilation, the eye care professional places drops into the eye to widen the pupil. This allows him or her to see more of the retina and look for signs of diabetic retinopathy. After the examination, close-up vision may remain blurred for several hours. Ophthalmoscopy is an examination of the retina in which the eye care professional: (1) looks through a device with a special magnifying lens that provides a narrow view of the retina, or (2) wearing a headset with a bright light, looks through a special magnifying glass and gains a wide view of the retina. Note that hand-held ophthalmoscopy is insufficient to rule out significant and treatable diabetic retinopathy. OCT is a scan similar to an ultrasound which is used to measure the thickness of the retina. It produces a cross section of the retina and can determine if there is any swelling or leakage. Tonometry is a standard test that determines the fluid pressure (intraocular pressure) inside the eye. Elevated pressure is a possible sign of glaucoma, another common eye problem in people with diabetes. Digital Retinal Screening Programs are systematic programs for the early detection of eye disease including diabetic retinopathy are becoming more common, such as in the UK, where all people with diabetes mellitus are offered retinal screening at least annually. This involves digital image capture and transmission of the images to a digital reading center for evaluation and treatment referral. See Vanderbilt Ophthalmic Imaging Center and the English National Screening Programme for Diabetic Retinopathy. Slit Lamp Biomicroscopy Retinal Screening Programs are systematic programs for the early detection of diabetic retinopathy using slit-lamp biomicroscopy. These exist either as a standalone scheme or as part of the Digital program (above) where the digital photograph was considered to lack enough clarity for detection and/or diagnosis of any retinal abnormality.

The eye care professional can look at the retina for early signs of the disease, such as: (1) leaking blood vessels, (2) retinal swelling, such as macular edema, (3) pale, fatty deposits on the retina (exudates)—signs of leaking blood vessels, (4) damaged nerve tissue (neuropathy), and (5) any changes in the blood vessels. If the doctor suspect macular edema, he or she can perform a test called fluorescein angiography. In this test, a special dye is injected into the arm. Pictures are then taken as the dye passes through the blood vessels in the retina. This test allows the doctor to find the leaking blood vessels and areas of non-perfusion.

Treatments for diabetic retinopathy include laser surgery, injection of triamcinolone into the eye, and vitrectomy. Laser photocoagulation can be used in two scenarios for the treatment of diabetic retinopathy. Panretinal photocoagulation, or PRP (also called scatter laser treatment), is used to treat proliferative diabetic retinopathy (PDR). The goal is to create 1,000-2,000 burns in the retina with the hope of reducing the retina's oxygen demand, and hence the possibility of ischemia. In treating advanced diabetic retinopathy, the burns are used to destroy the abnormal blood vessels that form in the retina. This has been shown to reduce the risk of severe vision loss for eyes at risk by 50%.

Before the laser, the ophthalmologist dilates the pupil and applies anesthetic drops to numb the eye. In some cases, the doctor also can numb the area behind the eye to prevent any discomfort. The patient sits facing the laser machine while the doctor holds a special lens to the eye. The physician can use a single spot laser or a pattern scan laser for two dimensional patterns such as squares, rings and arcs. During the procedure, the patient may see flashes of light. These flashes may eventually create an uncomfortable stinging sensation for the patient. After the laser treatment, patients should be advised not to drive for a few hours while the pupils are still dilated. Vision can remain a little blurry for the rest of the day, though there should not be much pain in the eye.

Rather than focus the light on a single spot, the eye care professional can make hundreds of small laser burns away from the center of the retina, a procedure called scatter laser treatment or panretinal photocoagulation. The treatment shrinks the abnormal blood vessels. Patients can lose some of their peripheral vision after this surgery, but the procedure saves the rest of the patient's sight. Laser surgery can also slightly reduce color and night vision.

A person with proliferative retinopathy will always be at risk for new bleeding as well as glaucoma, a complication from the new blood vessels. This means that multiple treatments can be required to protect vision.

Triamcinolone is a long acting steroid preparation. When injected in the vitreous cavity, it results in a decrease in the macular edema (thickening of the retina at the macula) caused due to diabetic maculopathy, along with an increase in the visual acuity. The effect of triamcinolone is transient, lasting up to three months, and necessitating repeated injections for maintaining the beneficial effect. Complications of intravitreal injection of triamcinolone include cataract, steroid induced glaucoma and endophthalmitis.

Instead of laser surgery, some people need an eye operation called a vitrectomy to restore vision. A vitrectomy is performed when there is a lot of blood in the vitreous. It involves removing the cloudy vitreous and replacing it with a balanced salt solution. Because the vitreous is mostly water, there should be no change in vision when the balanced salt solution replaces the vitreous.

Studies show that people who have a vitrectomy soon after a large hemorrhage are more likely to protect their vision than someone who waits to have the operation. Early vitrectomy is especially effective in people with insulin-dependent diabetes, who may be at greater risk of blindness from a hemorrhage into the eye.

3. Retinopathy of Prematurity

Also provided is a method of treating or preventing retinopathy of prematurity (ROP) in a subject comprising: identifying a subject having or at risk of having said ROP, and administering to the retina of the subject a polypeptide disclosed herein.

Retinopathy of prematurity (ROP), previously known as retrolental fibroplasia (ALF), is a disease of the eye that affects prematurely born babies. It is thought to be caused by disorganized growth of retinal blood vessels which can result in scarring and retinal detachment. ROP can be mild and may resolve spontaneously, but can lead to blindness in serious cases. As such, all preterm babies are at risk for ROP, and very low birth weight is an additional risk factor. Both oxygen toxicity and relative hypoxia can contribute to the development of ROP.

Normally, maturation of the retina proceeds in utero and at term, the mature infant has fully vascularized retina. However, in preterm infants, the retina is often not fully vascularized. ROP occurs when the development of the retinal vasculature is arrested and then proceeds abnormally. The key disease element is fibrovascular proliferation. This is growth of abnormal new vessels that may regress, but frequently progresses. Associated with the growth of these new vessels is fibrous tissue (scar tissue) that may contract to cause retinal detachment. Multiple factors can determine whether the disease progresses, including overall health, birth weight, the stage of ROP at initial diagnosis, and the presence or absence of "plus disease". Supplemental oxygen exposure, while a risk factor, is not the main risk factor for development of this disease. Restricting supplemental oxygen use does not necessarily reduce the rate of ROP, and may raise the risk of other hypoxia-related systemic complications.

Patients with ROP are at greater risk for strabismus, glaucoma, cataracts and myopia later in life, and should be examined yearly to help prevent and treat these conditions.

Following pupillary dilation using eye drops, the retina is examined using a special lighted instrument (an indirect ophthalmoscope). The peripheral portions of the retina are pushed into view using scleral depression. Examination of the retina of a premature infant is performed to determined how far the retinal blood vessels have grown (the zone), and whether or not the vessels are growing flat along the wall of the eye (the stage). Retinal vascularization is judged to be complete when vessels extend to the ora serrata. The stage of ROP refers to the character of the leading edge of growing retinal blood vessels (at the vascular-avascular border). The stages of ROP disease have been defined by the International Classification of Retinopathy of Prematurity (ICROP).

Retinal examination with scleral depression is generally recommended for patients born before 30-32 weeks gestation, with birthweight 1500 grams or less, or at the discretion of the treating neonatologist. The initial examination is usually performed at 4-6 weeks of life, and then repeated every 1-3 weeks until vascularization is complete (or until disease progression mandates treatment).

In older patients the appearance of the disease is less well described but includes the residua of the ICROP stages as well as secondary retinal responses.

The most difficult aspect of the differential diagnosis can arise from the similarity of two other diseases: Familal Exudative Vitreoretinopathy, which is a genetic disorder that also disrupts the retinal vascularization in full-term infants, and Persistent Fetal Vascular Syndrome, also known as Persistent Hyperplastic Primary Vitreous, that can cause a traction retinal detachment difficult to differentiate but typically unilateral. In some aspects, the disclosed method can be used to treat Familal Exudative Vitreoretinopathy. In some aspects, the disclosed method can be used to treat Persistent Fetal Vascular Syndrome.

ICROP uses a number of parameters to describe the disease. They are location of the disease into zones (1, 2, and 3), the circumferential extent of the disease based on the clock hours (1-12), the severity of the disease (stage 1-5) and the presence or absence of "Plus Disease". Each aspect of the classification has a technical definition.

The zones are centered on the optic nerve. Zone 1 is the posterior zone of the retina, defined as the circle with a radius extending from the optic nerve to double the distance to the macula. Zone 2 is an annulus with the inner border defined by zone 1 and the outer border defined by the radius defined as the distance from the optic nerve to the nasal ora serrata. Zone 3 is the residual temporal crescent of the retina.

The circumferential extent of the disease is described in segments as if the top of the eye were 12 on the face of a clock. For example one might report that there is stage 1 disease for 3 clock hours from 4 to 7 o'clock.

The Stages describe the ophthalmoscopic findings at the junction between the vascularized and avascular retina. Stage 1 is a faint demarcation line. Stage 2 is an elevated ridge. Stage 3 is extraretinal fibrovascular tissue. Stage 4 is sub-total retinal detachment. Stage 5 is total retinal detachment.

In addition, "Plus disease" can be present at any stage. It describes a significant level of vascular dilation and tortuosity observed at the posterior retinal vessels. This reflects the increase of blood flow through the retina.

Stages 1 and 2 do not lead to blindness. However, they can progress to the more severe stages. Threshold disease is defined as disease that has a 50% likelihood of progressing to retinal detachment. Threshold disease is considered to be present when stage 3 ROP is present in either zone T or zone II, with at least 5 continuous or 8 total clock hours of disease, and the presence of plus disease. Progression to stage 4 (partial retinal detachment), or to stage 5 (total retinal detachment), can result in substantial or total loss of vision for the infant.

In order to allow timely intervention, a system of monitoring is undertaken for infants at risk of developing ROP. These monitoring protocols differ geographically because the definition of high-risk is not uniform or perfectly defined. In the USA the consensus statement of experts is informed by data derived by clinical trials and published in Pediatrics 2006. They included infants with birthweights under 1500 grams or under 28 weeks gestation in most cases.

Peripheral retinal ablation is the mainstay of ROP treatment. The destruction of the avascular retina is performed with a solid state laser photocoagulation device, as these are easily portable to the operating room or neonatal ICU.

Cryotherapy, an earlier technique in which regional retinal destruction was done using a probe to freeze the desired areas, has also been evaluated in multi-center clinical trials as an effective modality for prevention and treatment of ROP. However, cryotherapy is no longer preferred for routine avascular retinal ablation in premature babies, due to the side effects of inflammation and lid swelling.

Scleral buckling and/or vitrectomy surgery can be considered for severe ROP (stage 4 and 5) for eyes that progress to retinal detachment. Few centers in the world specialize in this surgery, because of its attendant surgical risks and generally poor outcomes.

Intravitreal injection of bevacizumab (Avastin) has been reported as a supportive measure in aggressive posterior retinopathy of prematurity.

4. Vascular Permeability

"Vascular permeability" refers to the capacity of small molecules (ions, water, nutrients) or even whole cells (lymphocytes on their way to the site of inflammation) to pass through a blood vessel wall. Blood vessel walls are lined by a single layer of endothelial cells. The gaps between endothelial cells (cell junctions) are strictly regulated depending on the type and physiological state of the tissue.

Diseases and disorders characterized by undesirable vascular permeability include, for example, edema associated with brain tumors, ascites associated with malignancies, Meigs' syndrome, lung inflammation, nephrotic syndrome, pericardial effusion and pleural effusion. Thus, provided is a method of treating or preventing these or any other disease associated with an increase in vascular permeability or edema. For example, inhibiting edema formation should be beneficial to overall patient outcome in situations such as inflammation, allergic diseases, cancer, cerebral stroke, myocardial infarction, pulmonary and cardiac insufficiency, renal failure, trauma, and retinopathies. Furthermore, as edema is a general consequence of tissue hypoxia, it can also be concluded that inhibition of vascular leakage represents a potential approach to the treatment of tissue hypoxia. For example, interruption of blood flow by pathologic conditions (such as thrombus formation) or medical intervention (such as cardioplegia, organ transplantation, and angioplasty) could be treated both acutely and prophylactically using inhibitors of vascular leakage.

Also provided is a method of treating or preventing ischemia/reperfusion injury following stroke and myocardial infarction. A deficit in tissue perfusion leads to persistent post-ischemic vasogenic edema, which develops as a result of increased vascular permeability. Tissue perfusion is a measure of oxygenated blood reaching the given tissue due to the patency of an artery and the flow of blood in an artery. Tissue vascularization may be disrupted due to blockage, or alternatively, it may result from the loss of blood flow resulting from blood vessel leakage or hemorrhage upstream of the affected site. The deficit in tissue perfusion during acute myocardial infarction, cerebral stroke, surgical revascularization procedures, and other conditions in which tissue vascularization has been disrupted, is a crucial factor in outcome of the patient's condition. Edema can cause various types of damage including vessel collapse and impaired electrical function, particularly in the heart. Subsequent reperfusion, however, can also cause similar damage in some patients, leading to a treatment paradox. While it is necessary, to unblock an occluded blood vessel or to repair or replace a damaged blood vessel, the ensuing reperfusion can, in some cases, lead to further damage. Likewise, during bypass surgery, it is necessary to stop the heart from beating and to have the patient hooked to a heart pump. Some patients who undergo bypass surgery, for example, may actually experience a worsening of condition ("post-pump syndrome"), which may be the result of ischemia during cessation of cardiac function during surgery. An arterial blockage may cause a reduction in the flow of blood, but even after the blockage is removed and the artery is opened, if tissue reperfusion fails to occur, further tissue damage may result. For example, disruption of a clot may trigger a chain of events leading to loss of tissue perfusion, rather than a gain of perfusion.

5. Angiogenesis

Angiogenesis and angiogenesis related diseases are closely affected by cellular proliferation. As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, fetal and embryonal development and formation of the corpus luteum, endometrium and placenta. The term "endothelium" is defined herein as a thin layer of flat cells that lines serous cavities, lymph vessels, and blood vessels. These cells are defined herein as "endothelial cells". The term "endothelial inhibiting activity" means the capability of a molecule to inhibit angiogenesis in general. The inhibition of endothelial cell proliferation also results in an inhibition of angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout' off the parent blood vessel, where the endothelial cells undergo mitosis and proliferate. The endothelial sprouts merge with each other to form capillary loops, creating the new blood vessel.

New blood vessels may also form in part by vasculogenesis. Vasculogenesis is distinguished from angiogenesis by the source of the endothelial cells. Vasculogenesis involves the recruitment of endothelial progenitor cells known as angioblasts. These angioblasts can come from the circulation or from the tissue. Vasculogenesis is regulated by similar signaling pathways as angiogenesis. Thus, the term "angiogenesis" is used herein interchangeably with vasculogenesis such that a method of modulating angiogenesis can also modulate vasculogenesis.

Provide herein is a method of modulating angiogenesis in a tissue, comprising delivering into endothelial cells of the tissue a composition comprising a polypeptide disclosed herein. Also provided is a method of modulating angiogenesis in a tissue, comprising delivering into endothelial cells of the tissue a composition comprising a nucleic acid disclosed herein. Also provided is a method of modulating angiogenesis in a tissue, comprising administering to the tissue a composition comprising a vector disclosed herein, wherein the vector transduces an endothelial cell. In some aspects of the disclosed methods, angiogenesis is promoted to increase vascularization. In some aspects of the disclosed methods, angiogenesis is inhibited to reduce vascularization of a tissue.

For example, persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic dependent, angiogenic-associated, or angiogenic-related diseases. These diseases are a result of abnormal or undesirable cell proliferation, particularly endothelial cell proliferation.

Thus, the methods and compositions described herein are useful for treating human and animal diseases and processes mediated by abnormal or undesirable endothelial cell proliferation, including, but not limited to, hemangioma, solid tumors, leukemia, central retinal vein occlusion, branch vein occlusion, retinal neovascularization secondary to carotid insufficiency, sickle cell retinopathy status post radiation retinitus, telangiectasia psoriasis scleroderma, pyogenic granuloma, myocardial angiogenesis, plaque neovascularization, coronary collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation. The method and composition are particularly useful for treating angiogenesis-related disorders and diseases by inhibiting angiogenesis. Other uses for the disclosed peptides are disclosed in International Patent Publication WO/2006/069181, which is incorporated by reference herein in its entirety for the teaching of these methods.

6. Administration

The disclosed compounds and compositions can be administered in any suitable manner. The manner of administration can be chosen based on, for example, whether local or systemic treatment is desired, and on the area to be treated. For example, the compositions can be administered orally, parenterally (e.g., by injection to target specific tissues, organs and parts of the body, intravenous, intraocular, intra-tumor, intrajoint, intracardiac, intraperitoneal, or intramuscular injection), by inhalation, extracorporeally, topically (including transdermally, ophthalmically, vaginally, rectally, intranasally) or the like.

The route of administration and the dosage regimen will be determined by skilled clinicians, based on factors such as the exact nature of the condition being treated, the severity of the condition, and the age and general physical condition of the patient. Specific routes of administration to the eye may include topical application (such as by eyedrops, creams or erodible formulations to be placed under the eyelid), intraocular injection into the aqueous or the vitreous humor, injection into the external layers of the eye, such as via subconjunctival injection or subtenon injection, parenteral administration or via oral routes. For example, provided are eye drops comprising one or more of the herein disclosed compositions.

The herein disclosed compositions, including peptides, can be combined with a targeting protein, compound, nanotechnological device, or cell that can target the peptide to the site of the pathology. For example, provided is an antibody linked to one or more peptides disclosed herein, wherein the antibody selectively homes and binds to tissue at the site of the pathology. Also provided is an aptamer linked to one or more peptides disclosed herein, wherein the aptamer selectively homes and binds to tissue at the site of the pathology. Also provided is a cell linked to one or more peptides disclosed herein, wherein the cell selectively homes and binds to tissue at the site of the pathology.

Administration can further be by way of intraocular implant. For example, the implant can deliver a regular dose of the ACT peptide to the anterior chamber, posterior chamber, retina, macula, retinal pigment epithelium, choroid, Bruch's membrane, vitreous, cornea, or lens. Thus, provided herein is a method comprising introducing an intraocular implant into the eye of a subject, wherein the intraocular implant releases one or more peptides disclosed herein to the anterior chamber, posterior chamber, retina, macula, retinal pigment epithelium, choroid, Bruch's membrane, vitreous, cornea, or lens.

Ophthalmic products for topical use may be packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquatemium-1, or other agents known to those skilled in the art. Such preservatives are typically employed at a level of from 0.001 to 1.0% weight/volume ("% w/v"). Such preparations may be packaged in dropper bottles or tubes suitable for safe administration to the eye, along with instructions for use.

When the ophthalmic compositions disclosed herein are administered during intraocular surgical procedures, such as through retrobulbar or periocular injection and intraocular perfusion or injection, the use of balanced salt irrigating solutions as vehicles are most preferred. BSS Sterile Irrigating Solution and BSS Plus® Sterile Intraocular Irrigating Solution (Alton Laboratories, Inc., Fort Worth, Tex. USA) are examples of physiologically balanced intraocular irrigating solutions. The latter type of solution is described in U.S. Pat. No. 4,550,022 (Garabedian, et al.), the entire contents of which are hereby incorporated in the present specification by reference. Retrobulbar and periocular injections are known to those skilled in the art and are described in numerous publications including, for example, Ophthalmic Surgery: Principles of Practice, Ed., G. L. Spaeth. W. B. Sanders Co., Philadelphia, Pa., U.S.A., (1990).

The ophthalmic compositions may also be used as an adjunct to ophthalmic surgery, such as by intra vitreal or subconjunctival injection following ophthalmic surgery. The compounds may be used for acute treatment of temporary conditions, or may be administered chronically, especially in the case of degenerative disease. The ophthalmic compositions may also be used prophylactically, especially prior to ocular surgery or noninvasive ophthalmic procedures or other types of surgery.

Pharmaceutical compositions (also referred to herein as "ophthalmic compositions") that include a peptide disclosed herein and a pharmaceutically acceptable carrier may be packed with instructions for use of the pharmaceutical composition for treatment and/or prevention of for example, macular degeneration. The ingredients may be packaged together in the form of a kit.

As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The exact amount of the compositions required can vary from subject to subject, depending on the species, age, weight and general condition of the subject, the severity of the macular degeneration, the particular nucleic acid or vector used, its mode of administration and the like. Thus, it is not possible to specify an exact amount for every composition. However, an appropriate amount can be determined by one of ordinary skill in the art using only routine experimentation given the teachings herein. Thus, effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage can vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual doctor in the event of any counterindications. Dosage can vary, and can be administered in one or more dose administrations daily, for one or several days. Guidance can be found in the literature for appropriate dosages for given classes of pharmaceutical products. The range of dosage largely depends on the application of the compositions herein, severity of condition, and its route of administration.

For example, in applications as a laboratory tool for research, the ACT peptide compositions can be used in doses as low as 0.01% w/v. The dosage can be as low as 0.02% w/v and as high as 5% w/v. Significantly higher concentrations of the compositions by themselves or in combination with other compounds may be used in applications. Recommended upper limits of dosage for parenteral routes of administration for example intramuscular, intracerebral, intracardicardiac and intraspinal could be up to 1% w/v or v/v. This upper dosage limit may vary by formulation, depending for example on how the polypeptide(s) is combined with other agents promoting its action or acting in concert with the polypeptide(s).

For continuous delivery of the provided polypeptides, for example, in combination with an intravenous drip, upper limits of 0.01 g/Kg body weight over time courses determined by the doctor based on improvement in the condition can be used. In another example, upper limits of concentration of the provided nucleic acids delivered topically would be 5-10 µg/cm$^2$. This would be repeated at a frequency determined by the Doctor based on improvement. In another example, upper limits of concentration of the provided nucleic acids delivered internally for example, intramuscular, intracerebral, intracardicardiac and intraspinal would be 50-100 µg/ml of solution. Again, the frequency would be determined by the Doctor based on improvement.

Viral vectors remain highly experimental tools that nonetheless show considerable potential in clinical applications. As such, caution is warranted in calculation of expected dosage regimes for viral vectors and will depend considerably on the type of vector used. For example, retroviral vectors infect dividing cells such as cancer cells efficiently, intercalating into the host cell genome and continuing expression of encoded proteins indefinitely. Typical dosages of retroviruses in an animal model setting are in the range of $10^7$ to $10^9$ infectious units per ml. By contrast, adenoviruses most efficiently target post-mitotic cells, but cells are quickly eliminated by the host immune system or virus is eventually lost if infected cells resume proliferation and subsequently dilute the viral episomal DNA. Indeed, this transient time course of infection may be useful for short-term delivery of the composition described herein in certain clinical situations. In animal models, concentrations of $10^8$-$10^{11}$ infectious units per ml of adenovirus are typical for uses in research. Dose ranges of vectors based on data derived from animal models would be envisaged to be used eventually in clinical setting(s), pending the development of pharmaceutically acceptable formulation(s).

Following administration of a disclosed composition, such as a polypeptide, the efficacy of the therapeutic composition can be assessed in various ways well known to the skilled practitioner. For instance, one of ordinary skill in the art will understand that a composition, such as a polypeptide, disclosed herein is efficacious in treating or preventing macular degeneration in a subject by observing that the composition can reduce neovascularization, or improve vision. Methods for measuring these criteria are known in the art and discussed herein.

7. Organ and Tissue Transplantation

Organ transplantation is the moving of an organ from one body to another or from a donor site to another location on the person's own body, to replace the recipient's damaged or absent organ.

Organs and/or tissues that are transplanted within the same person's body are called autografts. Sometimes an autograft is done to remove the tissue and then treat it or the person before returning it (examples include stem cell autograft and storing blood in advance of surgery).

Organs and/or tissues that are transplanted between two genetically non-identical members of the same species are called allografts. Allografts can either be from a living or cadaveric source. Most human tissue and organ transplants are allografts. Due to the genetic difference between the organ and the recipient, the recipient's immune system will identify the organ as foreign and attempt to destroy it, causing transplant rejection.

Isografts are a subset of allografts in which organs or tissues are transplanted from a donor to a genetically identical recipient (such as an identical twin). Isografts are differentiated from other types of transplants because while they are anatomically identical to allografts, they do not trigger an immune response.

A transplant of organs or tissue from one species to another is called a xenograft. An example is porcine heart valve transplant, which is quite common and successful. Another example is attempted piscine-primate (fish to non-human primate) transplant of islet (i.e. pancreatic or insular) tissue. Xenotransplantion is often an extremely dangerous type of transplant because of the increased risk of non-compatibility, rejection, and disease carried in the tissue.

Organs that can be transplanted are the heart, kidneys, liver, lungs, pancreas, intestine, and thymus. Tissues include bones, tendons (both referred to as musculoskeletal grafts), cornea, skin, heart valves, nerves and veins. Worldwide, the kidneys are the most commonly transplanted organs, followed by the liver and then the heart. Cornea and musculoskeletal grafts are the most commonly transplanted tissues; these outnumber organ transplants by more than tenfold.

Organ donors may be living, brain dead, or dead via circulatory death. Tissue may be recovered from donors who die of circulatory death, as well as of brain death—up to 24 hours past the cessation of heartbeat. Unlike organs, most tissues (with the exception of corneas) can be preserved and stored for up to five years, meaning they can be "banked".

Organ preservation solutions are known in the art and include, without limitation, Belzer's University of Wisconsin solution (UW solution), Euro-Collins solution, Ross-Marshall citrate solution, Bretschneider histidine tryptophan ketoglutarate solution, phosphate buffered sucrose solution, Celsior solution, and Kyoto ET solution.

In some embodiments, the compositions provided herein are organ preservation solutions comprising a polypeptide comprising the carboxy-terminal amino acid sequence of an alpha connexin, or a conservative variant thereof (e.g., a polypeptide having an amino acid sequence according to SEQ ID NO: 1, 2, 3, 4, or 5). For example, in some embodiments, the compositions provided herein comprise UW solution and a polypeptide having an amino acid sequence according to SEQ ID NO: 2. In some embodiments, the solution comprises, for example, a polypeptide comprising the carboxy-terminal amino acid sequence of an alpha connexin, or a conservative variant thereof (e.g. SEQ ID NO: 1, 2, 3, 4, or 5), potassium, sodium, magnesium, lactobionate, phosphate, sulphate, raffinose, adenosine, allopurinol, glutathione, insulin, dexamethasone, hydroxyethyl starch (HES), and/or Bactrim. In further embodiments, UW solution comprises about 135 mmol/L potassium, about 35 mmol/L sodium, about 5 mmol/L magnesium, about 100 mmol/L lactobionate, about 25 mmol/L phosphate, about 5 mmol/L sulphate, about 30 mmol/L raffinose, about 5 mmol/L adenosine, about 1 mmol/L allopurinol, about 3 mmol/L glutathione, about 100 U/L insulin, about 8 mg/L dexamethasone, about 50 g/L HES, and/or about 0.5 ml/L Bactrim. The skilled artisan will recognize that any organ or tissue preservation solution known in the art can be used in the methods and compositions disclosed herein. Accordingly, the alpha connexin polypeptides provided herein can be added to any organ or tissue preservation solution known in the art in order to improve the preservation properties of the organ or tissue preservation solution.

In some embodiments, the polypeptide is present in the organ or tissue preservation solution at a concentration of about 1 to about 1000 µM, or about 10 to about 500 µM, or about 25 to about 250 µM, or about 50 to about 150 µM, or about 100 µM.

In some embodiments, the present disclosure provides compositions comprising one or more organ (e.g. heart, kidneys, liver, lungs, pancreas, intestine, and thymus) or tissue for transplantation into a recipient, and a polypeptide as provided herein (e.g., a polypeptide comprising the carboxy-terminus of an alpha connexin, or a conservative variant thereof). In further embodiments, the composition comprises one or more organ or tissue, an alpha connexin polypeptide as provided herein, and an organ preservation solution.

In one aspect, the present disclosure provides compositions and methods for preserving an organ for organ transplantation comprising incubating the organ with a solution comprising a polypeptide comprising the carboxy-terminal amino acid sequence of an alpha connexin, or a conservative variant thereof, as provided herein. In some embodiments, the present disclosure provides compositions and methods for preserving an organ for organ transplantation comprising perfusing the organ with a solution comprising a polypeptide comprising the carboxy-terminal amino acid sequence of an alpha connexin, or a conservative variant thereof, as provided herein. In some embodiments, the present disclosure provides compositions and methods for preserving a tissue for tissue transplantation, comprising incubating the tissue with a solution comprising a polypeptide comprising the carboxy-terminal amino acid sequence of an alpha connexin, or a conservative variant thereof, as provided herein.

In some embodiments, the methods and solutions provided herein inhibit endothelial and/or epithelial cellular injury. In some embodiments, the methods and solutions provided herein inhibit mitochondrial oxidant production. In some embodiments, the polypeptide inhibits inflammation. In some embodiments, the polypeptide inhibits pro-inflammatory cytokine release. Pro-inflammatory cytokines are known in the art and include, for example, IL-8, IFNγ, TNF, IL-12, IL-6, IL-1β, IL-2, and IL-17.

8. Fluid Replacement

In some embodiments, the disclosure provides methods and compositions for administration to subjects undergoing dialysis, surgical and other medical procedures or requiring re-hydration or fluid replenishment following blood loss, comprising administering to the subject an isolated polypeptide comprising the carboxy-terminal amino acid sequence of an alpha connexin, or a conservative variant thereof. In some embodiments, the present disclosure provides compositions and methods for medical imaging procedures such as, for example, nuclear medicine techniques, magnetic resonance imaging, and computed tomography. Radioactive or fluorescent microspheres comprising the polypeptides provided herein can also be prepared and administered to subjects.

C. Methods of Making the Compositions

The compositions disclosed herein and the compositions necessary to perform the disclosed methods can be made using any method known to those of skill in the art for that particular reagent or compound unless otherwise specifically noted.

For example, the provided nucleic acids can be made using standard chemical synthesis methods or can be produced using enzymatic methods or any other known method. Such methods can range from standard enzymatic digestion followed by nucleotide fragment isolation (sec for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

One method of producing the disclosed polypeptides, such as SEQ ID NO:2, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a protein, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathriam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Disclosed are processes for making the compositions as well as the intermediates leading to the compositions. There are a variety of methods that can be used for making these compositions, such as synthetic chemical methods and standard molecular biology methods. It is understood that the methods of making these and the other disclosed compositions are specifically disclosed. Disclosed are nucleic acid molecules produced by the process comprising linking in an operative way a nucleic acid encoding a polypeptide disclosed herein and a sequence controlling the expression of the nucleic acid. Disclosed are cells produced by the process of transforming the cell with any of the herein disclosed nucleic acids. Disclosed are any of the disclosed peptides produced by the process of expressing any of the herein disclosed nucleic acids. Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate. Also disclose are animals produced by the process of adding to the animal any of the cells disclosed herein.

D. Definitions

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents.

It must be noted that as used herein and in the appended claims, the singular forms "a," "an," and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

The term "therapeutically effective" means that the amount of the composition used is of sufficient quantity to ameliorate one or more causes or symptoms of a disease or disorder. Such amelioration only requires a reduction or alteration, not necessarily elimination. The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

By "treat" or "treatment" is meant a method of reducing the effects of a disease or condition. Treatment can also refer to a method of reducing the underlying cause of the disease or condition itself rather than just the symptoms. The treatment can be any reduction from native levels and can be but is not limited to the complete ablation of the disease, condition, or the symptoms of the disease or condition. For example, a disclosed method for treating macular degeneration is considered to be a treatment if there is a 10% reduction in one or more symptoms of the disease in a subject with the disease when compared to native levels in the same subject or control subjects. Thus, the reduction can be a 10, 20, 30, 40, 50, 60, 70, 80, 90, 100%, or any amount of reduction in between as compared to native or control levels.

By "prevent" or other forms of prevent means to stop a particular characteristic or condition from developing or from progressing. Prevent does not require comparison to a control as it is typically more absolute than, for example, reduce or inhibit. As used herein, something could be reduced but not inhibited or prevented, but something that is reduced could also be inhibited or prevented. It is understood that where reduce, inhibit or prevent are used, unless specifically indicated otherwise, the use of the other two words is also expressly disclosed. Thus, if inhibition of permeability is disclosed, then reduction and prevention of permeability are also disclosed.

As used herein, "subject" includes, but is not limited to, animals, plants, bacteria, viruses, parasites and any other organism or entity that has nucleic acid. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to," and is not intended to exclude, for example, other additives, components, integers or steps.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

E. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

As shown in FIG. 1, the alpha connexin carboxy-terminal (ACT) polypeptide ACT1 prevents VEGF-induced deterioration of TER in ARPE-19 cells. Trans-epithelial resistance (TER) measurements, using ARPE19 cell (immortalized human RPE cells) monolayers revealed that VEGF leads to rapid deterioration, which was blocked by pre-treating the cells with the ACT peptide. Thus, while not wishing to be bound by theory, stabilizing the tight junction proteins with the ACT peptide can prevent loss of tight-junction disintegration and thus damage to RPE/Bruch's membrane.

ACT1 Peptide contains an amino terminal cell internalization sequence. Together with a mild detergent that is used in ocular applications, Brij-78 the antenapedia sequence assists in permeation of ACT1 into interior fluids and tissues of the eye. In some aspects, the ability of ACT1 to enter the internal fluids and tissues of eye is a mode of action of ACT1 in treating diseases of the eye such as macular degeneration.

i. Results

Figure 2:
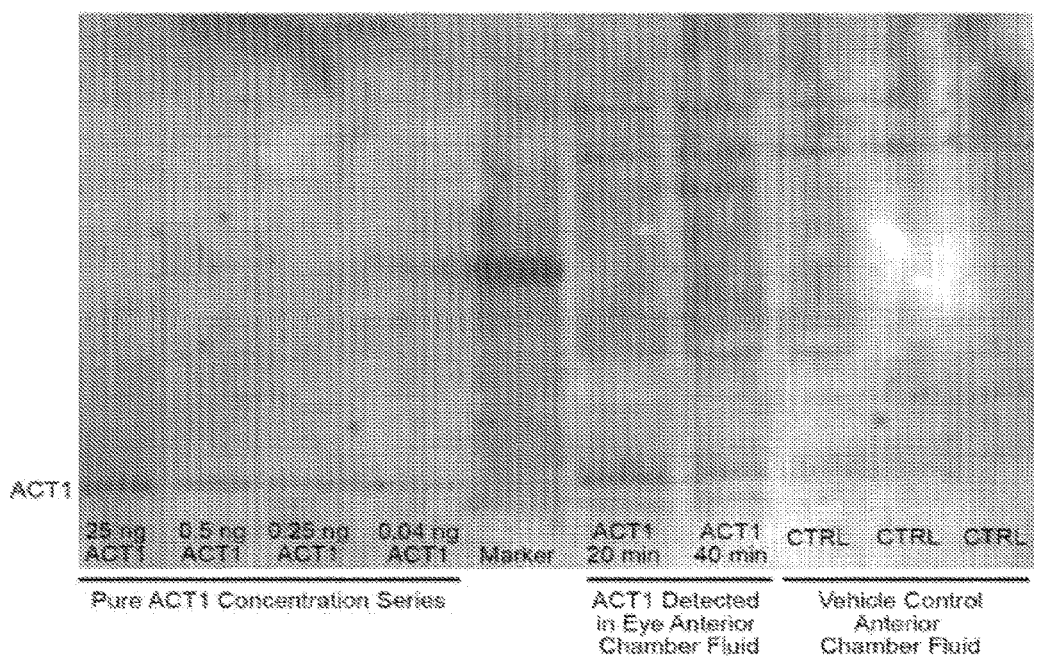
FIG. 2 shows by Western blot a concentration series of 25-0.04 ng/μL of pure ACT1 peptide. ACT1 was detectable in the eye anterior chamber fluid at levels in excess of the highest concentration of pure peptide. No peptide was observed in the anterior chamber fluid control eyes receiving the vehicle control 0.05% Brij-78 solution.

Application of ACT1 peptide in a solution containing 0.05% Brij-78 to the cornea of mouse eyes resulted in a detectable level of ACT1 in the internal fluids of the anterior chamber (i.e., the aqueous humor) 20 and 40 minutes post-application (FIG. 2). Lower levels of ACT1 could also be detected by Western blotting in fluid from the posterior chamber of eye 20 and 40 minutes, i.e., the vitreous humor.

Following application of ACT1 in a solution containing 0.05% Brij-78 to the cornea of mouse eyes, ACT1 was detectable in the retinal pigment epithelial layer of eye minutes post-application. Moreover, ACT1 was immunohistochemically detected in the retinal pigment epithelial layer of eyes exposed to the peptide, but not to the vehicle control solution via corneal application.

ii. Methods:

Three CD1 mice were anesthetized by IP injection of 0.2 mL Salazine/ketamine. 10 µL of 1 mM ACT1 peptide dissolved in a solution containing normal saline and 0.05% Brij-78 was gently dripped onto the corneal surface of both eyes and allowed to permeate for 20 or 40 min. 0.05% Brij-78 in normal saline was used on a control mouse. The mice were sacrificed in a $CO_2$ chamber and cervically dislocated at 20, 40 min (the control mouse sacrificed at 20 min). The eyes were removed and rinsed in PBS. A small incision was made in the anterior chamber and the aqueous humor (~10 µL) was transferred to tube and flash frozen in a dry ice ethanol bath. The total sample was dissolved in 2× samples loading buffer and loaded on a 10-20% Tris-Tricine gel. Gel was transferred to a PDVF membrane and stained using RBT Sigma anti-CX43 CT antibody (1:10000) and a goat anti-RBT AP secondary (1:15000) to reveal the ACT1 band at <10 kDa.

Application of ACT1 to the cornea in Brij-78 was the same as described above. After sacrifice the mouse eyes were removed, washed in PBS briefly, and transferred to 5% Paraformaldehyde overnight. The eyes were embedded in paraffin, sectioned, and stained with Sigma Rbt anti-Cx43, streptavidin and Hoechst stain and placed at 4 degrees overnight. As disclosed herein, ACT1 is detectable in the interior fluids and tissues of the eye following a simple corneal exposure.

2. Example 2

Figure 3:
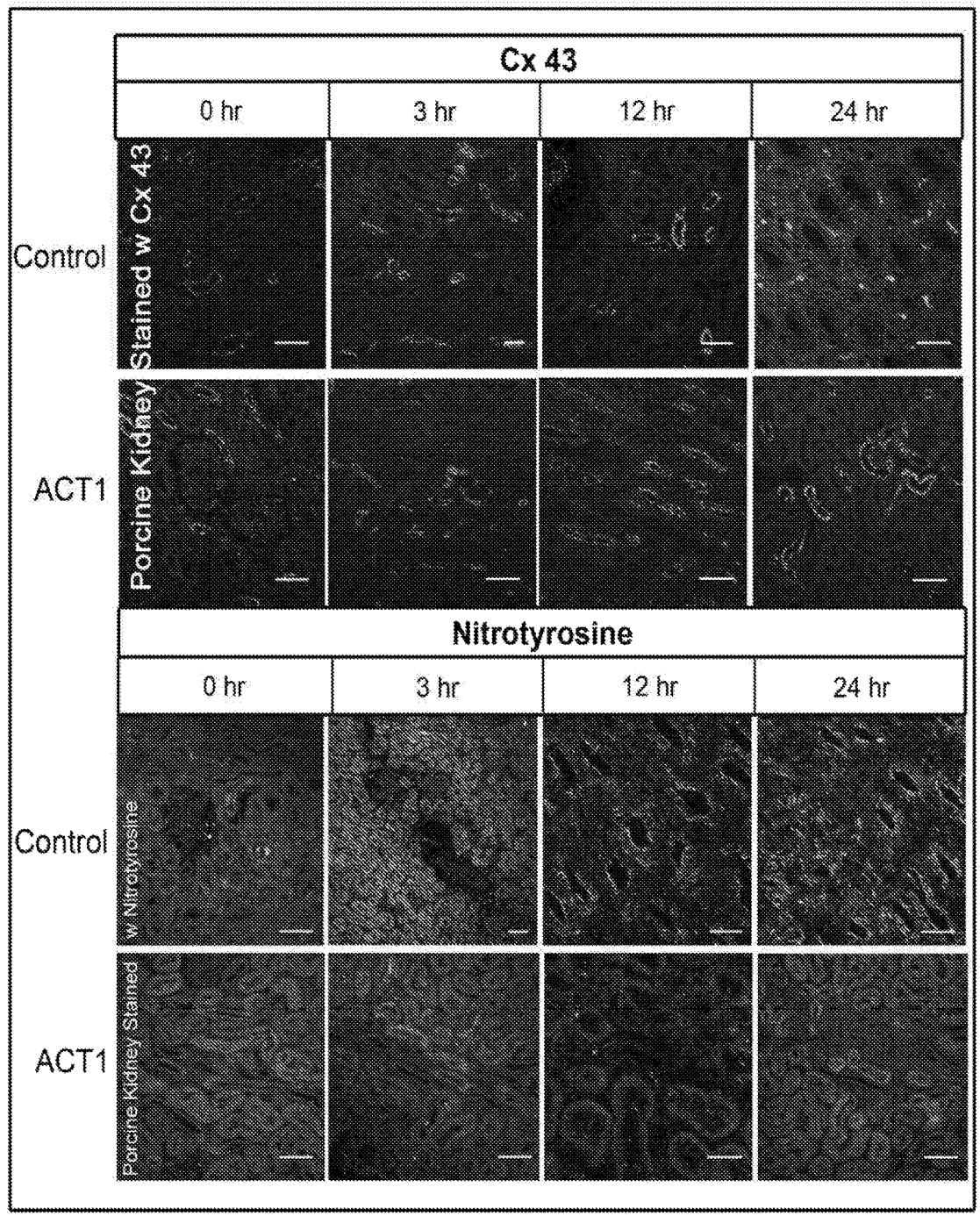
FIG. 3 shows representative sections of matched (same donor) 100 μM ACT1 peptide treated and control kidneys at 0, 3, 12 and 24 h of cold ischemia stained for Cx43 and nitrotyrosine. Scale bars=100 μm.

As shown in FIG. 3, ACT1 peptide stabilizes gap junctions (Cx43) and minimizes mitochondrial oxidant production (nitrotyrosine) and apoptosis (TUNEL and caspase) in porcine kidney models of cold ischemia.

i. Results

Punctate Cx43 staining in the membrane (gap junctions) were preserved in ACT1 peptide-treated kidneys and early control biopsies, while at 24 h Cx43 staining became more diffuse and appeared to localize to the cytoplasm of cells in the control kidneys. The 12 and 24 h sections demonstrated intense, localized nitrotyrosine staining in the apical and basolateral areas of control kidney cells in comparison to the ACT1 peptide-treated samples. There were no changes in nitrotyrosine staining in the presence of ACT1 peptide or in time zero control biopsies that were not subjected to cold ischemia. Apoptotic cells were also observed in the 24 h control (data not shown).

ii. Methods:

These studies were conducted using kidneys procured from 2 standard criteria donor pigs. The organs were flushed via the aorta with preservation solution after 10 minutes of warm ischemia post-mortem. Biopsies were taken prior to treatment. The kidneys were then flushed with either cold Belzer's solution (control) or the same solution containing 100 µm ACT1 peptide, and stored in the respective solutions on ice for 24 h. Biopsies were taken at regular intervals and sections were stained for Cx43 and nitrotyrosine.

3. Example 3

FIG. 4 shows the ability of ACT1 peptide to protect endothelial cells.

i. Results

Figure 4A:
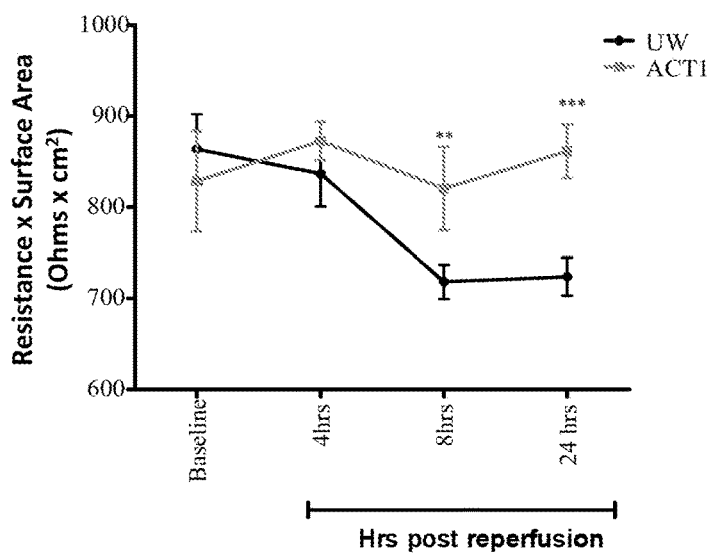
FIGS. 4A-4C show an in vitro model of cold storage and reperfusion. TEER for mouse cardiac endothelial (4A) and human respiratory epithelial (4B) cells at 4, 8 and 24 h post reperfusion. Note the significantly elevated TEER readings in ACT1 peptide treated cells demonstrating improved protection from ischemic insult. (4C) Elisa data demonstrating ACT1 pre-treatment significantly reduced pro-inflammatory cytokine (IL-8) release from endothelial cells. n=3 ##, **p<0.05.
Figure 4B:
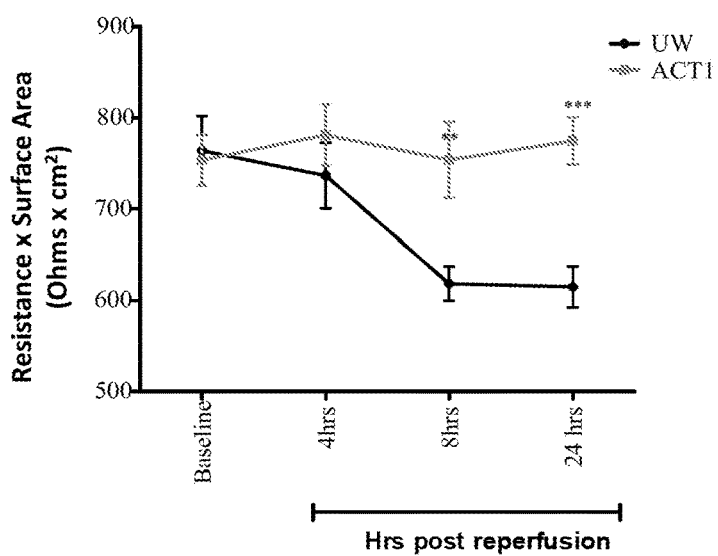
Figure 4C:
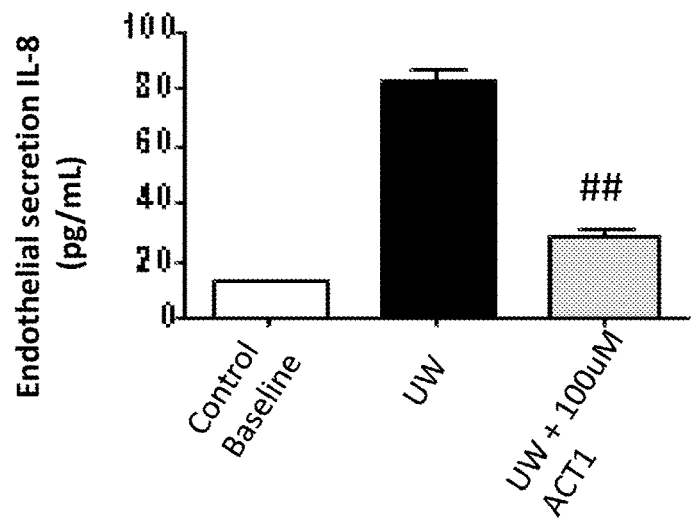

Storage of both epithelial and endothelial cell with Belzer's University of Wisconsin (UW) solution containing 100 µM ACT1 peptide significantly reduced cellular injury as compared to untreated controls (FIGS. 4A and 4B). Further, supernatants and cell lysates were collected to measure IL-8 secretion and MHC II expression. Treatment of either cell type with UW solution supplemented with ACT1 peptide was associated with significant reduction in IL-8 secretion (FIG. 4C) and MHC Class II expression (endothelial cells, data not shown).

ii. Methods:

These studies were conducted using a modification of the in vitro donor cold storage and reperfusion injury model (Casiraghi et al., 2009). Human umbilical vein endothelial cells (HUVECs) and mouse microvascular endothelial cells were grown to confluence on transwells and transendothelial resistance (TEER) was recorded. To model cold ischemia and reperfusion injury growth, media was removed from the cells and replaced with either ice cold UW solution or UW solution containing ACT1 peptide, and cultures were exposed to 6 h of hypoxia in a hypoxic chamber (Billups-Rothenberg, Del Mar, Calif.) at 4° C. Following hypoxic exposure, UW solution was removed, and to stimulate reperfusion, UW solution was replaced with fresh pre-warmed (37° C.) culture media, and cells were monitored for 24 h. TEER was measured at three time points post reperfusion as a marker of endothelial/epithelial cell death and dysfunction. A loss of electrical conductivity, as measured by TEER, across the cellular monolayer is associated with a loss of cell-cell communication (thus, gap junction and tight junction injury), cell injury, and a leaky endothelial cell lining. In vivo, this would translate as dysfunction of the cell layer and facilitate uncontrolled fluid trafficking, loss of vascular tone, reduced barrier function that would facilitate immune cell infiltration.

4. Example 4

FIG. 5 shows the impact of ACT1 peptide supplementation of UW solution in a small animal transplant model.

i. Results

ACT1 peptide therapy significantly reduces Evan's Blue sequestration into the transplanted heart as compared to controls, indicating that ACT1 peptide promotes gap junction and tight junction stability, and improved endothelial cell integrity.

ii. Methods:

Heart allograft transplants were performed between Balb/c donors to B6 recipients. Balb/c donor hearts were removed, perfused with UW solution and then static cold stored in either UW solution alone or UW solution supplemented with 100 µM ACT1 peptide for 6 h at 4° C. Following storage, hearts were implanted into B6 recipients using an abdominal heart transplant procedure. To assess the impact of ACT1 peptide augmented cold storage on heart vascular permeability/damage, recipients were injected with Evan's Blue Dye immediately following reperfusion. Hearts were then harvested for 30 mins post reperfusion and assayed for Evan's Blue uptake.

Figure 6A:
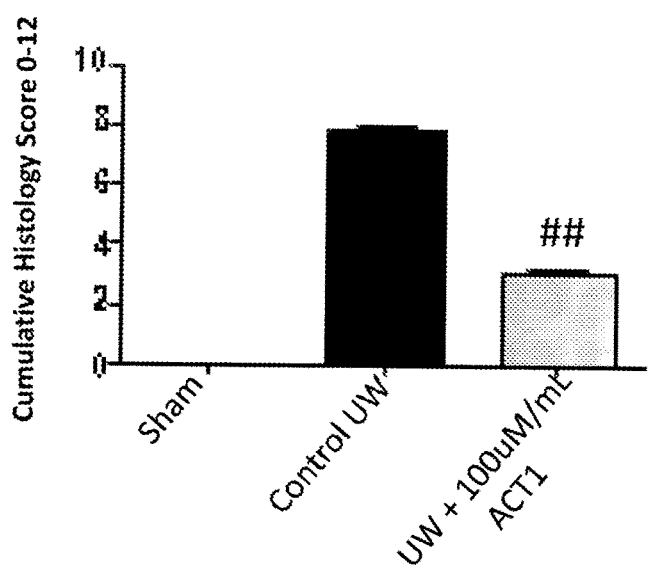
FIGS. 6A-6C show a mouse heterotopic heart allotransplantation model study. Balb/c donor hearts were static cold preserved in UW or UW+ACT1 peptide; 100 μM ACT1 peptide. 48 h post transplantation grafts and serum were removed for analysis. Histological injury score (6A), serum cardiac troponin I levels (6B) and neutrophil infiltration (6C) were all significantly reduced in grafts treated with ACT1 peptide. n=6, ##p<0.05.
Figure 6B:
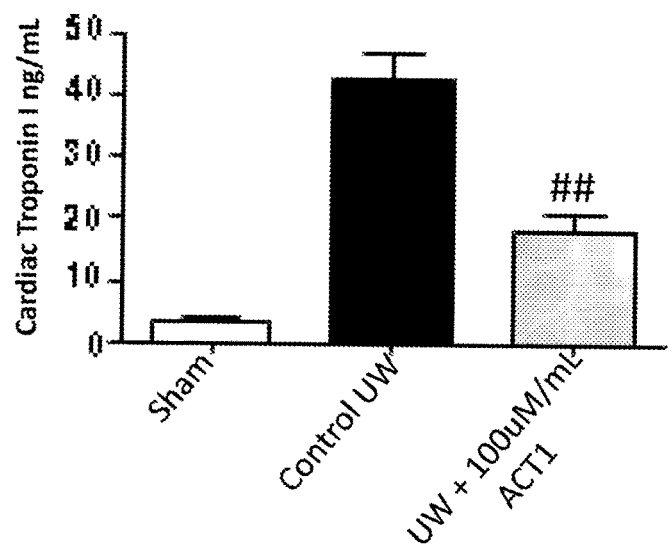

As shown in FIG. 6, ACT1 peptide treatment improved endothelial barrier function was associated with reduced ischemia reperfusion injury (IRI).

iii. Results

Figure 6C:
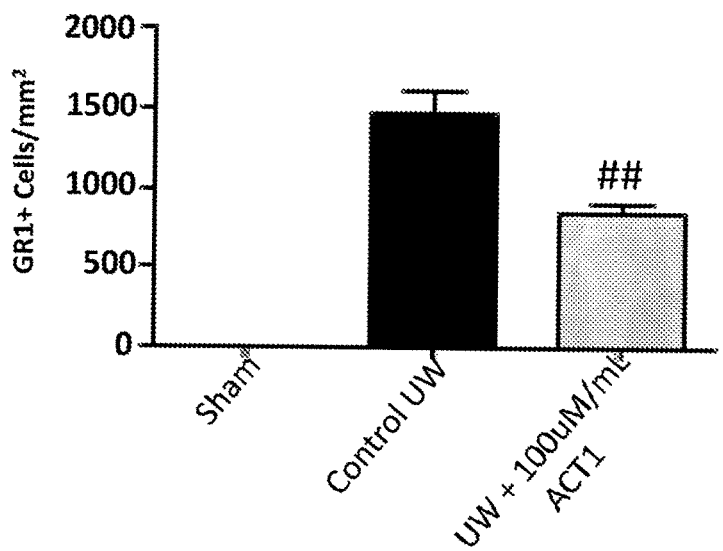
Figure 7:
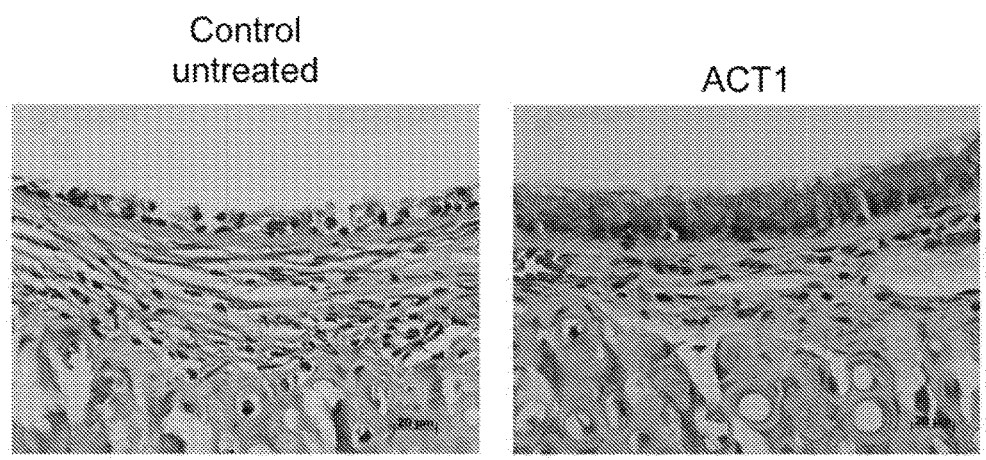
FIG. 7 shows mouse tracheas harvested and stored for 6 h at 4° C. in either PBS or PBS+ACT1 peptide. ACT1 peptide preserved trachea histology.

ACT1 peptide supplementation of UW solution improves cell-cell communication, thus minimizing cell injury, cell dysfunction, inflammation, and improves overall donor organ quality. Specifically: 1) ACT1 peptide prevents UW cold storage induced endothelial and epithelial injury; 2) reduces endothelial pro-inflammatory cytokine release; 3) reduces endothelial permeability post transplantation; 4) reduces heart graft injury post transplantation; and 5) reduces post transplantation inflammation.

iv. Methods:

Heart allograft transplants were performed between Balb/c donors to B6 recipients. Balb/c donor hearts were removed, perfused with UW solution and then static cold stored in either UW solution alone or UW solution supplemented with 100 μM ACT1 peptide for 6 h at 4° C. Following storage, hearts were implanted into B6 recipients using an abdominal heart transplant procedure. Storage in UW solution supplemented with ACT peptide significantly reduced cardiac injury (FIG. 6A), reduced serum cardiac troponin I (FIG. 6B) and significantly reduced neutrophil (FIG. 6C).

Figure 8A:
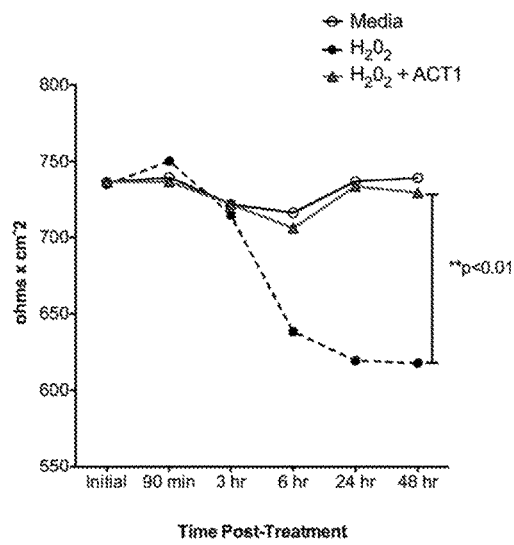
FIGS. 8A-8C shows that ACT1 peptide protects endothelial cells from cold preservation induced damage, hypoxia, inflammation and reperfusion injury. HUVECs were exposed to two experimental conditions to model organ cold storage and reperfusion injuries. Cells were either (8A) exposed to 200 nM $H_2O_2$ to induce oxidative injury, or (8B) exposed to 6 h of cold preservation in UW at 4° C. in hypoxic conditions in the presence or absence of 100 μM ACT1 peptide, followed by 48 h of reperfusion in normal media. Note that ACT1 peptide treatment significantly protects endothelial cells from $H_2O_2$ to induce oxidative stress, and cold preservation, hypoxic reperfusion injury as measured by Trans-endothelial resistance, a marker of cell-cell interactions and cell injury. Further, analysis of IL-8 secretion by endothelial cells exposed to cold preservation, hypoxia and reperfusion shows that ACT1 peptide treated cells are rendered less pro-inflammatory as compared to untreated cells (8C).
Figure 8B:
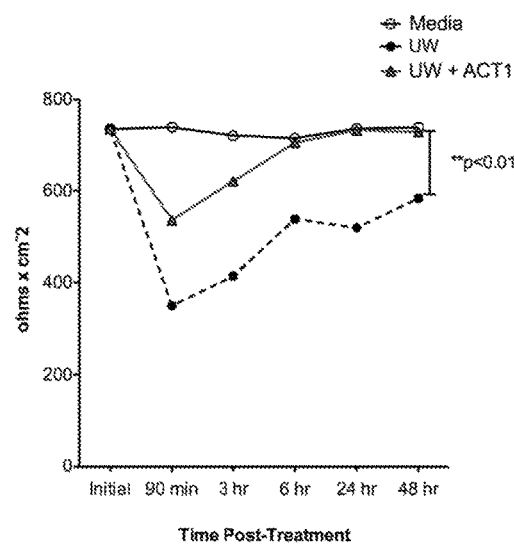
Figure 8C:
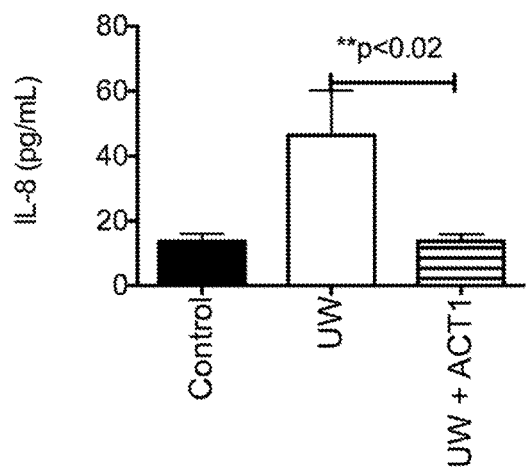

As shown in FIG. 8, ACT1 peptide protects endothelial cells from cold preservation induced damage, hypoxia, inflammation and reperfusion injury. The endothelium is the first point of contact between donor and recipient. Upon reperfusion, the endothelium becomes quickly activated and initiates pro-inflammatory, pro-coagulant, and co-stimulatory roles that lead to graft injury and activation of adaptive immune responses. In addition, the endothelium acts as a barrier between the transplanted organ and recipient, and modulates the trafficking of immune cells into the graft. Strategies to protect the endothelium from cold storage and reperfusion induced injury may reduce graft injury and acute rejection. Endothelial cells are anchored together by gap junctions (GJ) and tight junctions (TJ), the integrity of which is important for endothelial cell and barrier health. Breakdown of GJ and TJ is associated with endothelial death, injury and activation, and this breakdown occurs as consequence of cold storage, and reperfusion injury. Strategies to protect GJ and TJ integrity may protect the endothelium from injury early post transplantation and, further, may reduce IRI. Here, we explore the use of ACT1 peptide, which has been shown to stabilize and strengthen GJ and TJ in wound healing models (Ghatnekar et al., 2009). We show that stabilization of GJ and TJ with ACT1 peptide significantly inhibits post transplantation IRI.

v. Results

In vitro studies described herein (FIG. 8) demonstrate that UW+ACT1 solution significantly reduced endothelial cell injury and inflammation post reperfusion as evidenced by improved TEER and reduced IL-8 secretion. ACT1 peptide treatment significantly protects endothelial cells from $H_2O_2$ to induce oxidative stress, and cold preservation, hypoxic reperfusion injury as measured by TEER, a marker of cell-cell interactions and cell injury. Further analysis of IL-8 secretion by endothelial cells exposed to cold preservation, hypoxia and reperfusion shows that ACT1 peptide treated cells are rendered less pro-inflammatory as compared to untreated cells.

Further, the addition of ACT1 peptide to UW preservation solution significantly reduces ischemic reperfusion induced graft injury and inflammation in a cardiac heterotopic allograft model.

Taken together, these novel findings propose a role for GJ and TJ in the pathogenesis of IRI and further demonstrate that stabilization of GJ and TJ with ACT1 peptide significantly inhibits post transplantation IRI.

vi. Methods:

In Vitro Ischemia Reperfusion Model

HUVECs were exposed to either 18 h of cold storage in UW solution or UW/ACT1 followed by 48 h of reperfusion to model IRI in vitro, as previously described (Atkinson et al., 2013), or $H_2O_2$±ACT1 peptide to model oxidative stress. Efficacy was determined by TEER and IL-8 release.

Heterotopic Heart Transplantation

Figure 9A:
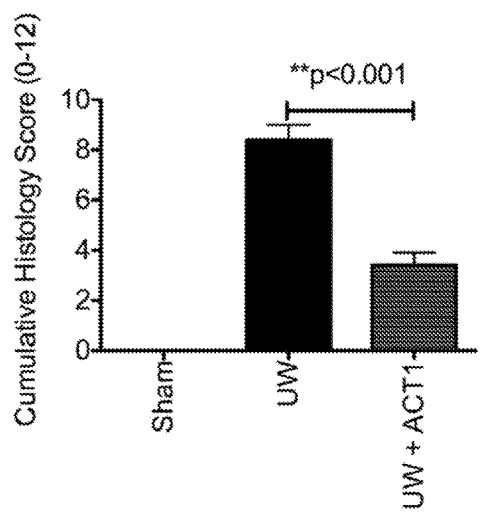
FIGS. 9A-9B show that addition of ACT1 peptide to UW preservation solution significantly reduces post transplantation IRI injury. Grafts and serum were harvested 48 h post transplantation and histologically graded for injury (9A) and the serum concentration of Cardiac troponin I (9B). (n=3-6).
Figure 9B:
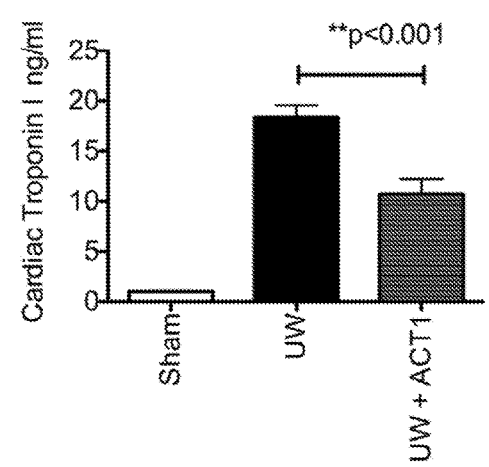
Figure 10A:
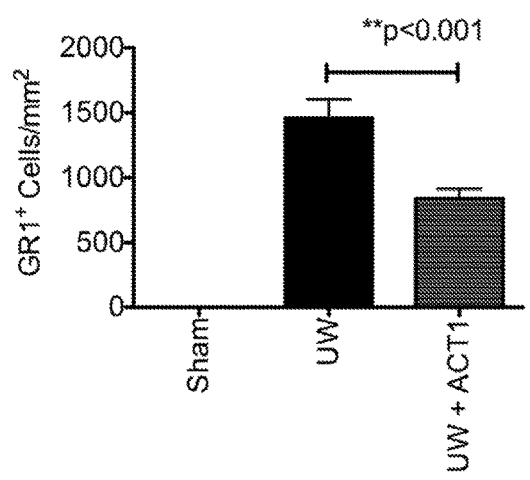
FIGS. 10A-10B show that addition of ACT1 peptide to UW preservation solution significantly reduces post-transplant innate immune cell infiltration. Grafts were harvested 48 h (Gr-1, 10A) and macrophages (Mac-3, 10B) quantified by immunohistochemistry. (n=3-6).
Figure 10B:
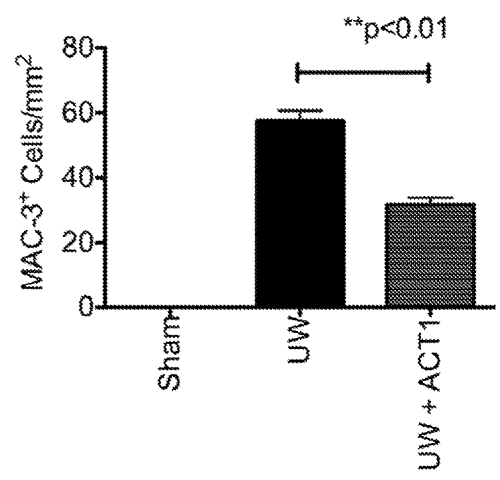
Figure 11A:
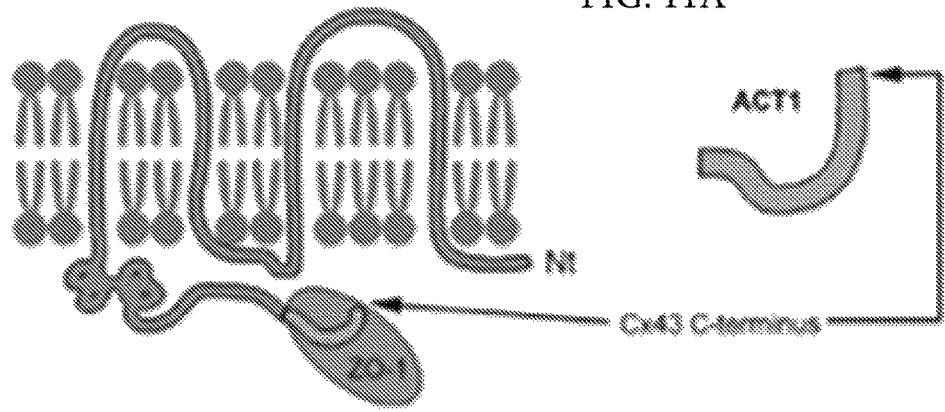
FIGS. 11A-11B show a proposed mechanism of action of ACT1 peptide. (11A) Normally: ZO-1 binds to tight and Gap Junction protein Cx43 at C-terminus of Cx43 and causes junction turnover. (11B) ACT1 peptide temporarily prohibits Cx43 and ZO-1 interaction.
Figure 11B:
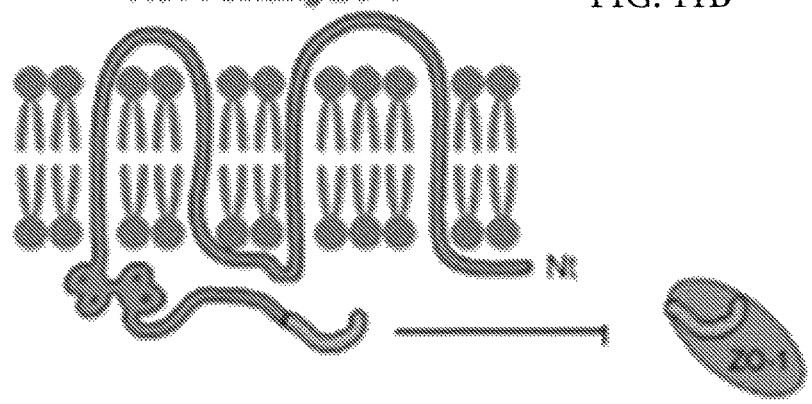

Heterotopic abdominal heart transplants were performed between Balb/c and C57Bl/6 mice, as previously described (Gao et al., 2014). Donor hearts were cold preserved in UW or UW/ACT1 (1000 μM) for 6 h at 4° C. Following storage, hearts were then implanted and harvested at 48 h post transplantation to access the impact of ACT1 peptide post-treatment on IRI. Post transplant injury was assessed by analyses of serum Cardiac Troponin I and histological scoring of cardiac graft injury (FIG. 9) and inflammation; neutrophil and macrophage infiltration (FIG. 10), and pro-inflammatory cytokine.

What is claimed is:

1. A method of treating a stroke in a subject in need thereof, the method comprising administering to the subject a composition comprising an isolated polypeptide consisting of the carboxy terminal-most 4 to 30 contiguous amino acids of an alpha Connexin or a conservative variant thereof.

2. The method of claim 1, wherein the method prevents or treats ischemia and reperfusion injury following the stroke.

3. The method of claim 1, wherein the stroke is a hemorrhagic stroke or a cerebral stroke.

4. The method of claim 1, wherein the polypeptide comprises the carboxy terminal-most 5 to 19 contiguous amino acids of the alpha Connexin.

5. The method of claim 1, wherein the composition is administered topically, orally, intracranially, intravaginally, intraanally, subcutaneously, intradermally, intracardiac, intragastric, intravenously, intramuscularly, by intraperitoneal injection, transdermally, intranasally, or by inhalant.

6. The method of claim 1, wherein the composition is coated on a medical implant.

7. The method of claim 1, wherein the alpha Connexin is selected from a group consisting of Connexin 30.2, Connexin 31.9, Connexin 33, Connexin 35, Connexin 36, Connexin 37, Connexin 38, Connexin 39, Connexin 39.9, Connexin 40, Connexin 40.1, Connexin 43, Connexin 43.4, Connexin 44, Connexin 44.2, Connexin 44.1, Connexin 45, Connexin 46, Connexin 46.6, Connexin 47, Connexin 49, Connexin 50, Connexin 56, or Connexin 59.

8. The method of claim 1, wherein the alpha Connexin is Connexin 37, Connexin 40, Connexin 43, or Connexin 45.

9. The method of claim 1, wherein the polypeptide comprises the amino acid sequence selected from the group consisting of SEQ ID NO: 1, SEQ ID NO: 2, SEQ ID NO: 3, SEQ ID NO: 4, and SEQ ID NO: 5.

10. The method of claim 1, wherein the polypeptide comprises the amino sequence of SEQ ID NO: 2.

11. The method of claim 1, wherein the polypeptide further comprises a cellular internalization sequence.

12. The method of claim 11, wherein the cellular internalization sequence comprises an amino acid sequence of a protein selected from a group consisting of Antennapedia, TAT, HIV-Tat, Penetratin, Antp-3A (Antp mutant), Buforin II, Transportan, MAP (model amphipathic peptide), K-FGF, Ku70, Prion, pVEC, Pep-1, SynB 1, Pep-7, HN-1, BGSC (Bis-Guanidinium-Spermidine-Cholesterol) and BGTC (Bis-Guanidinium-Tren-Cholesterol).

13. The method of claim 12, wherein the cellular internalization sequence is Antennapedia, and wherein the sequence comprises the amino acid sequence of SEQ ID NO:7.

14. The method of claim 11, wherein the polypeptide is linked at its amino terminus to the cellular internalization transporter sequence, and wherein the amino acid sequence of the polypeptide and cellular transporter sequence is selected from the group consisting of SEQ ID NO:8, SEQ ID NO:9, SEQ ID NO: 10, SEQ ID NO: 11, and SEQ ID NO: 12.

* * * * *

SEQUENCE LISTING

```
<160> NUMBER OF SEQ ID NOS: 92

<210> SEQ ID NO 1
<211> LENGTH: 20
<212> TYPE: PRT
<213> ORGANISM: Artificial Sequence
<220> FEATURE:
<223> OTHER INFORMATION: Synthetic Construct

<400> SEQUENCE: 1

Pro Ser Ser Arg Ala Ser Ser Arg Ala Ser Ser Arg Pro Arg Pro Asp
1               5                   10                  15

Asp Leu Glu Ile
            20

<210> SEQ ID NO 2
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 2

Arg Pro Arg Pro Asp Asp Leu Glu Ile
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Arg Pro Arg Pro Asp Asp Leu Glu Val
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Construct

<400> SEQUENCE: 4

Arg Pro Arg Pro Asp Asp Val Pro Val
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5

Lys Ala Arg Ser Asp Asp Leu Ser Val
1               5

<210> SEQ ID NO 6
<211> LENGTH: 27
<212> TYPE: DNA
<213> ORGANISM: Artificial Sequence
<220> FEATURE:
<223> OTHER INFORMATION: Synthetic Construct

<400> SEQUENCE: 6
agacctcggc ctgatgacct ggagatt                                           27

<210> SEQ ID NO 7
<211> LENGTH: 16
<212> TYPE: PRT
<213> ORGANISM: Artificial Sequence
<220> FEATURE:
<223> OTHER INFORMATION: Synthetic Construct

<400> SEQUENCE: 7

Arg Gln Pro Lys Ile Trp Phe Pro Asn Arg Arg Lys Pro Trp Lys Lys
1               5                   10                  15

<210> SEQ ID NO 8
<211> LENGTH: 36
<212> TYPE: PRT
<213> ORGANISM: Artificial Sequence
<220> FEATURE:
<223> OTHER INFORMATION: Synthetic Construct

<400> SEQUENCE: 8
```

Arg Gln Pro Lys Ile Trp Phe Pro Asn Arg Lys Pro Trp Lys Lys
1               5                   10                  15

Pro Ser Ser Arg Ala Ser Ser Arg Ala Ser Ser Arg Pro Arg Pro Asp
            20                  25                  30

Asp Leu Glu Ile
        35

<210> SEQ ID NO 9
<211> LENGTH: 25
<212> TYPE: PRT
<213> ORGANISM: Artificial Sequence
<220> FEATURE:
<223> OTHER INFORMATION: Synthetic Construct

<400> SEQUENCE: 9

Arg Gln Pro Lys Ile Trp Phe Pro Asn Arg Arg Lys Pro Trp Lys Lys
1               5                   10                  15

Arg Pro Arg Pro Asp Asp Leu Glu Ile
            20                  25

<210> SEQ ID NO 10
<211> LENGTH: 25
<212> TYPE: PRT
<213> ORGANISM: Artificial Sequence
<220> FEATURE:
<223> OTHER INFORMATION: Synthetic Construct

<400> SEQUENCE: 10

Arg Gln Pro Lys Ile Trp Phe Pro Asn Arg Arg Lys Pro Trp Lys Lys
1               5                   10                  15

Arg Pro Arg Pro Asp Asp Leu Glu Val
            20                  25

<210> SEQ ID NO 11
<211> LENGTH: 25
<212> TYPE: PRT
<213> ORGANISM: Artificial Sequence
<220> FEATURE:
<223> OTHER INFORMATION: Synthetic Construct

<400> SEQUENCE: 11

Arg Gln Pro Lys Ile Trp Phe Pro Asn Arg Arg Lys Pro Trp Lys Lys
1               5                   10                  15

Arg Pro Arg Pro Asp Asp Val Pro Val
            20                  25

<210> SEQ ID NO 12
<211> LENGTH: 25
<212> TYPE: PRT
<213> ORGANISM: Artificial Sequence
<220> FEATURE:
<223> OTHER INFORMATION: Synthetic Construct

<400> SEQUENCE: 12

Arg Gln Pro Lys Ile Trp Phe Pro Asn Arg Arg Lys Pro Trp Lys Lys
1               5                   10                  15

Lys Ala Arg Ser Asp Asp Leu Ser Val
            20                  25

<210> SEQ ID NO 13
<211> LENGTH: 74
<212> TYPE: DNA
<213> ORGANISM: Artificial Sequence
<220> FEATURE:

<223> OTHER INFORMATION: Synthetic Construct

<400> SEQUENCE: 13
cggcagccca agatctggtt ccccaaccgg cggaagccct ggaagaagcg gcccggcccg    60
acgacctgga gatc                                                     74

<210> SEQ ID NO 14
<211> LENGTH: 11
<212> TYPE: PRT
<213> ORGANISM: Artificial Sequence
<220> FEATURE:
<223> OTHER INFORMATION: Synthetic Construct

<400> SEQUENCE: 14

Gly Arg Lys Lys Arg Arg Gln Arg Pro Pro Gln
1               5                   10

<210> SEQ ID NO 15
<211> LENGTH: 16
<212> TYPE: PRT
<213> ORGANISM: Artificial Sequence
<220> FEATURE:
<223> OTHER INFORMATION: Synthetic Construct

<400> SEQUENCE: 15

Arg Gln Ile Lys Ile Trp Phe Gln Asn Arg Arg Met Lys Trp Lys Lys
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthetic Construct

<400> SEQUENCE: 16

Arg Gln Ile Ala Ile Trp Phe Gln Asn Arg Arg Met Lys Trp Ala Ala
1               5                   10                  15

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct

<400> SEQUENCE: 17

Arg Lys Lys Arg Arg Gln Arg Arg Arg
1               5

<210> SEQ ID NO 18
<211> LENGTH: 21
<212> TYPE: PRT
<213> ORGANISM: Artificial Sequence
<220> FEATURE:
<223> OTHER INFORMATION: Synthetic Construct

<400> SEQUENCE: 18

Thr Arg Ser Ser Arg Ala Gly Leu Gln Phe Pro Val Gly Arg Val His
1               5                   10                  15

Arg Leu Leu Arg Lys
            20

<210> SEQ ID NO 19
<211> LENGTH: 26

```
<212> TYPE: PRT
<213> ORGANISM: Artificial Sequence
<220> FEATURE:
<223> OTHER INFORMATION: Synthetic Construct

<400> SEQUENCE: 19

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 20
<211> LENGTH: 18
<212> TYPE: PRT
<213> ORGANISM: Artificial Sequence
<220> FEATURE:
<223> OTHER INFORMATION: Synthetic Construct

<400> SEQUENCE: 20

Lys Leu Ala Leu Lys Leu Ala Leu Lys Ala Leu Lys Ala Ala Leu Lys
1               5                   10                  15

Leu Ala

<210> SEQ ID NO 21
<211> LENGTH: 16
<212> TYPE: PRT
<213> ORGANISM: Artificial Sequence
<220> FEATURE:
<223> OTHER INFORMATION: Synthetic Construct

<400> SEQUENCE: 21

Ala Ala Val Ala Leu Leu Pro Ala Val Leu Leu Ala Leu Leu Ala Pro
1               5                   10                  15

<210> SEQ ID NO 22
<211> LENGTH: 10
<212> TYPE: PRT
<213> ORGANISM: Artificial Sequence
<220> FEATURE:
<223> OTHER INFORMATION: Synthetic Construct

<400> SEQUENCE: 22

Val Pro Met Leu Lys Pro Met Leu Lys Glu
1               5                   10

<210> SEQ ID NO 23
<211> LENGTH: 28
<212> TYPE: PRT
<213> ORGANISM: Artificial Sequence
<220> FEATURE:
<223> OTHER INFORMATION: Synthetic Construct

<400> SEQUENCE: 23

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 24
<211> LENGTH: 18
<212> TYPE: PRT
<213> ORGANISM: Artificial Sequence
<220> FEATURE:
<223> OTHER INFORMATION: Synthetic Construct

<400> SEQUENCE: 24
```

```
Leu Leu Ile Ile Leu Arg Arg Arg Ile Arg Lys Gln Ala His Ala His
1               5                   10                  15

Ser Lys

<210> SEQ ID NO 25
<211> LENGTH: 21
<212> TYPE: PRT
<213> ORGANISM: Artificial Sequence
<220> FEATURE:
<223> OTHER INFORMATION: Synthetic Construct

<400> SEQUENCE: 25

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 26
<211> LENGTH: 18
<212> TYPE: PRT
<213> ORGANISM: Artificial Sequence
<220> FEATURE:
<223> OTHER INFORMATION: Synthetic Construct

<400> SEQUENCE: 26

Arg Gly Gly Arg Leu Ser Tyr Ser Arg Arg Arg Phe Ser Thr Ser Thr
1               5                   10                  15

Gly Arg

<210> SEQ ID NO 27
<211> LENGTH: 15
<212> TYPE: PRT
<213> ORGANISM: Artificial Sequence
<220> FEATURE:
<223> OTHER INFORMATION: Synthetic Construct

<400> SEQUENCE: 27

Ser Asp Leu Trp Glu Met Met Met Val Ser Leu Ala Cys Gln Tyr
1               5                   10                  15

<210> SEQ ID NO 28
<211> LENGTH: 12
<212> TYPE: PRT
<213> ORGANISM: Artificial Sequence
<220> FEATURE:
<223> OTHER INFORMATION: Synthetic Construct

<400> SEQUENCE: 28

Thr Ser Pro Leu Asn Ile His Asn Gly Gln Lys Leu
1               5                   10

<210> SEQ ID NO 29
<211> LENGTH: 19
<212> TYPE: PRT
<213> ORGANISM: Artificial Sequence
<220> FEATURE:
<223> OTHER INFORMATION: Synthetic Construct

<400> SEQUENCE: 29

Pro Ser Arg Ala Ser Ser Arg Ala Ser Ser Arg Pro Arg Pro Asp Asp
1               5                   10                  15

Leu Glu Ile
```

```
<210> SEQ ID NO 30
<211> LENGTH: 20
<212> TYPE: PRT
<213> ORGANISM: Artificial Sequence
<220> FEATURE:
<223> OTHER INFORMATION: Synthetic Construct

<400> SEQUENCE: 30

Gly Ser Asn Lys Ser Thr Ala Ser Ser Lys Ser Pro Asp Pro Lys Asn
1               5                   10                  15

Ser Val Trp Ile
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic Construct

<400> SEQUENCE: 31

Gly Ser Asn Lys Ser Ser Ala Ser Ser Lys Ser Gly Asp Gly Lys Asn
1               5                   10                  15

Ser Val Trp Ile
            20

<210> SEQ ID NO 32
<211> LENGTH: 21
<212> TYPE: PRT
<213> ORGANISM: Artificial Sequence
<220> FEATURE:
<223> OTHER INFORMATION: Synthetic Construct

<400> SEQUENCE: 32

Gly Arg Ala Ser Lys Ala Ser Arg Ala Ser Ser Gly Arg Ala Arg Pro
1               5                   10                  15

Glu Asp Leu Ala Ile
            20

<210> SEQ ID NO 33
<211> LENGTH: 13
<212> TYPE: PRT
<213> ORGANISM: Artificial Sequence
<220> FEATURE:
<223> OTHER INFORMATION: Synthetic Construct

<400> SEQUENCE: 33

Gly Ser Ala Ser Ser Arg Asp Gly Lys Thr Val Trp Ile
1               5                   10

<210> SEQ ID NO 34
<211> LENGTH: 19
<212> TYPE: PRT
<213> ORGANISM: Artificial Sequence
<220> FEATURE:
<223> OTHER INFORMATION: Synthetic Construct

<400> SEQUENCE: 34

Pro Arg Val Ser Val Pro Asn Phe Gly Arg Thr Gln Ser Ser Asp Ser
1               5                   10                  15

Ala Tyr Val

<210> SEQ ID NO 35
<211> LENGTH: 19
<212> TYPE: PRT
```

```
<213> ORGANISM: Artificial Sequence
<220> FEATURE:
<223> OTHER INFORMATION: Synthetic Construct

<400> SEQUENCE: 35

Pro Arg Met Ser Met Pro Asn Phe Gly Arg Thr Gln Ser Ser Asp Ser
1               5                   10                  15

Ala Tyr Val

<210> SEQ ID NO 36
<211> LENGTH: 21
<212> TYPE: PRT
<213> ORGANISM: Artificial Sequence
<220> FEATURE:
<223> OTHER INFORMATION: Synthetic Construct

<400> SEQUENCE: 36

Pro Arg Ala Gly Ser Glu Lys Gly Ser Ala Ser Ser Arg Asp Gly Lys
1               5                   10                  15

Thr Thr Val Trp Ile
            20

<210> SEQ ID NO 37
<211> LENGTH: 23
<212> TYPE: PRT
<213> ORGANISM: Artificial Sequence
<220> FEATURE:
<223> OTHER INFORMATION: Synthetic Construct

<400> SEQUENCE: 37

Gly Tyr His Ser Asp Lys Arg Arg Leu Ser Lys Ala Ser Ser Lys Ala
1               5                   10                  15

Arg Ser Asp Asp Leu Ser Val
            20

<210> SEQ ID NO 38
<211> LENGTH: 19
<212> TYPE: PRT
<213> ORGANISM: Artificial Sequence
<220> FEATURE:
<223> OTHER INFORMATION: Synthetic Construct

<400> SEQUENCE: 38

Pro Leu Ser Arg Leu Ser Lys Ala Ser Ser Arg Ala Arg Ser Asp Asp
1               5                   10                  15

Leu Thr Val

<210> SEQ ID NO 39
<211> LENGTH: 22
<212> TYPE: PRT
<213> ORGANISM: Artificial Sequence
<220> FEATURE:
<223> OTHER INFORMATION: Synthetic Construct

<400> SEQUENCE: 39

Pro Asn His Val Val Ser Leu Thr Asn Asn Leu Ile Gly Arg Arg Val
1               5                   10                  15

Pro Thr Asp Leu Gln Ile
            20

<210> SEQ ID NO 40
<211> LENGTH: 29
<212> TYPE: PRT
<213> ORGANISM: Artificial Sequence
```

<220> FEATURE:
<223> OTHER INFORMATION: Synthetic Construct

<400> SEQUENCE: 40

Pro Ser Cys Val Ser Ser Ala Val Leu Thr Thr Ile Cys Ser Ser
1               5                   10                  15

Asp Gln Val Val Pro Val Gly Leu Ser Ser Phe Tyr Met
            20                  25

<210> SEQ ID NO 41
<211> LENGTH: 21
<212> TYPE: PRT
<213> ORGANISM: Artificial Sequence
<220> FEATURE:
<223> OTHER INFORMATION: Synthetic Construct

<400> SEQUENCE: 41

Gly Arg Ser Ser Lys Ala Ser Lys Ser Gly Gly Arg Ala Arg Ala
1               5                   10                  15

Ala Asp Leu Ala Ile
            20

<210> SEQ ID NO 42
<211> LENGTH: 17
<212> TYPE: PRT
<213> ORGANISM: Artificial Sequence
<220> FEATURE:
<223> OTHER INFORMATION: Synthetic Construct

<400> SEQUENCE: 42

Leu Cys Tyr Leu Leu Ile Arg Tyr Cys Ser Gly Lys Ser Lys Lys Pro
1               5                   10                  15

Val

<210> SEQ ID NO 43
<211> LENGTH: 18
<212> TYPE: PRT
<213> ORGANISM: Artificial Sequence
<220> FEATURE:
<223> OTHER INFORMATION: Synthetic Construct

<400> SEQUENCE: 43

Gly Gln Lys Pro Pro Ser Arg Pro Ser Ser Ala Ser Lys Lys Gln
1               5                   10                  15

Tyr Val

<210> SEQ ID NO 44
<211> LENGTH: 19
<212> TYPE: PRT
<213> ORGANISM: Artificial Sequence
<220> FEATURE:
<223> OTHER INFORMATION: Synthetic Construct

<400> SEQUENCE: 44

Ser Ser Arg Ala Ser Ser Arg Ala Ser Ser Arg Pro Arg Pro Asp Asp
1               5                   10                  15

Leu Glu Val

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 45

Arg Pro Lys Pro Asp Asp Leu Glu Ile
1               5

<210> SEQ ID NO 46
<211> LENGTH: 19
<212> TYPE: PRT
<213> ORGANISM: Artificial Sequence
<220> FEATURE:
<223> OTHER INFORMATION: Synthetic Construct

<400> SEQUENCE: 46

Ser Ser Arg Ala Ser Ser Arg Ala Ser Ser Arg Pro Lys Pro Asp Asp
1               5                   10                  15

Leu Glu Ile

<210> SEQ ID NO 47
<211> LENGTH: 9
<212> TYPE: PRT
<213> ORGANISM: Artificial Sequence
<220> FEATURE:
<223> OTHER INFORMATION: Synthetic Construct

<400> SEQUENCE: 47

Arg Pro Lys Pro Asp Asp Leu Asp Ile
1               5

<210> SEQ ID NO 48
<211> LENGTH: 19
<212> TYPE: PRT
<213> ORGANISM: Artificial Sequence
<220> FEATURE:
<223> OTHER INFORMATION: Synthetic Construct

<400> SEQUENCE: 48

Ser Ser Arg Ala Ser Ser Arg Ala Ser Ser Arg Pro Arg Pro Asp Asp
1               5                   10                  15

Leu Asp Ile

<210> SEQ ID NO 49
<211> LENGTH: 19
<212> TYPE: PRT
<213> ORGANISM: Artificial Sequence
<220> FEATURE:
<223> OTHER INFORMATION: Synthetic Construct

<400> SEQUENCE: 49

Ser Ser Arg Ala Ser Thr Arg Ala Ser Ser Arg Pro Arg Pro Asp Asp
1               5                   10                  15

Leu Glu Ile

<210> SEQ ID NO 50
<211> LENGTH: 9
<212> TYPE: PRT
<213> ORGANISM: Artificial Sequence
<220> FEATURE:
<223> OTHER INFORMATION: Synthetic Construct

<400> SEQUENCE: 50

Arg Pro Arg Pro Glu Asp Leu Glu Ile
1               5

<210> SEQ ID NO 51
```

```
<211> LENGTH: 19
<212> TYPE: PRT
<213> ORGANISM: Artificial Sequence
<220> FEATURE:
<223> OTHER INFORMATION: Synthetic Construct

<400> SEQUENCE: 51

Ser Ser Arg Ala Ser Ser Arg Ala Ser Ser Arg Pro Arg Pro Glu Asp
1               5                   10                  15
Leu Glu Ile

<210> SEQ ID NO 52
<211> LENGTH: 9
<212> TYPE: PRT
<213> ORGANISM: Artificial Sequence
<220> FEATURE:
<223> OTHER INFORMATION: Synthetic Construct

<400> SEQUENCE: 52

Gly Asp Gly Lys Asn Ser Val Trp Val
1               5

<210> SEQ ID NO 53
<211> LENGTH: 23
<212> TYPE: PRT
<213> ORGANISM: Artificial Sequence
<220> FEATURE:
<223> OTHER INFORMATION: Synthetic Construct

<400> SEQUENCE: 53

Ser Lys Ala Gly Ser Asn Lys Ser Thr Ala Ser Ser Lys Ser Gly Asp
1               5                   10                  15
Gly Lys Asn Ser Val Trp Val
            20

<210> SEQ ID NO 54
<211> LENGTH: 18
<212> TYPE: PRT
<213> ORGANISM: Artificial Sequence
<220> FEATURE:
<223> OTHER INFORMATION: Synthetic Construct

<400> SEQUENCE: 54

Gly Gln Lys Pro Pro Ser Arg Pro Ser Ser Ser Ala Ser Lys Lys Leu
1               5                   10                  15
Tyr Val

<210> SEQ ID NO 55
<211> LENGTH: 24
<212> TYPE: PRT
<213> ORGANISM: Artificial Sequence
<220> FEATURE:
<223> OTHER INFORMATION: Synthetic Construct

<400> SEQUENCE: 55

Arg Gln Pro Lys Ile Trp Phe Pro Asn Arg Arg Lys Pro Trp Lys Ile
1               5                   10                  15
Glu Leu Asp Asp Pro Arg Pro Arg
            20

<210> SEQ ID NO 56
<211> LENGTH: 20
<212> TYPE: PRT
<213> ORGANISM: Artificial Sequence
<220> FEATURE:
```

```
<223> OTHER INFORMATION: Synthetic Construct

<400> SEQUENCE: 56

Gly Arg Lys Lys Arg Arg Gln Arg Pro Pro Gln Arg Pro Arg Pro Asp
1               5                   10                  15

Asp Leu Glu Ile
            20

<210> SEQ ID NO 57
<211> LENGTH: 25
<212> TYPE: PRT
<213> ORGANISM: Artificial Sequence
<220> FEATURE:
<223> OTHER INFORMATION: Synthetic Construct

<400> SEQUENCE: 57

Arg Gln Ile Lys Ile Trp Phe Gln Asn Arg Arg Met Lys Trp Lys Lys
1               5                   10                  15

Arg Pro Arg Pro Asp Asp Leu Glu Ile
            20                  25

<210> SEQ ID NO 58
<211> LENGTH: 25
<212> TYPE: PRT
<213> ORGANISM: Artificial Sequence
<220> FEATURE:
<223> OTHER INFORMATION: Synthetic Construct

<400> SEQUENCE: 58

Arg Gln Ile Ala Ile Trp Phe Gln Asn Arg Arg Met Lys Trp Ala Ala
1               5                   10                  15

Arg Pro Arg Pro Asp Asp Leu Glu Ile
            20                  25

<210> SEQ ID NO 59
<211> LENGTH: 18
<212> TYPE: PRT
<213> ORGANISM: Artificial Sequence
<220> FEATURE:
<223> OTHER INFORMATION: Synthetic Construct

<400> SEQUENCE: 59

Arg Lys Lys Arg Arg Gln Arg Arg Arg Pro Arg Pro Asp Asp Leu
1               5                   10                  15

Glu Ile

<210> SEQ ID NO 60
<211> LENGTH: 30
<212> TYPE: PRT
<213> ORGANISM: Artificial Sequence
<220> FEATURE:
<223> OTHER INFORMATION: Synthetic Construct

<400> SEQUENCE: 60

Thr Arg Ser Ser Arg Ala Gly Leu Gln Phe Pro Val Gly Arg Val His
1               5                   10                  15

Arg Leu Leu Arg Lys Arg Pro Arg Pro Asp Asp Leu Glu Ile
            20                  25                  30

<210> SEQ ID NO 61
<211> LENGTH: 35
<212> TYPE: PRT
<213> ORGANISM: Artificial Sequence
<220> FEATURE:
```

<223> OTHER INFORMATION: Synthetic Construct

<400> SEQUENCE: 61

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu Arg Pro Arg Pro Asp Asp
            20                  25                  30

Leu Glu Ile
        35

<210> SEQ ID NO 62
<211> LENGTH: 27
<212> TYPE: PRT
<213> ORGANISM: Artificial Sequence
<220> FEATURE:
<223> OTHER INFORMATION: Synthetic Construct

<400> SEQUENCE: 62

Lys Leu Ala Leu Lys Leu Ala Leu Lys Ala Leu Lys Ala Ala Leu Lys
1               5                   10                  15

Leu Ala Arg Pro Arg Pro Asp Asp Leu Glu Ile
            20                  25

<210> SEQ ID NO 63
<211> LENGTH: 25
<212> TYPE: PRT
<213> ORGANISM: Artificial Sequence
<220> FEATURE:
<223> OTHER INFORMATION: Synthetic Construct

<400> SEQUENCE: 63

Ala Ala Val Ala Leu Leu Pro Ala Val Leu Leu Ala Leu Leu Ala Pro
1               5                   10                  15

Arg Pro Arg Pro Asp Asp Leu Glu Ile
            20                  25

<210> SEQ ID NO 64
<211> LENGTH: 19
<212> TYPE: PRT
<213> ORGANISM: Artificial Sequence
<220> FEATURE:
<223> OTHER INFORMATION: Synthetic Construct

<400> SEQUENCE: 64

Val Pro Met Leu Lys Pro Met Leu Lys Glu Arg Pro Arg Pro Asp Asp
1               5                   10                  15

Leu Glu Ile

<210> SEQ ID NO 65
<211> LENGTH: 37
<212> TYPE: PRT
<213> ORGANISM: Artificial Sequence
<220> FEATURE:
<223> OTHER INFORMATION: Synthetic Construct

<400> SEQUENCE: 65

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Arg Pro Arg Pro
            20                  25                  30

Asp Asp Leu Glu Ile
        35

<210> SEQ ID NO 66
<211> LENGTH: 27
<212> TYPE: PRT
<213> ORGANISM: Artificial Sequence
<220> FEATURE:
<223> OTHER INFORMATION: Synthetic Construct

<400> SEQUENCE: 66

Leu Leu Ile Ile Leu Arg Arg Arg Ile Arg Lys Gln Ala His Ala His
1               5                   10                  15

Ser Lys Arg Pro Arg Pro Asp Asp Leu Glu Ile
            20                  25

<210> SEQ ID NO 67
<211> LENGTH: 30
<212> TYPE: PRT
<213> ORGANISM: Artificial Sequence
<220> FEATURE:
<223> OTHER INFORMATION: Synthetic Construct

<400> SEQUENCE: 67

Lys Glu Thr Trp Trp Glu Thr Trp Trp Thr Glu Trp Ser Gln Pro Lys
1               5                   10                  15

Lys Lys Arg Lys Val Arg Pro Arg Pro Asp Asp Leu Glu Ile
            20                  25                  30

<210> SEQ ID NO 68
<211> LENGTH: 27
<212> TYPE: PRT
<213> ORGANISM: Artificial Sequence
<220> FEATURE:
<223> OTHER INFORMATION: Synthetic Construct

<400> SEQUENCE: 68

Arg Gly Gly Arg Leu Ser Tyr Ser Arg Arg Arg Phe Ser Thr Ser Thr
1               5                   10                  15

Gly Arg Arg Pro Arg Pro Asp Asp Leu Glu Ile
            20                  25

<210> SEQ ID NO 69
<211> LENGTH: 24
<212> TYPE: PRT
<213> ORGANISM: Artificial Sequence
<220> FEATURE:
<223> OTHER INFORMATION: Synthetic Construct

<400> SEQUENCE: 69

Ser Asp Leu Trp Glu Met Met Met Val Ser Leu Ala Cys Gln Tyr Arg
1               5                   10                  15

Pro Arg Pro Asp Asp Leu Glu Ile
            20

<210> SEQ ID NO 70
<211> LENGTH: 21
<212> TYPE: PRT
<213> ORGANISM: Artificial Sequence
<220> FEATURE:
<223> OTHER INFORMATION: Synthetic Construct

<400> SEQUENCE: 70

Thr Ser Pro Leu Asn Ile His Asn Gly Gln Lys Leu Arg Pro Arg Pro
1               5                   10                  15

Asp Asp Leu Glu Ile
            20

<210> SEQ ID NO 71
<211> LENGTH: 122
<212> TYPE: PRT
<213> ORGANISM: Artificial Sequence
<220> FEATURE:
<223> OTHER INFORMATION: Synthetic Construct

<400> SEQUENCE: 71

```
Lys Gly Lys Ser Asp Pro Tyr His Ala Thr Ser Gly Ala Leu Ser Pro
1               5                   10                  15

Ala Lys Asp Cys Gly Ser Gln Lys Tyr Ala Tyr Phe Asn Gly Cys Ser
            20                  25                  30

Ser Pro Thr Ala Pro Leu Ser Pro Met Ser Pro Pro Gly Tyr Lys Leu
        35                  40                  45

Val Thr Gly Asp Arg Asn Asn Ser Ser Cys Arg Asn Tyr Asn Lys Gln
    50                  55                  60

Ala Ser Glu Gln Asn Trp Ala Asn Tyr Ser Ala Glu Gln Asn Arg Met
65                  70                  75                  80

Gly Gln Ala Gly Ser Thr Ile Ser Asn Ser His Ala Gln Pro Phe Asp
                85                  90                  95

Phe Pro Asp Asp Asn Gln Asn Ser Lys Lys Leu Ala Ala Gly His Glu
            100                 105                 110

Leu Gln Pro Leu Ala Ile Val Asp Gln Arg
        115                 120
```

<210> SEQ ID NO 72
<211> LENGTH: 120
<212> TYPE: PRT
<213> ORGANISM: Artificial Sequence
<220> FEATURE:
<223> OTHER INFORMATION: Synthetic Construct

<400> SEQUENCE: 72

```
Lys Thr Asp Pro Tyr Ser His Ser Gly Thr Met Ser Pro Ser Lys Asp
1               5                   10                  15

Cys Gly Ser Pro Lys Tyr Ala Tyr Tyr Asn Gly Cys Ser Ser Pro Thr
            20                  25                  30

Ala Pro Leu Ser Pro Met Ser Pro Pro Gly Tyr Lys Leu Val Thr Gly
        35                  40                  45

Asp Arg Asn Asn Ser Ser Cys Arg Asn Tyr Asn Lys Gln Ala Ser Glu
    50                  55                  60

Gln Asn Trp Ala Asn Tyr Ser Ala Glu Gln Asn Arg Met Gly Gln Ala
65                  70                  75                  80

Gly Ser Thr Ile Ser Asn Ser His Ala Gln Pro Phe Asp Phe Ala Asp
                85                  90                  95

Glu His Gln Asn Thr Lys Lys Leu Ala Ser Gly His Glu Leu Gln Pro
            100                 105                 110

Leu Thr Ile Val Asp Gln Arg Pro
        115                 120
```

<210> SEQ ID NO 73
<211> LENGTH: 120
<212> TYPE: PRT
<213> ORGANISM: Artificial Sequence
<220> FEATURE:
<223> OTHER INFORMATION: Synthetic Construct

<400> SEQUENCE: 73

Leu Gly Phe Gly Thr Ile Arg Asp Ser Leu Asn Ser Lys Arg Arg Glu
1               5                   10                  15

Leu Glu Asp Pro Gly Ala Tyr Asn Tyr Pro Phe Thr Trp Asn Thr Pro
            20                  25                  30

Ser Ala Pro Pro Gly Tyr Asn Ile Ala Val Lys Pro Asp Gln Ile Gln
        35                  40                  45

Tyr Thr Glu Leu Ser Asn Ala Lys Ile Ala Tyr Lys Gln Asn Lys Ala
    50                  55                  60

Asn Thr Ala Gln Glu Gln Gln Tyr Gly Ser His Glu Glu Asn Leu Pro
65                  70                  75                  80

Ala Asp Leu Glu Ala Leu Gln Arg Glu Ile Arg Met Ala Gln Glu Arg
                85                  90                  95

Leu Asp Leu Ala Val Gln Ala Tyr Ser His Gln Asn Asn Pro His Gly
            100                 105                 110

Pro Arg Glu Lys Lys Ala Lys Val
            115                 120

<210> SEQ ID NO 74
<211> LENGTH: 120
<212> TYPE: PRT
<213> ORGANISM: Artificial Sequence
<220> FEATURE:
<223> OTHER INFORMATION: Synthetic Construct

<400> SEQUENCE: 74

Gly Phe Gly Thr Ile Arg Asp Thr Leu Asn Asn Lys Arg Lys Glu Leu
1               5                   10                  15

Glu Asp Ser Gly Thr Tyr Asn Tyr Pro Phe Thr Trp Asn Thr Pro Ser
            20                  25                  30

Ala Pro Pro Gly Tyr Asn Ile Ala Val Lys Pro Asp Gln Met Gln Tyr
        35                  40                  45

Thr Glu Leu Ser Asn Ala Lys Met Ala Tyr Lys Gln Asn Lys Ala Asn
    50                  55                  60

Ile Ala Gln Glu Gln Gln Tyr Gly Ser Asn Glu Glu Asn Ile Pro Ala
65                  70                  75                  80

Asp Leu Glu Asn Leu Gln Arg Glu Ile Lys Val Ala Gln Glu Arg Leu
                85                  90                  95

Asp Met Ala Ile Gln Ala Tyr Asn Asn Gln Asn Asn Pro Gly Ser Ser
            100                 105                 110

Ser Arg Glu Lys Lys Ser Lys Ala
            115                 120

<210> SEQ ID NO 75
<211> LENGTH: 120
<212> TYPE: PRT
<213> ORGANISM: Artificial Sequence
<220> FEATURE:
<223> OTHER INFORMATION: Synthetic Construct

<400> SEQUENCE: 75

Pro Tyr Leu Val Asp Cys Phe Val Ser Arg Pro Thr Glu Lys Thr Ile
1               5                   10                  15

Phe Ile Ile Phe Met Leu Val Val Gly Leu Ile Ser Leu Val Leu Asn
            20                  25                  30

Leu Leu Glu Leu Val His Leu Leu Cys Arg Cys Leu Ser Arg Gly Met
            35                  40                  45

Arg Ala Arg Gln Gly Gln Asp Ala Pro Pro Thr Gln Gly Thr Ser Ser
    50                  55                  60

```
Asp Pro Tyr Thr Asp Gln Val Phe Phe Tyr Leu Pro Val Gly Gln Gly
 65                  70                  75                  80

Pro Ser Ser Pro Pro Cys Pro Thr Tyr Asn Gly Leu Ser Ser Ser Glu
                 85                  90                  95

Gln Asn Trp Ala Asn Leu Thr Thr Glu Glu Arg Leu Ala Ser Ser Arg
            100                 105                 110

Pro Pro Leu Phe Leu Asp Pro Pro
        115                 120

<210> SEQ ID NO 76
<211> LENGTH: 120
<212> TYPE: PRT
<213> ORGANISM: Artificial Sequence
<220> FEATURE:
<223> OTHER INFORMATION: Synthetic Construct

<400> SEQUENCE: 76

Cys Gly Ser Lys Glu His Gly Asn Arg Lys Met Arg Gly Arg Leu Leu
  1               5                  10                  15

Leu Thr Tyr Met Ala Ser Ile Phe Phe Lys Ser Val Phe Glu Val Ala
             20                  25                  30

Phe Leu Leu Ile Gln Trp Tyr Leu Tyr Gly Phe Thr Leu Ser Ala Val
         35                  40                  45

Tyr Ile Cys Glu Gln Ser Pro Cys Pro His Arg Val Asp Cys Phe Leu
     50                  55                  60

Ser Arg Pro Thr Glu Lys Thr Ile Phe Ile Leu Phe Met Leu Val Val
 65                  70                  75                  80

Ser Met Val Ser Phe Val Leu Asn Val Ile Glu Leu Phe Tyr Val Leu
                 85                  90                  95

Phe Lys Ala Ile Lys Asn His Leu Gly Asn Glu Lys Glu Glu Val Tyr
            100                 105                 110

Cys Asn Pro Val Glu Leu Gln Lys
        115                 120

<210> SEQ ID NO 77
<211> LENGTH: 239
<212> TYPE: PRT
<213> ORGANISM: Artificial Sequence
<220> FEATURE:
<223> OTHER INFORMATION: Synthetic Construct

<400> SEQUENCE: 77

Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
```

```
              115                 120                 125
Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 78
<211> LENGTH: 60
<212> TYPE: DNA
<213> ORGANISM: Artificial Sequence
<220> FEATURE:
<223> OTHER INFORMATION: Synthetic Construct

<400> SEQUENCE: 78
ccctcctccc gggcctcctc ccgggcctcc tcccggcccc ggcccgacga cctggagatc    60

<210> SEQ ID NO 79
<211> LENGTH: 27
<212> TYPE: DNA
<213> ORGANISM: Artificial Sequence
<220> FEATURE:
<223> OTHER INFORMATION: Synthetic Construct

<400> SEQUENCE: 79
cggccccggc ccgacgacct ggagatc    27

<210> SEQ ID NO 80
<211> LENGTH: 27
<212> TYPE: DNA
<213> ORGANISM: Artificial Sequence
<220> FEATURE:
<223> OTHER INFORMATION: Synthetic Construct

<400> SEQUENCE: 80
cggccccggc ccgacgacct ggaggtg    27

<210> SEQ ID NO 81
<211> LENGTH: 27
<212> TYPE: DNA
<213> ORGANISM: Artificial Sequence
<220> FEATURE:
<223> OTHER INFORMATION: Synthetic Construct

<400> SEQUENCE: 81
cggccccggc ccgacgacgt gcccgtg    27

<210> SEQ ID NO 82
<211> LENGTH: 27
<212> TYPE: DNA
<213> ORGANISM: Artificial Sequence
<220> FEATURE:
<223> OTHER INFORMATION: Synthetic Construct

<400> SEQUENCE: 82
aaggcccggt ccgacgacct gtccgtg                                              27

<210> SEQ ID NO 83
<211> LENGTH: 48
<212> TYPE: DNA
<213> ORGANISM: Artificial Sequence
<220> FEATURE:
<223> OTHER INFORMATION: Synthetic Construct

<400> SEQUENCE: 83
cggcagccca agatctggtt ccccaaccgg cggaagccct ggaagaag                       48

<210> SEQ ID NO 84
<211> LENGTH: 108
<212> TYPE: DNA
<213> ORGANISM: Artificial Sequence
<220> FEATURE:
<223> OTHER INFORMATION: Synthetic Construct

<400> SEQUENCE: 84
cggcagccca agatctggtt ccccaaccgg cggaagccct ggaagaagcc ctcctcccgg          60
gcctcctccc gggcctcctc ccggccccgg cccgacgacc tggagatc                      108

<210> SEQ ID NO 85
<211> LENGTH: 75
<212> TYPE: DNA
<213> ORGANISM: Artificial Sequence
<220> FEATURE:
<223> OTHER INFORMATION: Synthetic Construct

<400> SEQUENCE: 85
cggcagccca agatctggtt ccccaaccgg cggaagccct ggaagaagcg ccccggccc           60 gacgacctgg agatc                                                          75

<210> SEQ ID NO 86
<211> LENGTH: 75
<212> TYPE: DNA
<213> ORGANISM: Artificial Sequence
<220> FEATURE:
<223> OTHER INFORMATION: Synthetic Construct

<400> SEQUENCE: 86
cggcagccca agatctggtt ccccaaccgg cggaagccct ggaagaagcg ccccggccc           60 gacgacctgg aggtg                                                          75

<210> SEQ ID NO 87
<211> LENGTH: 75
<212> TYPE: DNA
<213> ORGANISM: Artificial Sequence
<220> FEATURE:
<223> OTHER INFORMATION: Synthetic Construct

<400> SEQUENCE: 87
cggcagccca agatctggtt ccccaaccgg cggaagccct ggaagaagcg ccccggccc           60 gacgacgtgc ccgtg                                                          75

<210> SEQ ID NO 88
<211> LENGTH: 75
<212> TYPE: DNA
<213> ORGANISM: Artificial Sequence
<220> FEATURE:
<223> OTHER INFORMATION: Synthetic Construct

```
<400> SEQUENCE: 88
cggcagccca agatctggtt ccccaaccgg cggaagccct ggaagaagaa ggcccggtcc      60
gacgacctgt ccgtg                                                      75

<210> SEQ ID NO 89
<211> LENGTH: 20
<212> TYPE: PRT
<213> ORGANISM: Artificial Sequence
<220> FEATURE:
<223> OTHER INFORMATION: Synthetic Construct

<400> SEQUENCE: 89

Pro Cys Ser Arg Ala Ser Ser Arg Met Ser Ser Arg Ala Arg Pro Asp
1               5                   10                  15

Asp Leu Asp Val
            20

<210> SEQ ID NO 90
<211> LENGTH: 19
<212> TYPE: PRT
<213> ORGANISM: Artificial Sequence
<220> FEATURE:
<223> OTHER INFORMATION: Synthetic Construct

<400> SEQUENCE: 90

Pro Arg Val Ser Val Pro Asn Phe Gly Arg Thr Gln Ser Ser Asp Ser
1               5                   10                  15

Ala Tyr Val

<210> SEQ ID NO 91
<211> LENGTH: 19
<212> TYPE: PRT
<213> ORGANISM: Artificial Sequence
<220> FEATURE:
<223> OTHER INFORMATION: Synthetic Construct

<400> SEQUENCE: 91

Pro Arg Met Ser Met Pro Asn Phe Gly Arg Thr Gln Ser Ser Asp Ser
1               5                   10                  15

Ala Tyr Val

<210> SEQ ID NO 92
<211> LENGTH: 32
<212> TYPE: PRT
<213> ORGANISM: Artificial Sequence
<220> FEATURE:
<223> OTHER INFORMATION: Synthetic Construct

<400> SEQUENCE: 92

Arg Gln Pro Lys Ile Trp Phe Pro Asn Arg Arg Lys Pro Trp Lys Lys
1               5                   10                  15

Arg Ala Ser Ser Arg Ala Ser Ser Arg Pro Arg Pro Asp Asp Leu Glu
            20                  25                  30
```